(12) United States Patent
Baker et al.

(10) Patent No.: US 10,934,551 B2
(45) Date of Patent: Mar. 2, 2021

(54) GENE TARGETS FOR IMPROVED ENZYME PRODUCTION IN FUNGI

(71) Applicants: Battelle Memorial Institute, Richland, WA (US); National Technology & Engineering Solutions of Sandia, LLC, Albuquerque, NM (US)

(72) Inventors: Scott E. Baker, Richland, WA (US); Jon K. Magnuson, Richland, WA (US); Morgann C. Reilly, Cambridge, MA (US); Joonhoon Kim, Berkeley, CA (US); John Gladden, Alameda, CA (US); Jed J. Lynn, Fleming Island, FL (US)

(73) Assignees: Battelle Memorial Institute, Richland, WA (US); Natl Tech & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 16/163,509

(22) Filed: Oct. 17, 2018

(65) Prior Publication Data

US 2019/0112611 A1 Apr. 18, 2019

Related U.S. Application Data

(60) Provisional application No. 62/573,354, filed on Oct. 17, 2017.

(51) Int. Cl.

| | |
|---|---|
| *C12N 15/52* | (2006.01) |
| *C12N 15/62* | (2006.01) |
| *C12P 21/00* | (2006.01) |
| *C12P 19/14* | (2006.01) |
| *C12N 9/34* | (2006.01) |
| *C12R 1/685* | (2006.01) |
| *C12N 9/42* | (2006.01) |
| *C12N 9/20* | (2006.01) |
| *C12N 9/50* | (2006.01) |
| *C07K 14/38* | (2006.01) |
| *C12N 9/24* | (2006.01) |
| *C12P 21/02* | (2006.01) |
| *C12N 15/80* | (2006.01) |
| *C07K 14/37* | (2006.01) |

(52) U.S. Cl.
CPC ............ *C12N 15/52* (2013.01); *C07K 14/37* (2013.01); *C07K 14/38* (2013.01); *C12N 9/20* (2013.01); *C12N 9/2402* (2013.01); *C12N 9/2428* (2013.01); *C12N 9/2437* (2013.01); *C12N 9/2445* (2013.01); *C12N 9/50* (2013.01); *C12N 15/80* (2013.01); *C12P 21/02* (2013.01); *C12R 1/685* (2013.01); *C12Y 302/0102* (2013.01); *C12Y 301/01001* (2013.01); *C12Y 301/01003* (2013.01); *C12Y 302/01003* (2013.01); *C12Y 302/01021* (2013.01); *C12Y 302/01176* (2013.01); *C12Y 304/21* (2013.01)

(58) Field of Classification Search
None
See application file for complete search history.

(56) References Cited

U.S. PATENT DOCUMENTS

2015/0218543 A1* 8/2015 Gladden ............... C12N 9/2445
435/99

OTHER PUBLICATIONS

Forment et al., PLoS One 9:e94662, 2014, 13 pages (Year: 2014).*
Sun et al., Antimicrob. Agents Chemo. 58:1434-1442, 2014 (Year: 2014).*
Guo et al., Comp. Struct. Biotechnol. J. 15:161-167, 2017 (Year: 2017).*
Brenner, S., Trends Genet 15:132-133, 1999 (Year: 1999).*
Reilly et al. (Appl. Microbiol. Biotechnol. 102:1797-1807, Jan. 2018 (Year: 2018).*
GenBank Accession No. XM_001399453, Mar. 2011, 2 pages (Year: 2011).*
UniProt Database Accession No. Q8J0U9, Sep. 2017, 2 pages (Year: 2017).*
Barratt et al., "Wild-type and mutant stocks of *Aspergillus nidulans,*" *Genetics* 52:233-246, 1965.
Campen et al., "Expression of naturally ionic liquid-tolerant thermophilic cellulases in *Aspergillus niger,*" *PLoS One* 12:e0189604, 2017.
Chen et al., "BreakDancer: an algorithm for high-resolution mapping of genomic structural variation," *Nature Methods* 6:677-681, 2009.
Chiang et al., "Characterization of a polyketide synthase in *Aspergillus niger* whose product is a precursor for both dihydroxynaphthalene (DHN) melanin and naphtho-γ-pyrone," *Fungal Genet Biol.* 48:430-437, 2010.
De Vries et al., "Comparative genomics reveals high biological diversity and specific adaptations in the industrially and medically important fungal genus *Aspergillus,*" *Genome Biology* 18:28, 2017.
Diallinas, George, "Transceptors as a functional link of transporters and receptors," *Microbiol. Cell* 4:69-73, 2017.
Dos Reis et al., "The low affinity glucose transporter HxtB is also involved in glucose signalling and metabolism in *Aspergillus nidulans,*" *Scientific Reports* 7:45073, 2017.

(Continued)

*Primary Examiner* — David Steadman
(74) *Attorney, Agent, or Firm* — Klarquist Sparkman, LLP

(57) ABSTRACT

Fungi that are genetically inactivated for the mstC gene (or a homolog thereof) are provided, which can also be genetically modified to increase production of heterologous proteins from a glucoamylase promoter. Methods of using these fungi, for example to degrade a biomass, are also provided.

18 Claims, 18 Drawing Sheets
Specification includes a Sequence Listing.

(56) References Cited

OTHER PUBLICATIONS

Forment et al., "Identification of the mstE gene encoding a glucose-inducible, low affinity glucose transporter in *Aspergillus nidulans,*" *J Biol Chem.* 281:8339-8346, 2006.

Fowler et al., "Regulation of the glaA gene of *Aspergillus niger,*" *Curr Genet.* 18:537-545, 1990.

Ganzlin and Rinas, "In-depth analysis of the *Aspergillus niger* glucoamylase (glaA) promoter performance using high-throughput screening and controlled bioreactor cultivation techniques," *J Biotechnol.* 135:266-271, 2008.

Gladden et al., "Glycoside hydrolase activities of thermophilic bacterial consortia adapted to switchgrass," *Appl Environ Microbiol.* 77:5804-5812, 2011.

Gladden et al., "Discovery and characterization of ionic liquid-tolerant thermophilic cellulases from a switchgrass-adapted microbial community," *Biotechnology for Biofuels* 7:15, 2014.

Ignatyev et al., "Synthesis of glucose esters from cellulose in ionic liquids," *Holzforschung.* 66:417-425, 2011.

Jørgensen et al., "Glucose uptake and growth of glucose-limited chemostat cultures of *Aspergillus niger* and a disruptant lacking MstA, a high-affinity glucose transporter," *Microbiology* 153:1963-1973, 2007.

Kowalczyk et al., "Regulation of Plant Biomass Utilization in Aspergillus," *Adv Appl Microbiol.* 88:31-56, 2014.

Kubodera et al., "Pyrithiamine Resistance Gene (ptrA) of *Aspergillus oryzae*: Cloning, characterization and application as a dominant selectable marker for transformation," *Biosci Biotechnol Biochem.* 64:1416-1421, 2000.

Layer et al., "LUMPY: a probabilistic framework for structural variant discovery," *Genome Biology* 15:R84, 2014.

Lee et al., "Regulation of β-glucosidase biosynthesis in *Aspergillus nidulans,*" *FEMS Microbiol Lett.* 135:79-84, 1996.

Li et al., "The Sequence Alignment/Map format and SAMtools," *Bioinformatics* 25:2078-2079, 2009.

Li, H., "A statistical framework for SNP calling, mutation discovery, association mapping and population genetical parameter estimation from sequencing data," *Bioinformatics* 27:2987-2793, 2011.

Li, Heng, "Toward better understanding of artifacts in variant calling from high-coverage samples," *Bioinformatics* 30:2843-2851, 2014.

Lipatova et al., "Ypt/Rab GTPases: Principles learned from yeast," *Crit Rev Biochem Mol Biol.* 50:203-211, 2015.

McKenna et al., "The Genome Analysis Toolkit: a MapReduce framework for analyzing next-generation DNA sequencing data," *Genome Res.* 20:1297-1303, 2010.

Meyer et al., "The cell factory *Aspergillus* enters the big data era: opportunities and challenges for optimising product formation," in Krull R, Bley T (eds) Filaments in Bioprocesses, Springer International Publishing Switzerland, pp. 91-132, 2015.

Nakamura et al., "Expression profile of amylolytic genes in *Aspergillus nidulans,*" *Biosci Biotechnol Biochem.* 70:2363-2370, 2006.

Obenchain et al., "Variant Annotation: a Bioconductor package for exploration and annotation of genetic variants," *Bioinformatics* 30:2076-2078, 2014.

Özcan et al., "Two glucose transporters in *Saccharomyces cerevisiae* are glucose sensors that generate a signal for induction of gene expression," *Proc Natl Acad Sci. USA* 93:12428-12432, 1996.

Park et al., "A thermophilic ionic liquid-tolerant cellulase cocktail for the production of cellulosic biofuels," *PLoS One* 7:e37010, 2012.

Rausch et al., "DELLY: structural variant discovery by integrated paired-end and split-read analysis," *Bioinformatics* 28:i333-i339, 2012.

Ruijter and Visser, "Carbon repression in aspergilli," *FEMS Microbiol Lett.* 151:103-114, 1997.

Schuster et al., "On the safety of *Aspergillus niger*—a review," *Appl Microbiol Biotechnol.* 59:426-435, 2002.

Silveira et al., "Current pretreatment technologies for the development of cellulosic ethanol and biorefineries," *ChemSusChem* 8:3366-3390, 2015.

Sloothaak et al., "*Aspergillus niger* membrane-associated proteome analysis for the identification of glucose transporters," *Biotechnol. Biofuels* 8:150, 2015.

Somerville et al., "Toward a systems approach to understanding plant cell walls," *Science* 306:2206-2211, 2004.

Van Dijck et al., "On the safety of a new generation of DSM *Aspergillus niger* enzyme production strains," *Regul Toxicol Pharmacol.* 38:27-35, 2003.

VanKuyk et al., "A broader role for AmyR in *Aspergillus niger*: regulation of the utilisation of D-glucose or Dgalactose containing oligo- and polysaccharides," *Appl Microbiol Biotechnol.* 93:285-293, 2012.

Yang et al., "Deletion of glucose oxidase changes the pattern of organic acid production in *Aspergillus carbonarius,*" *AMB Express* 4:54, 2014.

Ye et al., "Pindel: a pattern growth approach to detect break points of large deletions and medium sized insertions from paired-end short reads," *Bioinformatics* 25:2865-2871, 2009.

Yu et al., "Ionic liquid-tolerant microorganisms and microbial communities for lignocellulose conversion to bioproducts," *Appl Microbiol Biotechnol.* 100:10237-10249, 2016.

\* cited by examiner

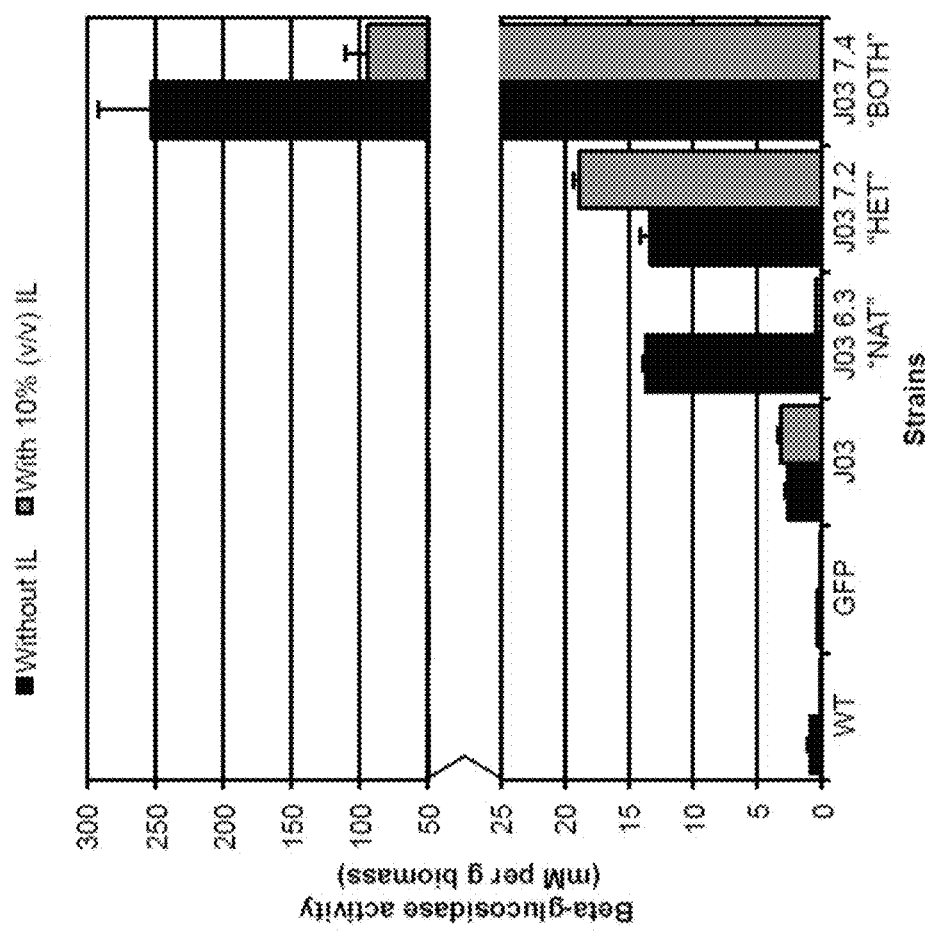

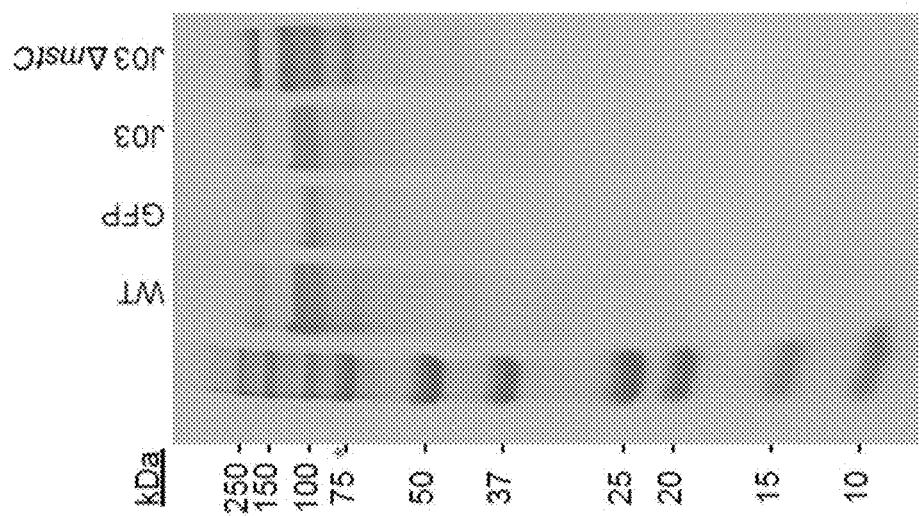

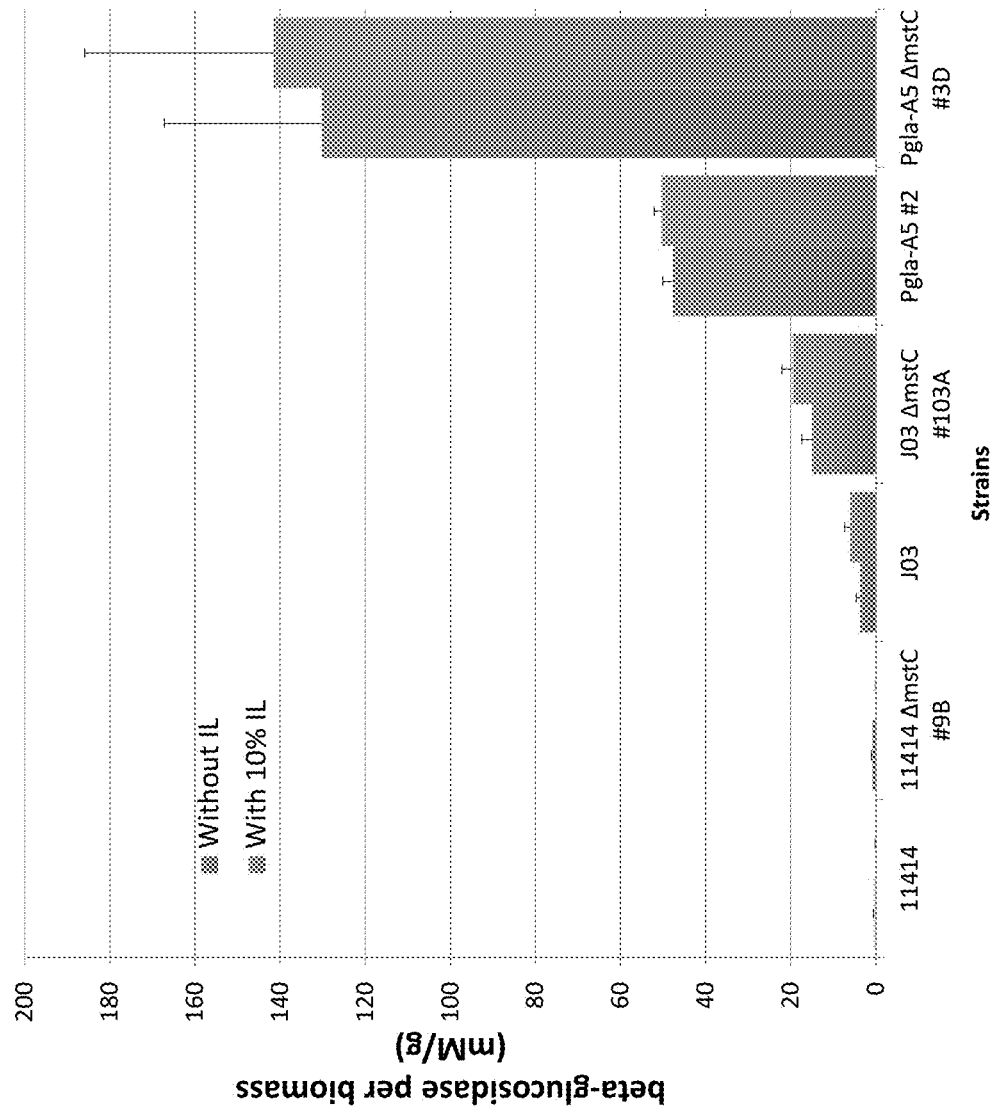

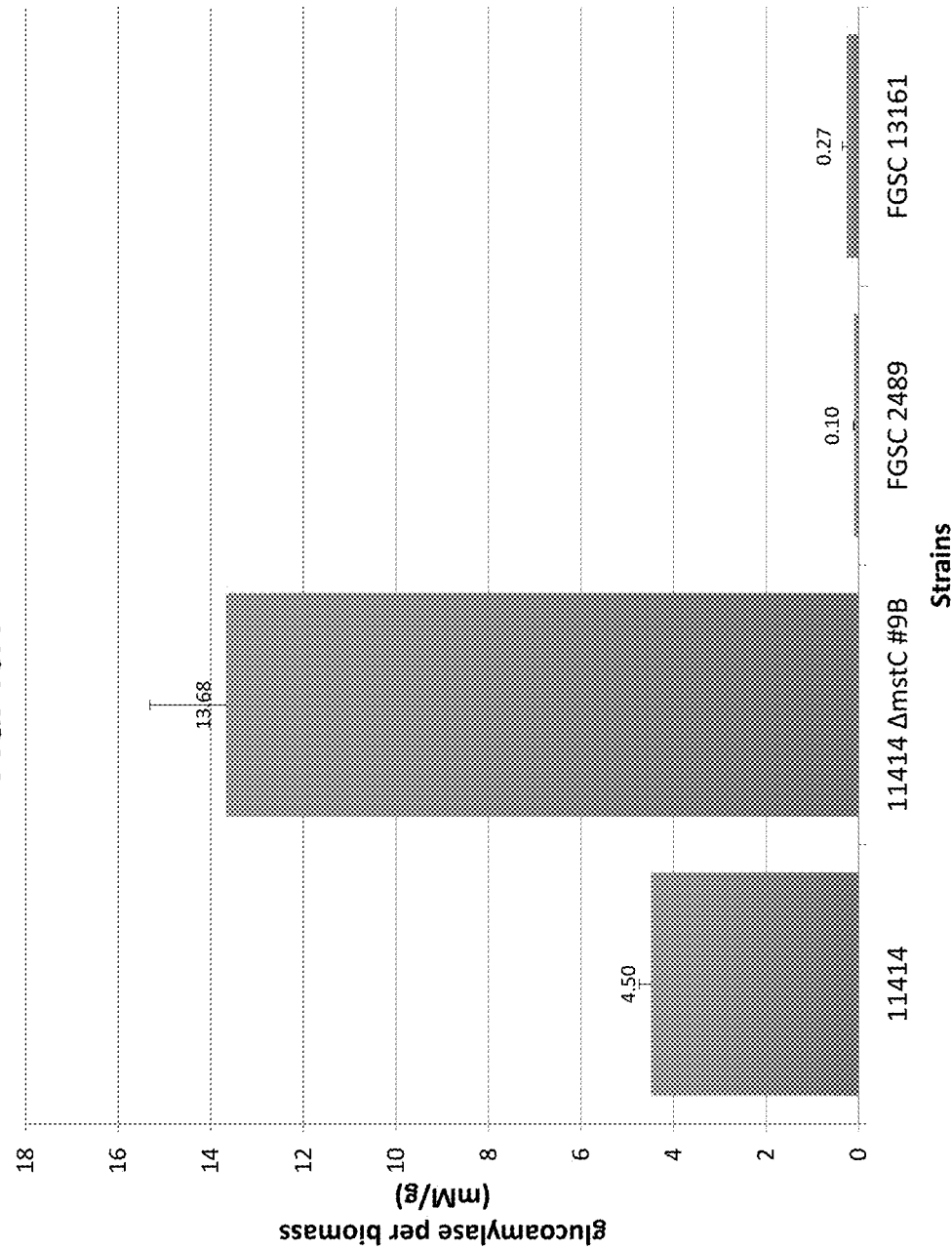

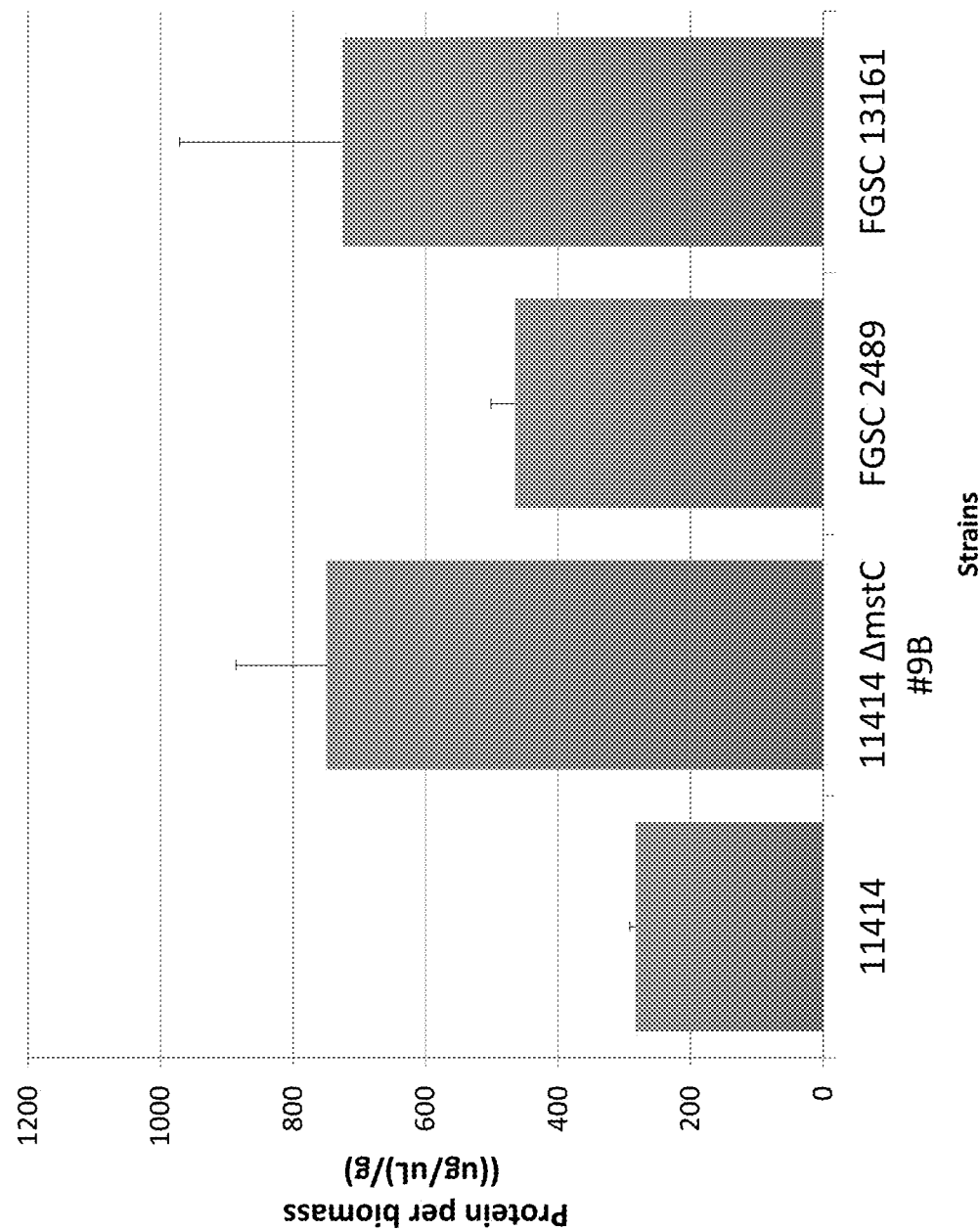

GENE TARGETS FOR IMPROVED ENZYME PRODUCTION IN FUNGI

CROSS REFERENCE TO RELATED APPLICATION

This application claims the benefit of the earlier filing date of U.S. Provisional Application No. 62/573,354, filed on Oct. 17, 2017, which is incorporated herein by reference in its entirety.

ACKNOWLEDGMENT OF GOVERNMENT SUPPORT

This invention was made with government support under Contract DE-AC0576RL01830 and DE-AC02-05CH11231 awarded by the U.S. Department of Energy. The government has certain rights in the invention.

FIELD

This application provides fungi that are genetically inactivated for the mstC gene or a homolog thereof (such as NCU01633), and can be further genetically modified to increase production of heterologous proteins from a glucoamylase promoter. Methods of using these fungi are also provided.

BACKGROUND

Biofuels and bio-based chemicals derived from lignocellulose are promising alternatives to traditional petroleum-originating fuels and chemicals. The plant cell wall is a complex assembly of cellulose, hemicellulose, lignin, pectin, and proteins (Somerville et al. 2004). Breaking down this heterogeneic substrate into its constituent monomers and oligomers currently requires a combination of physical, chemical, and/or biological deconstruction methods. A variety of chemical pretreatment methods have been explored, including acids, bases, solvents, and oxidation (Silveira et al. 2015). For the subsequent enzymatic hydrolysis steps to be both economically and environmentally viable, proteins that can remain active in the presence of residual pretreatment chemicals need to be identified. It would also be beneficial if these enzymes can be produced economically and at a large scale.

Ionic liquid (IL) solvents are used for biomass pretreatment (Yu et al. 2016). There has been a concerted effort to identify cellulose cocktail components that are IL-tolerant as current commercial mixtures are not. For example, a number of cellulolytic enzymes with thermophilic and IL-tolerant characteristics were identified from a switchgrass-degrading bacterial community (Gladden et al. 2011). However, many of the species producing these enzymes are not easily cultured. The predicted cellulolytic bacterial enzymes were produced either in vitro or from *Escherichia coli* in order to characterize their activity over a range of temperature, pH, and IL concentration (Gladden et al. 2014). To produce these enzymes at a larger scale, these sequences were cloned into the fungal host, *Aspergillus niger* (Campen et al.).

Filamentous fungi are commonly used for the commercial production of chemicals and enzymes. The ability of *A. niger* to grow aerobically over a wide range of both temperatures and pHs is advantageous in industrial settings (Schuster et al. 2002; Oliveira et al. 2001). In addition, the organism is non-pathogenic and does not produce the mycotoxins that are common in some other related fungal species. It is therefore categorized as GRAS (generally recognized as safe) by the US Food and Drug Administration, meaning that substances generated using *A. niger* are considered harmless as food additives (Schuster et al. 2002, van Dijck et al. 2003). Because of its established use in industry, numerous large-scale fermentation protocols for *A. niger* exist. Finally, *A. niger* has a well-developed molecular toolbox, including various auxotrophic and antifungal resistance markers, a fully sequenced genome, and various transformation protocols, thus making it conducive to genetic manipulation.

SUMMARY

A forward mutagenesis strategy was used to identify methods to enhance heterologous enzyme production in *A. niger*. A strain engineered to produce one of the IL-tolerant bacterial β-glucosidases (BGs) was subjected to chemical mutagenesis and the resulting strains screened for increased enzyme production. Subsequent whole-genome resequencing of a dozen hyper-production mutants identified hundreds of genetic lesions, and bioinformatics analysis revealed several loci potentially associated with heterologous enzyme hyper-production, including those that appear to be specific to the heterologous protein expression construct used. One of the identified loci was annotated as a low-affinity glucose transporter, mstC. It is shown herein that the deletion of mstC improves the heterologous enzyme production driven by a glucoamylase promoter ($P_{glaA}$), some examples by at least four-fold. This allows for increased production of heterologous proteins by *Aspergillus* species such as *A. aculeatus, A. awamori, A. brasiliensis, A. carbonarius, A. flavus, A. foetidus, A. fumigatus, A. furnigatus, A. nidulans, A. niger, A. oryzae, A. pseudoterreus, A. sojae, A. terreus, A. tubingensis,* and *A. wentii* for industrial use. In addition, functional deletion of mstC increased glucoamylase production. Amylolytic enzymes are critical to ethanol production and methods to increase amylolytic enzymes can be used to decrease enzyme production costs.

Based on these observations, provided herein are isolated fungi, such as those in the class Eurotiomycetes (e.g., *Aspergillus*, such as *A. niger*) or Sordariomycetes (e.g., *Neurospora* or *Glomerella*, such as *N. crassa*) a species of, which include a genetic inactivation of a mstC gene or a homolog thereof, such as NCU01633. Such fungi can be recombinant (e.g., non-naturally occurring). In some examples, the mstC gene is genetically inactivated by non-synonymous mutation or by insertional mutation. In some examples, the mstC gene that is genetically inactivated was a nucleic acid molecule having at least 95%, at least 98%, at least 99%, or 100% sequence identity to SEQ ID NO: 1 or 3 or to nt 82 to 1764 of SEQ ID NO: 1 (e.g., prior to its inactivation). In some examples, the mstC gene that is genetically inactivated encoded a protein comprising at least 95%, at least 98%, at least 99%, or 100% amino acid sequence identity to SEQ ID NO: 2 (e.g., prior to its inactivation). In some examples, the mstC homolog that is genetically inactivated is a NCU01633 gene, such as nucleic acid molecule having at least 95%, at least 98%, at least 99%, or 100% sequence identity to SEQ ID NO: 9 or 10 or to nt 652 to 2250 of SEQ ID NO: 10 (e.g., prior to its inactivation). In some examples, the NCU01633 gene that is genetically inactivated encoded a protein comprising at least 95%, at least 98%, at least 99%, or 100% amino acid sequence identity to SEQ ID NO: 11 (e.g., prior to its inactivation). Fungi containing a genetically inactivated mstC or homolog thereof can further include a glucoamylase promoter (e.g., a nucleic acid molecule having at least 95%, at least 98%, at least 99%, or 100% sequence identity to SEQ ID NO: 8) operably linked to a heterologous (i.e., non-native) protein coding sequence, such as a heterologous enzyme (e.g., beta-glucosidase (BG), glycoside hydrolase, carbohydrate esterase, protease, lipase, liginase, cellulase, or hemicellulase), chimeric protein that includes a secreting signal sequence, or a chimeric protein including glucoamylase linked to a protein of interest. Such fungi can produce or express the heterologous protein. In some examples, fungi containing a genetically inactivated mstC or homolog thereof can further include one or more mutations in an AmyR gene, a mutation in an CreA gene, or both, wherein the mutations decrease expression and/or activity of AmyR and/or CreA.

Also provided are methods of using the disclosed fungi. For example, provided are methods of expressing expression of a heterologous protein. Such methods can include culturing one or more isolated (e.g., recombinant) fungi disclosed herein, under conditions that permit the fungus having a genetically inactivated mstC gene or homolog thereof and a heterologous protein coding sequence operably linked to a glucoamlyase promoter, to express the heterologous protein, thereby expressing the heterologous protein. In some examples, expression of a heterologous protein, such as a heterologous enzyme, is increased by at least 2-fold, such as at least 3-fold, or at least 4-fold, as compared to expression of the heterologous enzyme in a fungus containing a native (e.g., non-mutated and functional) mstC gene or homolog thereof.

Also provided are methods of using the isolated (e.g., recombinant) fungi disclosed herein to degrade a biomass containing cellulose. For example, such methods can include incubating the biomass with one or more fungi disclosed herein having a genetically inactivated mstC gene (or homolog thereof) and a heterologous protein coding sequence operably linked to a glucoamlyase promoter, under conditions that permit the fungus to express the heterologous protein (e.g., BG or other protein in Table 1) from the glucoamylase promoter, thereby degrading the biomass. In other examples, the method includes incubating a biomass with one or more heterologous proteins (e.g., BG or other enzyme or protein listed in Table 1, or combinations thereof, such as one or more heterologous proteins that can degrade the biomass) obtained from the AmstC fungi that include a glucoamylase promoter operably linked to a heterologous protein (for example enzymes secreted in the growth media of the mutant fungi and collected or isolated) under conditions that permit the secreted heterologous protein to degrade the biomass. For example, the biomass can be incubated with the one or more heterologous proteins in an appropriate liquid material, at an appropriate temperature and pH. The heterologous protein(s) obtained from the AmstC fungi degrade the biomass. Thus, the method can further include culturing the AmstC fungi and separating or isolating the heterologous protein(s) expressed in and secreted by the AmstC mutant strain, and then adding the separated heterologous protein(s) to the biomass. In some examples, the method further includes incubating the biomass with one or more ionic liquids, including, but not limited to, ethyl methylimidazolium acetate, cholinium lysinate, cholinium alpha-ketoglutarate, or combinations thereof.

Also provided are methods of using the isolated (e.g., recombinant) fungi disclosed herein to increase glucoamylase production in a fungus. In one example, the method includes culturing one or more isolated (e.g., recombinant) fungi disclosed herein that has a genetically inactivated mstC gene (or homolog thereof), under conditions that permit the fungus to express native glucoamylase; thereby increasing expression of glucoamylase relative to a fungus with a native (e.g., non-mutated and functional) mstC gene (or homolog thereof).

The foregoing and other objects and features of the disclosure will become more apparent from the following detailed description, which proceeds with reference to the accompanying figures.

BRIEF DESCRIPTION OF THE DRAWINGS

FIGS. 1A-1B are bar graphs showing growth of WT, GFP, J03, and J03-derivative strains in inducing culture conditions (CSLàHMM). (A) β-glucosidase activity in culture supernatant as measured using the described pNPG assay: addition of ionic liquid [$C_2$mim]OAc to reactions allows for distinction between native and heterologous enzymes. Enzyme activity (millimolar equivalents) was normalized to dry weight of fungal biomass (g). The addition of ionic liquid to the reactions allows for distinction between native and heterologous enzyme activity. (B) Total secreted protein as measured by Bradford assay (μg/μL) and normalized to dry weight of fungal biomass (g). Data drawn from biological replicates (n=3); error bars indicate standard deviation.

FIG. 5 shows a digital image of banding pattern examined by polyacrylamide gel electrophoresis (8-16% gradient polyacrylamide gels). Banding patterns from culture supernatants of WT, GFP, J03, and J03 AmstC are shown. Predicted molecular weight of J03 (~80 kDa) is indicated with *.

FIG. 8A is a bar graph showing beta-glucosidase activity (mM per g biomass) in WT, J03 and ΔmstC strains using the pNPG assay. Beta-glucosidase activity in J03 and J03 ΔmstC strains were measured with and without 10% IL.

FIG. 10A is a bar graph showing glucoamylase production in A. niger WT (11414) and N. crassa WT (FGSC 2489) as compared to the A. niger ΔmstC mutant and the N. crassa ΔNCU001633 mutant (FGSC 13161).

FIG. 10B is a bar graph showing the total protein levels in A. niger WT (11414) and N. crassa WT (FGSC 2489) as compared to the A. niger ΔmstC mutant and the N. crassa ΔNCU001633 mutant (FGSC 13161).

FIGS. 11A and 11B show the mstC locus (SEQ ID NO: 1) and encoded protein (SEQ ID NO: 2). (A) Native genomic DNA: italicized lowercase text is 5' UTR 3' UTR sequence, lowercase text is intron sequence, and uppercase text is exon sequence. Mutations in the J03-derivative strains J03 1.1, J03 1.6, J03 1.7, J03 7.2, and J03 8.2, are indicated either by bold red text for a nucleotide point mutation from native guanine or underlined text indicating an insertion site between two bases. (B) Native amino acid sequence: mutations in the strains J03 1.1, J03 1.6, J03 1.7, J03 7.2, and J03 8.2, are indicated either by bold red text for an amino acid change resulting from nucleotide change or by underlined text for an insertion site between two amino acid residues.

SEQUENCE LISTING

Figure 1B:
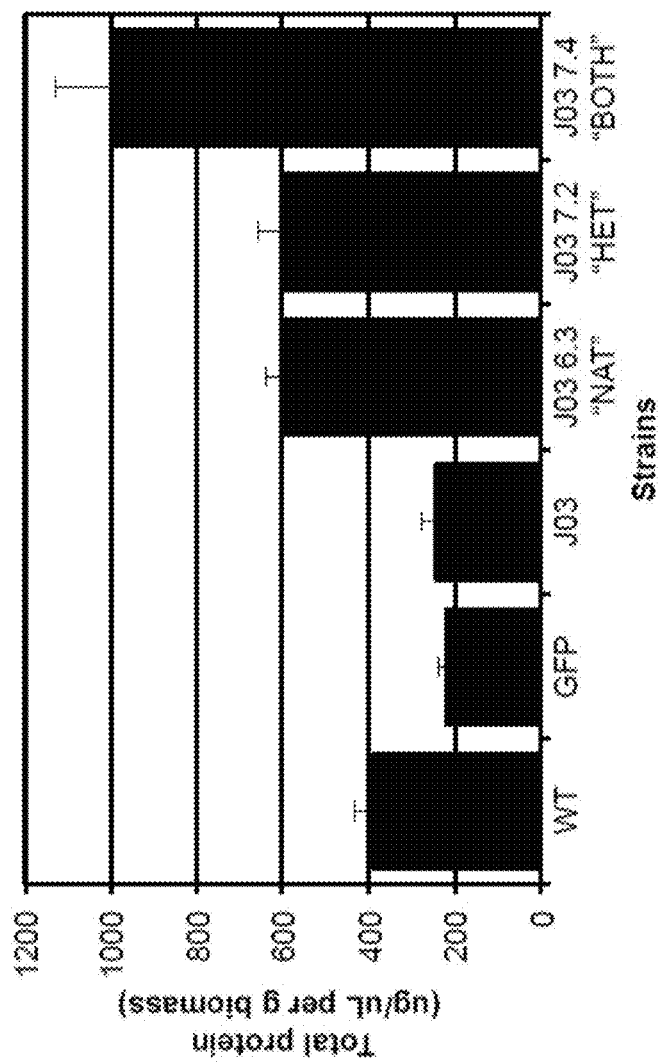

The nucleic acid sequences listed in the accompanying sequence listing are shown using standard letter abbreviations for nucleotide bases and amino acids, as defined in 37 C.F.R. 1.822. Only one strand of each nucleic acid sequence is shown, but the complementary strand is understood as included by any reference to the displayed strand. The sequence listing generated on Oct. 17, 2018, 40 kb, submitted herewith, is incorporated by reference in its entirety. In the accompanying sequence listing:

SEQ ID NO: 1 is an exemplary mstC nucleic acid coding sequence from A. niger. nucleotides (nt) 1 to 81 and 1765 to 2069 show untranslated regions or UTRs (noncoding exon sequences), nt 82 to 1764 is the coding region.

SEQ ID NO: 2 is an exemplary mstC protein sequence from A. niger.

SEQ ID NO: 3 is an exemplary mstC nucleic acid genomic sequence from A. niger. nt 1 to 81 and 1885 to 2189 show UTRs (noncoding exon sequences). nt 293 to 353 and 467 to 525 show introns.

SEQ ID NOS: 4 and 5 are exemplary amyR nucleic acid and protein sequences, respectively, from A. niger. The coding sequence of SEQ ID NO: 4 is nt join (1 . . . 980,1032 . . . 1482,1541 . . . 1849)

SEQ ID NOS: 6 and 7 are exemplary creA nucleic acid and protein sequences, respectively, from A. niger. The coding sequence of SEQ ID NO: 6 is nt 1339 to 2622.

SEQ ID NO: 8 is an exemplary glucoamylase promoter sequence from A. niger.

SEQ ID NO: 9 is an exemplary NCU01633 nucleic acid genomic sequence from N. crassa. nt 1 to 651 and 2323 to 2668 show UTRs. nt 797 to 869 shows an intron.

SEQ ID NO: 10 is an exemplary NCU01633 nucleic acid coding sequence from N. crassa. nt 1 to 651 and 2251 to 2596 show untranslated regions. Thus the coding sequence is nt 652 to 2250 of SEQ ID NO: 10.

SEQ ID NO: 11 is an exemplary NCU01633 protein sequence from N. crassa.

DETAILED DESCRIPTION

I. Terms

Unless otherwise explained, all technical and scientific terms used herein have the same meaning as commonly understood by one of ordinary skill in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All references and Genbank® Accession numbers mentioned herein are incorporated by reference in their entireties (the sequence available on Oct. 17, 2018). The materials, methods, and examples are illustrative only and not intended to be limiting.

In order to facilitate review of the various embodiments of the disclosure, the following explanations of specific terms are provided:

*Aspergillus*: A genus of fungi that can grow in the presence of high osmotic pressure (e.g., high concentration of sugar, salt, etc.). *Aspergillus* species are highly aerobic and are found in almost all oxygen-rich environments, where they commonly grow as molds on the surface of a substrate, as a result of the high oxygen tension. Hundreds of *Aspergillus* species are known, and can be used as a source of *Aspergillus* in which to genetically inactivate a mstC gene. Such species can be used in the methods provided herein. Exemplary species that can be used, include, but are not limited to: *A. aculeatus, A. awamori, A. brasiliensis, A. carbonarius, A. flavus, A. foetidus, A. fumigatus, A. furnigatus, A. nidulans, A. niger, A. oryzae, A. pseudoterreus, A. sojae, A. terreus, A. tubingensis*, and *A. wentii*.

amyR: A gene encoding alpha-amylase, a protein that hydrolyses alpha bonds of large polysaccharides. The term amyR (or amyR) includes any amyR gene (such as a fungal amyR sequence), cDNA, mRNA, or protein, that is an amyR involved in endohydrolysis of alpha linkages in polysaccharides and production of native beta-glucosidase in *A. niger* and when genetically inactivated results in a fungus that has an ability to produce more native beta-glucosidase than the parent strain.

amyR sequences are publicly available. For example, GenBank Accession No AJ005258.1 discloses an *Aspergillus oryzae* amyR nucleic acid sequence (corresponding protein GenBank Accession No. CAA06445.1); GenBank Accession No AF155808.1 discloses an *Aspergillus niger* amyR nucleic acid sequence (corresponding protein GenBank Accession No. AAD38984.1); and GenBank Accession No AB753014.1 discloses an *Aspergillus sojae* amyR nucleic acid sequence (corresponding protein GenBank Accession No. BAM62430.1). However, amyR sequences can include variant sequences (such as allelic variants and homologs) that have amyR activity but when genetically inactivated in *Aspergillus* results a fungus that has an ability to produce more native beta-glucosidase than the parent strain.

Biomass: Refers to plants or plant-based materials that include lignocellulose (thus also referred to as "lignocellulosic biomass"), which is not used for food or feed, but are used as an energy source. Biofuels derived from lignocellulose are alternative to petroleum-originating fuels and chemicals. An example is a fermentation of lignocellulosic biomass to ethanol. The combustion of lignocellulosic ethanol produces no net carbon dioxide in the atmosphere, thus is a carbon-neutral source of energy.

Lignocellulose biomass is composed of carbohydrate polymers (cellulose, hemicellulose), and an aromatic polymer (lignin). These carbohydrate polymers contain different sugar molecules and they are tightly bound to lignin. Breaking down this heterogeneic substrate into its constituent monomers and oligomers requires physical, chemical, and/or biological deconstruction methods.

creA: A gene encoding a DNA-binding protein that regulates transcription. The term creA (or creA) includes any creA gene (such as a fungal creA sequence), cDNA, mRNA, or protein, involved in controlling carbon source utilization through ubiquitination and deubiquitination, and when genetically inactivated results in a fungus that has an ability to produce more heterologous protein than the parent strain.

creA sequences are publicly available. For example, GenBank Accession No AF322183.1 discloses an *Aspergillus oryzae* creA nucleic acid sequence (corresponding protein GenBank Accession No. AAK11189.1); GenBank Accession No L03811.1 discloses an *Aspergillus niger* creA nucleic acid sequence (corresponding protein GenBank Accession No. AAA32690.1); and GenBank Accession No AB024314.1 discloses an *Aspergillus aculeatus* creA nucleic acid sequence (corresponding protein GenBank Accession No. BAA75519.1). However, creA sequences can include variant sequences (such as allelic variants and homologs) that have creA activity but when genetically inactivated in *Aspergillus* results in a fungus that has an ability to produce more heterologous protein than the parent strain.

Detectable: Capable of having an existence or presence ascertained. For example, production of an exogenous or non-native protein, such as an exogenous beta-glucosidase (BG), is detectable if the signal generated is strong enough to be measurable.

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced. In an example, the disclosed fungi having a genetically inactivated mstC gene (referred to as ΔmstC) and a glucoamylase promoter operably linked to a heterologous protein coding sequence can be used to express the heterologous gene or protein (such as BG).

The expression of a nucleic acid molecule can be altered relative to a normal (wild type) nucleic acid molecule. Alterations in gene expression, such as differential expression, include but are not limited to: (1) overexpression; (2) underexpression; or (3) suppression of expression. Alternations in the expression of a nucleic acid molecule can be associated with, and in fact cause, a change in expression of the corresponding protein.

Genetic inactivation: When used in reference to the expression of a nucleic acid molecule, such as a gene, refers to any process which results in a decrease in production of a gene product (or even elimination of production of a gene product). A gene product can be RNA (such as mRNA, rRNA, tRNA, and structural RNA) or protein, such as an mstC protein or homolog thereof. Therefore, gene inactivation includes processes that decrease transcription of a gene or translation of mRNA, such as a decrease of at least 20%, at least 30%, at least 40%, at least 50%, at least 60%, at least 75%, at least 80%, at least 90%, at least 95%, at least 98%, at least 99%, or even 100%.

For example, a mutation, such as a substitution, partial or complete deletion, insertion, or other variation, or combinations thereof, can be made to a gene sequence that significantly reduces (and in some cases eliminates) production of the gene product or renders the gene product substantially or completely non-functional. For example, a genetic inactivation of an mstC gene in *Aspergillus* (e.g., *A. niger*) (or homolog thereof such as NCU01633 from *N. crassa*) results in *Aspergillus* having a non-functional or non-existent mstC sugar transporter, which results in an ability of the fungus to produce increased amounts of a heterologous protein. Genetic inactivation is also referred to herein as "functional deletion".

Glucoamylase: Also known as amyloglucosidase (EC 3.2.1.3). Glucoamylase is a starch-breaking enzyme capable of breaking both α-1,4 and α-1,6 bonds to digest starch. During hydrolysis, glucose units are removed from the non-reducing end of the substrate molecule.

Glucoamylase sequences are publicly available. For example, GenBank Accession No D10698.1 discloses an *Aspergillus oryzae* glucoamylase nucleic acid sequence (corresponding protein GenBank Accession No. BAA01540.1); GenBank Accession No AY250996.1 discloses an *Aspergillus niger* glucoamylase nucleic acid sequence (corresponding protein GenBank Accession No. AAP04499.1); and GenBank Accession No KU936058.1 1 discloses an Aspergillusflavus glucoamylase nucleic acid sequence (corresponding protein GenBank Accession No. ARF07718.1). However, glucoamylase sequences can include variants of these sequences (such as allelic variants and homologs).

An exemplary glucoamylase promoter from *A. niger* is shown in SEQ ID NO: 8.

Isolated: An "isolated" biological component (such as a nucleic acid molecule, or protein) has been substantially separated, produced apart from, or purified away from other biological components in the cell of the organism in which the component occurs, for example, other chromosomal and extra-chromosomal DNA and RNA, and proteins. Nucleic acid molecules and proteins which have been "isolated" include nucleic acid molecules and proteins purified by standard purification methods. The term also embraces nucleic acid molecules and proteins prepared by recombinant expression in a host cell as well as chemically synthesized proteins and nucleic acids. Samples of isolated biological components include samples of the biological component wherein the biological component represents greater than 90% (for example, greater than 95%, such as greater than 98%) of the sample.

An "isolated" microorganism (such as an mstCA strain of *Aspergillus*) has been substantially separated or purified away from microorganisms of different types, strains, or species. Microorganisms can be isolated by a variety of techniques, including serial dilution and culturing and resistance to certain chemicals.

Heterologous protein: A protein that is exogenous (e.g., foreign or non-native) with respect to a particular cell or organism, for example one that is introduced into, or produced within, a different host (recipient) from that in which the protein is naturally located. "Heterologous" refers to the fact that the protein naturally occurs in a different cell or organism from the recipient cell or organism (e.g., the protein is not found in the recipient cell in nature). For example, a protein expressed in one organism and introduced by genetic engineering techniques into a different organism is a "heterologous" protein.

Increase or Decrease: A statistically significant positive or negative change, respectively, in quantity from a control value (such as a value before ΔmstC mutation). An increase is a positive change, such as an increase at least 50%, at least 100%, at least 200%, at least 300%, at least 400% or at least 500% as compared to the control value. A decrease is a negative change, such as a decrease of at least 20%, at least 25%, at least 50%, at least 75%, at least 80%, at least 90%, at least 95%, at least 98%, at least 99%, or at least 100% decrease as compared to a control value. In some examples the decrease is less than 100%, such as a decrease of no more than 90%, no more than 95% or no more than 99%.

Incubate or culture: Cells, such as fungal cells, grown or maintained under controlled conditions, for example in a laboratory. Cells are expanded in culture when they are placed in or on a growth medium under conditions that facilitate cell growth and/or division, resulting in a larger population of the cells. When cells are expanded in culture, the rate of cell proliferation is typically measured by the amount of time required for the cells to double in number, otherwise known as the doubling time. In some examples, incubation or culturing is performed in a fermenter.

Ionic liquid (IL): An ionic liquid is a salt in the liquid state, also referred to as "liquid electrolytes," "ionic melts," "ionic fluids," "fused salts," "liquid salts," and "ionic glasses. ILs are largely made of ions and short-lived ion pairs. At least one ion has a delocalized charge and one component is organic, which prevents the formation of a stable crystal lattice. Examples include compounds based on the 1-Ethyl-3-methylimidazolium (EMIM) cation and include: EMIM:Cl, EMIM dicyanamide, $(C_2H_5)(CH_3)C_3H_3N_2^{+*}N(CN)_2^-$, 1-butyl-3,5-dimethylpyridinium bromide, and 1-ethyl-3-methylimidazolium acetate ($[C_2mim]$OAc). In some examples, the IL is a ethyl methylimidazolium acetate, cholinium lysinate, cholinium alpha-ketoglutarate, or combination thereof.

Ionic liquids are effective in biomass pretreatment by their ability to separate lignin from cellulose. The cellulose produced is de-agglomerated and can be hydrolyzed to sugars. The ionic liquids are stable and do not decompose cellulose, can be used at low temperature, can be easily separated, and are potentially recyclable. For example, the transformation of cellulose into glucose ester alpha-D-glucose pentaacetate can be carried out in ionic liquid 1-butyl-3-methylimidazolium chloride. (Igor et al., 2011).

mstC: A monosaccharide transporter, for example in *A. niger*. The term mstC (or mstC) includes any mstC gene (such as a fungal mstC sequence), cDNA, mRNA, or protein, that is an mstC having monosaccharide transporter activity, and when genetically inactivated results in a fungus that can produce increased amounts of a heterologous protein relative to the parent strain.

mstC sequences are publicly available. For example, GenBank Accession No AY081847 disclose a nucleic acid sequence of an *A. niger* mstC. Exemplary mstC nucleic acid and protein sequences are provided in SEQ ID NOS: 1-3. However, mstC sequences include variant sequences (such as allelic variants and homologs) that have mstC activity but when genetically inactivated in *Aspergillus* results in a fungus that has an ability to produce increased amounts of a heterologous protein relative to the parent strain. One skilled in the art will appreciate that homologs of mstC can be functionally deleted in other fungi, such as NCU01633 of *Neurospora*.

Mutation: A change in a nucleic acid sequence (such as a gene sequence) or amino acid sequence, for example as compared to a nucleic acid or amino acid sequence present in a wild-type or native organism. In particular examples, a mutation is introduced into an mstC, creA, and/or amyR gene in *Aspergillus* (or equivalent homolog in other fungi). Mutations can be introduced, for example using molecular biology methods. In particular examples, a mutation includes one or more nucleotide or amino acid substitutions, deletions, insertions, or combinations thereof. In particular examples, the presence of one or more mutations in a gene can significantly inactivate that gene.

Operably linked: A first nucleic acid sequence is operably linked with a second nucleic acid sequence when the first nucleic acid sequence is placed in a functional relationship with the second nucleic acid sequence. For instance, a promoter (such as a glucoamylase promoter) is operably linked to a coding sequence (such as a coding sequence of an exogenous protein, such as beta-glucosidase) if the promoter affects the transcription or expression of the coding sequence. Generally, operably linked DNA sequences are contiguous and, where necessary to join two protein-coding regions, in the same reading frame.

Promoter: An array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor). An exemplary promoter is a glucoamylase promoter, such as the one shown in SEQ ID NO: 8.

Recombinant: A recombinant molecule (e.g., nucleic acid or protein) is one that has a sequence that is not naturally occurring, for example, includes one or more nucleotide or amino acid substitutions, deletions or insertions, and/or has a sequence that is made by an artificial combination of two otherwise separated segments of sequence. In one example includes a native promoter (e.g., glucoamylase promoter) operably linked to a heterologous protein (e.g., BG). This artificial combination can be accomplished, for example, by chemical synthesis or by the artificial manipulation of isolated segments of nucleic acids, for example, by genetic engineering techniques. A recombinant cell, such as a recombinant fungal cell, is one not found in nature, such as one containing a nucleic acid or protein molecule not found in nature, for example due to genetic manipulation, such as introduction of a foreign or non-native nucleic acid molecule or protein.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q -1 -r 2.

To compare two amino acid sequences, the options of Bl2seq can be set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (e.g., 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (i.e., 1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (i.e., 15-20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG. In addition, a manual alignment can be performed. Proteins with even greater similarity will show increasing percentage identities when assessed by this method, such as at least 75%, 80%, 85%, 90%, 95%, or 99% sequence identity.

Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least 60%, 70%, 80%, 90%, 95%, 98%, or 99% sequence identity determined by this method.

One of skill in the art will appreciate that these sequence identity ranges are provided for guidance only; it is possible that strongly significant homologs could be obtained that fall outside the ranges provided.

Transformed: A cell, such as a fungal cell, into which a nucleic acid molecule has been introduced, for example by molecular biology methods. Transformation encompasses all techniques by which a nucleic acid molecule can be introduced into a cell, including, but not limited to transfection with viral vectors, conjugation, transformation with plasmid vectors, and introduction of naked DNA by electroporation, lipofection, and biolistic particle delivery.

II. Overview

This disclosure provides the first demonstration that genetic inactivation of a mstC gene substantially increase expression of a heterologous protein in *Aspergillus niger*, while the total protein production stays similar to the parent strain.

The present disclosure provides an isolated fungus having its mstC gene (or homolog thereof, such as NCU0163) genetically inactivated. In some embodiments, the isolated fungus is in the class Eurotiomycetes (such as *Aspergillus*) or Sordariomycetes (such as *Neurospora*). In some examples, if an *Aspergillus* species is used, mstC is genetically inactivated. In other examples, if a *Neurospora* species is used, the nearest homolog to mstC, NCU01633, is genetically inactivated.

Provided herein are J03-derivative mutant strains generated by mutation of the J03 strain that are categorized according to their ability to generate native and/or heterologous beta-glucosidase in *Aspergillus niger*. In some embodiments, the mstC gene or homolog thereof is genetically inactivated by nonsynonymous mutation, insertional mutation, or CRISPR-Cas9 genome editing technology. In some examples, the mstC gene that is genetically inactivated includes a nucleic acid molecule that includes at least 90%, at least 95%, at least 98%, at least 99%, or 100% sequence identity to SEQ ID NO: 1 or 3 or to nt 82 to 1764 of SEQ ID NO: 1, prior to its genetic inactivation. In some examples, the mstC gene that is genetically inactivated encodes a protein having at least 90%, at least 95%, at least 98%, at least 99%, or 100% sequence identity to SEQ ID NO: 2, prior to its genetic inactivation. In some examples, the mstC homolog that is genetically inactivated includes a nucleic acid molecule that includes at least 90%, at least 95%, at least 98%, at least 99%, or 100% sequence identity to SEQ ID NO: 9 or 10 or to nt 652 to 2250 of SEQ ID NO: 10, prior to its genetic inactivation. In some examples, the mstC gene homolog that is genetically inactivated encodes a NCU01633 protein having at least 90%, at least 95%, at least 98%, at least 99%, or 100% sequence identity to SEQ ID NO: 11, prior to its genetic inactivation.

The ΔmstC fungi (which generically refers to any fungi with its mstC gene or homolog thereof, such as NCU01633, genetically inactivated) can further include a glucoamylase promoter operably linked to a heterologous protein coding sequence. Such fungi can produce the heterologous protein. Exemplary heterologous proteins are provided in Table 1.

TABLE 1

Exemplary heterologous proteins
Heterologous protein

Enzyme such as beta-glucosidase (BG), glycoside hydrolase, carbohydrate esterase, protease, lipase, liginase, cellulase, hemicellulase
chimeric protein that includes a secreting signal protein, such as a yeast mating pheromone secretion signal
chimeric protein that includes a native fungal glucoamylase linked/attached to the protein of interest (wherein the proteins can be separated by a linker or a kex or other cleavage recognition site)

The ΔmstC fungi (such can include a include a glucoamylase promoter operably linked to a heterologous protein coding sequence) can further include a mutated amyR gene, a mutated creA gene, or both. Such mutations can include one or more point mutations, such as at least 2, at least 5, or at least 10 point mutations, such as deletions, insertions, substitutions, or combinations thereof. In some examples, amyR and creA genes are mutated or genetically inactivated by missense, nonsense, or deletion. Such genetic inactivation decreases activity of amyR or creA, such as at least 50%, at least 60%, at least 70%, at least 80%, at least 90%, or at least 95% reduction in the activity of such genes or proteins.

Methods of using the ΔmstC fungi that include a glucoamylase promoter operably linked to a heterologous protein coding sequence are provided. Such methods can be used to express a heterologous protein, for example by culturing the recombinant fungus under conditions that permit the fungus to express the heterologous protein. For example, the recombinant fungus can be grown or cultured in an appropriate culture medium at an appropriate temperature. In some embodiments, the expressed heterologous protein is a heterologous enzyme (e.g., beta-glucosidase or other protein listed in Table 1). In some embodiments, other proteins are chimeric proteins, such as one that includes a secreting signal, one that includes a glucoamylase linked to the protein of interest, or combinations thereof, are expressed. In some examples, the expression of the heterologous protein in the ΔmstC mutant strain is increased at least two-fold (such as at least 3-fold, or at least 4-fold) compared to the expression of the heterologous enzyme in a WT fungus (e.g., one having a native mstC gene).

Methods of using the ΔmstC fungi that include a glucoamylase promoter operably linked to a heterologous protein coding sequence to degrade a biomass are provided. For example, the method can include incubating a biomass with ΔmstC fungi that include a glucoamylase promoter operably linked to a heterologous protein, such as BG, under conditions that permit the fungus to express the heterologous protein from the glucoamylase promoter, thereby degrading the biomass. Expression of the heterologous protein from the glucoamylase promoter degrades the biomass. In some embodiments, the biomass is further incubated with ionic liquids, such as ethyl methylimidazolium acetate, cholinium lysinate, cholinium alpha-ketoglutarate, or combinations thereof. In some examples, the biomass is incubated with ionic liquids prior to, or concurrently with, ΔmstC fungi. In some examples, the biomass is incubated with ionic liquids after incubation with ΔmstC fungi.

Present disclosure also provides a method of increasing glucoamylase production in a fungus by culturing a ΔmstC fungi to express native glucoamylase. In some examples, expression of the glucoamylase in the ΔmstC mutant strain is increased at least two-fold (such as at least 3-fold, or at least 4-fold) compared to the expression of the glucoamylase in a WT fungus (e.g., one having a native mstC gene).

III. ΔmstC Fungi

The present disclosure provides isolated fungi having its native mstC gene (or homolog thereof) inactivated, wherein such genetic inactivation results in increased heterologous protein expression by the fungi. Such fungi are referred to herein as ΔmstC fungi. It is shown herein that genetic inactivation of mstC results in *Aspergillus* fungi increases heterologous protein production in the fungi as compared to *Aspergillus* having a native mstC sequence, such as an increase of at least 2-fold, at least 3-fold, or at least 4-fold.

Contemplated herein are isolated fungi containing a genetic inactivation (e.g., functional deletion) of a mstC gene or homolog thereof. Any fungus can be used, such as Eurotiomycetes (e.g., *Aspergillus*) or Sordariomycetes (e.g., *Neurospora*). In particular examples, the disclosed *Aspergillus* fungus is *A. niger*, such as *Aspergillus niger* strain 11414 (American Type Culture Collection (ATCC) No. 11414; NRRL 2270); or 11414KusA-. In other specific examples, the *Aspergillus* *A. aculeatus, A. awamori, A.* brasiliensis, A. carbonarius, A. flavus, A. foetidus, A. fumigatus, A. furnigatus, A. nidulans, A. niger, A. oryzae, A. pseudoterreus, A. sojae, A. terreus, A. tubingensis, and A. wentii. In particular examples, the ΔmstC fungi is N. crassa, and the gene genetically inactivated is NCU01633.

Any method for genetic inactivation can be used, as long as the expression of the mstC gene is significantly reduced or eliminated, or the function of the expressed mstC protein is significantly reduced or eliminated, such as knocked out (or otherwise made inoperative). For example, the mstC gene can be manipulated to include one or more nucleotide substitutions, insertions, deletions, or combinations thereof, which result in inactivation of the gene. In particular examples, the mstC gene is genetically inactivated by a complete or partial deletion mutation, by insertional mutation, or both. In some examples, the mstC gene is genetically inactivated by the introduction of a stop codon, thereby disrupting expression of the protein.

In some examples, genetic inactivation need not be 100% genetic inactivation. In some embodiments, genetic inactivation refers to at least 50%, at least 60%, at least 70%, at least 80%, at least 90%, or at least 95% gene or protein inactivation. The term "reduced" or "decreased" as used herein with respect to a particular gene or protein activity refers to a lower level of activity than that measured in a comparable cell of the same species. For example, a particular fungi lacking mstC activity has reduced mstC activity if a comparable fungi not having an mstC genetic inactivation has detectable mstC activity. mstC sequences are disclosed herein and others are publicly available, for example from GenBank or EMBL. In some examples, the mstC gene genetically inactivated includes a nucleic acid molecule having at least 80%, at least 90%, at least 95%, at least 97%, at least 98%, at least 99%, or 100% sequence identity to SEQ ID NO: 1 or 3 or to nt 82 to 1764 of SEQ ID NO: 1 prior to the inactivation. In some examples, the mstC gene genetically inactivated encodes a protein comprising at least 80%, at least 90%, at least 95%, at least 97%, at least 98%, at least 99%, or 100% sequence identity to SEQ ID NO: 2 prior to the inactivation.

In some examples, the mstC homolog NCU01633 is genetically inactivated, such as nucleic acid molecule having at least 95%, at least 98%, at least 99%, or 100% sequence identity to SEQ ID NO: 9 or 10 or to nt 652 to 2250 of SEQ ID NO: 10 (e.g., prior to its inactivation). In some examples, the NCU01633 gene that is genetically inactivated encoded a protein comprising at least 95%, at least 98%, at least 99%, or 100% amino acid sequence identity to SEQ ID NO: 11 (e.g., prior to its inactivation).

The disclosed ΔmstC fungi can further include a glucoamylase promoter (such as the fungi's native glucoamylase promoter) operably linked to one or more heterologous proteins. Exemplary heterologous proteins (e.g., a protein not native or naturally occurring in the fungus), such as BG, are provided herein (e.g., see Table 1). Such a recombinant fungi can be used to increase expression of the heterologous protein, such as beta-glucosidase, by the fungi. An exemplary glucoamylase promoter sequence is shown in SEQ ID NO: 8. However, variants of such sequences can be used, including those having at least 80%, at least 90%, at least 95%, at least 96%, at least 97%, at least 98%, or at least 99% sequence identity to SEQ ID NO: 8.

The disclosed ΔmstC gene can further include mutations (such as one or more nucleotide substitutions, insertions, deletions, or combinations thereof) which reduce the activity of in one or more other genes, such as creA and/or amyR. In some embodiments, mutations in the creA gene and/or amyR gene have a synergistic effect in combination with the genetic inactivation of mstC resulting in Aspergillus fungi that have increased heterologous protein production as compared to Aspergillus having a native mstC, creA and amyR sequence. In particular examples, the mutation(s) decrease creA and/or amyR activity by at least 50%, at least 60%, at least 70%, at least 80%, at least 90%, or at least 95%. The term "reduced" or "decreased" as used herein with respect to a cell and a particular gene or protein activity refers to a lower level of activity than that measured in a comparable cell of the same species. For example, a particular fungi having decreased creA and/or amyR activity has reduced creA and/or amyR activity if a comparable fungi not having a creA and/or amyR genetic mutation has detectable creA/amyR activity. In some examples, the amyR gene mutated includes a nucleic acid molecule having at least 80%, at least 90%, at least 95%, at least 97%, at least 98%, at least 99%, or 100% sequence identity to SEQ ID NO: 4 (or to nt join (1 . . . 980,1032 . . . 1482,1541 . . . 1849)) prior to the mutation. In some examples, the amyR gene mutated encodes a protein comprising at least 80%, at least 90%, at least 95%, at least 97%, at least 98%, at least 99%, or 100% sequence identity to SEQ ID NO: 5 (or to nt join ) prior to the mutation. In some examples, the creA gene mutated includes a nucleic acid molecule having at least 80%, at least 90%, at least 95%, at least 97%, at least 98%, at least 99%, or 100% sequence identity to SEQ ID NO: 6 or nt 1339 to 2622 of SEQ ID NO: 6, prior to the mutation. In some examples, the creA gene mutated encodes a protein comprising at least 80%, at least 90%, at least 95%, at least 97%, at least 98%, at least 99%, or 100% sequence identity to SEQ ID NO: 7 prior to the mutation.

A. Methods of Functionally Deleting Genes

As used herein, an "inactivated" or "functionally deleted" gene means that the gene has been mutated, for example by insertion, deletion, or substitution (or combinations thereof) of one or more nucleotides such that the mutation substantially reduces (and in some cases abolishes) expression or biological activity of the encoded gene product. The mutation can act through affecting transcription or translation of the gene or its mRNA, or the mutation can affect the polypeptide product itself in such a way as to render it substantially inactive.

Genetic inactivation of one or more genes (can be referred to as functional deletion) can be performed using any conventional method. In one example, a strain of Aspergillus or other fungus is transformed with a vector which has the effect of down-regulating or otherwise inactivating an mstC gene or homolog thereof. For example, control elements such as promoters and the like which control gene expression can be mutated, the coding region of the gene can be mutated so that any protein expressed is substantially inactive, or the mstC gene or homolog thereof can be deleted entirely. For example, an mstC gene or homolog thereof can be functionally deleted by complete or partial deletion mutation (for example by deleting a portion of the coding region of the gene), by insertional mutation (for example by inserting nucleotides into the coding region of the gene, such as a molecule of about 1-5000 nucleotides), or combinations thereof. Thus, the disclosure in some examples provides transformed or recombinant fungi that include at least one exogenous nucleic acid molecule which genetically inactivates an mstC gene (such as mutates the nucleic acid sequence of SEQ ID NO: 1 or 3) or a homolog thereof (such as mutates the nucleic acid sequence of SEQ ID NO: 9 or 10). In one example, such a transformed fungus produces increased amounts of a heterologous protein, for example relative to a comparable fungus with a native, non-mutated mstC sequence or homolog thereof.

In one example, an insertional mutation includes introduction of a nucleic acid molecule that is in multiples of three bases (e.g., a sequence of 3, 9, 12, or 15 nucleotides) to reduce the possibility that the insertion will affect downstream genes. Mutations can also be generated through insertion of a foreign gene sequence, for example the insertion of a gene encoding antibiotic resistance (such as hygromycin or bleomycin) into the mstC gene or homolog thereof.

In one example, genetic inactivation is achieved by deletion of a portion of the coding region of the mstC gene or homolog thereof. For example, some, most (such as at least 50%) or virtually the entire coding region can be deleted. In particular examples, about 5% to about 100% of the gene is deleted, such as at least 20% of the gene, at least 40% of the gene, at least 75% of the gene, or at least 90% of the mstC gene. In particular examples, about 5% to about 100% of the coding region is deleted, such as at least 20% of the coding region, at least 40% of the coding region, at least 75% of the coding region, or at least 90% of the mstC coding region (e.g., the coding region of shown in SEQ ID NO: 1, namely nt 82 to 1764 of SEQ ID NO: 1, or the coding region of shown in SEQ ID NO: 10, namely nt 652 to 2250 of SEQ ID NO: 10).

In one example, allelic exchange is employed to genetically inactivate one or more genes, such as mstC, in *Aspergillus*, or NCU01633 in *Neurospora*.

In one example, counterselectable markers (such as pyrG) are employed (e.g., see Reyrat et al., *Infec. Immun.* 66:4011-4017, 1998). In this technique, a double selection strategy is employed wherein a plasmid is constructed encoding both a selectable and counterselectable marker, with flanking DNA sequences derived from both sides of the desired deletion. The selectable marker is used to select for fungi in which the plasmid has integrated into the genome in the appropriate location and manner. The counterselecteable marker is used to select for the very small percentage of fungi that have spontaneously eliminated the integrated plasmid. A fraction of these fungi will then contain only the desired deletion with no other foreign DNA present.

In another technique, the cre-lox system is used for site specific recombination of DNA (for example see Steiger et al., *Appl. Environ. Microbiol.* 77(1): 114, 2011). The system includes 34 base pair lox sequences that are recognized by the bacterial cre recombinase gene. If the lox sites are present in the DNA in an appropriate orientation, DNA flanked by the lox sites will be excised by the cre recombinase, resulting in the deletion of all sequences except for one remaining copy of the lox sequence. Using recombination techniques, the targeted gene (e.g., mstC or homolog thereof) can be deleted in the *Aspergillus* genome and replaced with a selectable marker (for example a gene coding for kanamycin or other antibiotic resistance) that is flanked by the lox sites. Transient expression (e.g., by electroporation of a suicide plasmid containing the cre gene under control of a promoter that functions in *Aspergillus* or other fungus) of the cre recombinase efficiently eliminates the lox flanked marker. This process can produce a mutant fungi containing the desired deletion mutation of mstC or homolog thereof and one copy of the lox sequence.

In another example, an mstC gene sequence (or homolog thereof) in a fungal genome is replaced with a marker gene, such as one encoding for green fluorescent protein, j3-galactosidase, or luciferase. In this technique, DNA segments flanking a desired deletion are prepared by PCR and cloned into a suicide (non-replicating) vector for the fungus. An expression cassette, containing a promoter active in the fungus and the appropriate marker gene, is cloned between the flanking sequences. The plasmid is introduced into wild-type fungi. Fungi that incorporate and express the marker gene are isolated and examined for the appropriate recombination event (replacement of the wild type mstC gene with the marker gene).

Thus, for example, a fungal cell can be engineered to have a disrupted mstC gene (or homolog thereof) using mutagenesis or knock-out technology. (Methods in Yeast Genetics (1997 edition), Adams, Gottschling, Kaiser, and Sterns, Cold Spring Harbor Press, 1998; Datsenko and Wanner, *Proc. Natl. Acad. Sci. USA* 97: 6640-5, 2000; and Dai et al., *Appl. Environ. Microbiol.* 70(4):2474-85, 2004).

In another example, antisense technology is used to reduce or eliminate the activity of mstC (or homolog thereof). For example, a fungal cell can be engineered to contain a cDNA that encodes an antisense molecule that prevents mstC from being translated. The term "antisense molecule" encompasses any nucleic acid molecule or nucleic acid analog (e.g., peptide nucleic acids) that contains a sequence that corresponds to the coding strand of an endogenous mstC gene (or homolog thereof). An antisense molecule also can have flanking sequences (e.g., regulatory sequences). Thus, antisense molecules can be ribozymes or antisense oligonucleotides. A ribozyme can have any general structure including, without limitation, hairpin, hammerhead, or axehead structures, provided the molecule cleaves RNA. Further, gene silencing can be used to reduce the activity of mstC.

Any method can be used to introduce an exogenous nucleic acid molecule into a fungal cell, for example to genetically inactivate mstC (or homolog thereof). For example, chemical mediated-protoplast transformation, electroporation, *Agrobacterium*-mediated transformation, fusion of protoplasts, and biolistic delivery are common methods for introducing nucleic acid into fungal cells. (See, e.g., Ito et al., *J. Bacterol.* 153:163-8, 1983; Durrens et al., *Curr. Genet.* 18:7-12, 1990; Sambrook et al., *Molecular cloning: A laboratory manual*, Cold Spring Harbour Laboratory Press, New York, USA, third edition, 2001; and Becker and Guarente, Methods in Enzymology 194:182-7, 1991). An exogenous nucleic acid molecule contained within a particular cell of the disclosure can be maintained within that cell in any form. For example, exogenous nucleic acid molecules can be integrated into the genome of the cell or maintained in an episomal state. That is, the recombinant fungi cells can be a stable or transient transformant.

B. Measuring Gene Inactivation

A fungus having an inactivated mstC gene (or homolog thereof) can be identified using any known method. For example, PCR and nucleic acid hybridization techniques, such as Northern and Southern analysis, can be used to confirm that a fungus has an inactivated mstC gene (or homolog thereof). Alternatively, real-time reverse transcription PCR (qRT-PCR) can be used for detection and quantification of targeted messenger RNA, such as mRNA of mstC gene (or homolog thereof) in the parent and mutant strains as grown at the same culture conditions. Immunohistochemical and biochemical techniques can also be used to determine if a cell expresses mstC (or homolog thereof) by detecting the expression of the mstC protein (or homolog thereof) encoded by mstC (or homolog thereof). For example, an antibody having specificity for mstC (or homolog thereof) can be used to determine whether or not a particular fungus contains a functional nucleic acid encoding mstC protein (or homolog thereof). Further, biochemical techniques can be used to determine if a cell contains a particular gene inactivation by detecting a product produced as a result of the expression of the peptide.

C. Measuring Heterologous Protein Activity

Methods of determining whether a genetic inactivation of mstC (or homolog thereof) in a fungus increases heterologous protein (e.g., beta-glucosidase, glycoside hydrolase, carbohydrates esterase, protease, lipase, liginase, cellulases, and hemicellulose, and others provided in Table 1) production, for example relative to the same strain with a native mstC sequence (or homolog thereof) (such as a parental strain), are routine. Although particular examples are disclosed herein, the methods are not limiting. For example, immunohisto-chemical and biochemical techniques (such as ELISA, flow cytometry, western blotting, and fluorescence microscopy) can be used to measure or detect heterologous protein expression in A mstC fungi.

In one example, production of beta-glucosidase by a fungus, such as *Aspergillus* (such as an ΔmstC strain) can be measured using a spectrophotometric assay. In one example beta-glucosidase production can be measured using a pNPG as explained in Example 1 (also see Aich et al. (2001). Expression and Purification of *Escherichia coli* β-Glucuronidase. Protein expression and purification, 22(1), 75-8.

D. mstC Sequences mstC protein and nucleic acid sequences are publicly available and specific examples are provided herein. In addition, mstC sequences, as well as the sequences of homologs thereof, can be identified using routine molecular biology methods.

An exemplary mstC nucleic acid sequence that can be genetically inactivated is shown in SEQ ID NO: 1, 3, and nt 82 to 1764 of SEQ ID NO: 1, and exemplary NCU01633 nucleic acid sequence that can be genetically inactivated is shown in SEQ ID NOS: 9, 10, and nt 652 to 2250 of SEQ ID NO: 10. However, variants of SEQ ID NO: 1 or 3 that encode a functional mstC protein, or variants of SEQ ID NO: 9 or 10 that encode a functional NCU01633 protein, can be genetically inactivated. Variant sequences may contain a single insertion, a single deletion, a single substitution, multiple insertions, multiple deletions, multiple substitutions, or any combination thereof (e.g., single deletion together with multiple insertions). In addition, the degeneracy of the code permits multiple nucleic acid sequences to encode the same protein. In some examples, the mstC gene that is genetically inactivated includes a nucleic acid molecule having at least 80%, at least 90%, at least 95%, at least 97%, at least 98%, at least 99%, or 100% sequence identity to SEQ ID NO: 1 or 3 or nt 82 to 1764 of SEQ ID NO: 1 prior to the inactivation. In some examples, the NCU01633 gene that is genetically inactivated includes a nucleic acid molecule having at least 80%, at least 90%, at least 95%, at least 97%, at least 98%, at least 99%, or 100% sequence identity to SEQ ID NO: 9, 10, or nt 652 to 2250 of SEQ ID NO: 10, prior to the inactivation.

An exemplary mstC protein sequence is shown in SEQ ID NO: 2. However, mstC sequences that encode variants of SEQ ID NO: 2 and have mstC activity, can be genetically inactivated. Variant mstC protein sequences may contain a one or more amino acid insertions, deletions, substitutions, or any combination thereof. In some examples, a native mstC protein has at least 80%, at least 90%, at least 95%, at least 97%, at least 98%, at least 99%, or 100% sequence identity to SEQ ID NO: 2 prior to the inactivation.

An exemplary NCU01633 protein sequence is shown in SEQ ID NO: 11. However, NCU01633 sequences that encode variants of SEQ ID NO: 11 and have NCU01633 activity, can be genetically inactivated. Variant NCU01633 protein sequences may contain a one or more amino acid insertions, deletions, substitutions, or any combination thereof. In some examples, a native NCU01633 protein has at least 80%, at least 90%, at least 95%, at least 97%, at least 98%, at least 99%, or 100% sequence identity to SEQ ID NO: 11 prior to the inactivation.

Additional mstC sequences (and homologs thereof) can be identified using any method such as those described herein. For example, mstC nucleic acid molecules (and homologs thereof) that encode an mstC protein can be identified and obtained using molecular cloning or chemical nucleic acid synthesis procedures and techniques, including PCR. In addition, nucleic acid sequencing techniques and software programs that translate nucleic acid sequences into amino acid sequences based on the genetic code can be used to determine whether or not a particular nucleic acid has any sequence homology with known mstC sequences. Sequence alignment software such as MEGALIGN (DNASTAR, Madison, Wis., 1997) can be used to compare various sequences.

Nucleic acid hybridization techniques can be used to identify and obtain a nucleic acid molecule that encodes an mstC protein. Briefly, any known mstC nucleic acid molecule, or fragment thereof, can be used as a probe to identify similar nucleic acid molecules (including homologs thereof) by hybridization under conditions of moderate to high stringency. Such similar nucleic acid molecules then can be isolated, sequenced, and analyzed to determine whether the encoded protein is an mstC protein.

IV. Expressing Heterologous Proteins in a mstC Fungi from a Glucoamylase Promoter The isolated fungi having an inactivated mstC gene, and a glucoamylase promoter operably linked to one or more heterologous proteins, can be used to express the heterologous protein(s). In some embodiments, the expressed heterologous protein is a heterologous enzyme (e.g., beta-glucosidase or other enzyme or protein in Table 1). Exemplary heterologous protein(s) are provided herein, and include those used that can be used to degrade a biomass. In some embodiments, the expressed heterologous protein is a heterologous fungal protein, or heterologous bacterial (e.g., *E. coli*) protein.

The methods include by culturing or growing recombinant fungi under conditions that permit the fungi to express the heterologous protein. For example, the recombinant fungus can be grown or cultured in an appropriate culture medium containing the appropriate nutrients and ions, at an appropriate temperature and pH. In some examples, the expression of the heterologous protein in the ΔmstC mutant strain is increased at least two-fold (such as at least 3-fold, or at least 4-fold) compared to the expression of the heterologous enzyme in a WT fungus (e.g., one having a native mstC gene).

In some examples, the method includes isolating or collecting the heterologous protein expressed by the recombinant fungus, for example from the fungi or from the culture media in which the fungi are grown.

V. Method of Biomass Degradation

Methods of using the ΔmstC fungi that include a glucoamylase promoter operably linked to one or more heterologous protein coding sequences to degrade a biomass (such as a lignocellulose biomass) are provided. Lignocellulose biomass includes carbohydrate polymers such as cellulose and hemicellulose. These carbohydrate polymers contain various sugar molecules and they are bound to lignin, an aromatic polymer. Cellulolytic enzymes degrade the lignocellulose biomass by breaking down the biomass into its constituent monomers and oligomers. Disclosed herein is a method of degrading such biomass by expressing one or more cellulolytic enzymes (e.g., beta-glucosidase) in the disclosed ΔmstC fungi that include a glucoamylase promoter operably linked to one or more heterologous protein coding sequences.

For example, the method can include incubating a biomass with ΔmstC fungi that include a glucoamylase promoter operably linked to a heterologous protein, such as a protein that can be used to degrade the biomass (e.g., BG or other enzyme or protein listed in Table 1, as well as combinations thereof), under conditions that permit the fungus to express the heterologous protein from the glucoamylase promoter, thereby degrading the biomass. For example, the biomass can be incubated with the recombinant fungus can be in an appropriate medium, at an appropriate temperature and pH. In some example, the incubation occurs in a fermenter. Expression of the heterologous protein from the glucoamylase promoter degrades the biomass. In some examples, the expression of the heterologous protein in the ΔmstC mutant strain is increased at least two-fold (such as at least 3-fold, or at least 4-fold) compared to the expression of the heterologous enzyme in a WT fungus (e.g., one having a native mstC gene).

In other examples, the method can include incubating a biomass with one or more heterologous proteins (e.g., BG or other enzyme or protein listed in Table 1, as well as combinations thereof) obtained from the ΔmstC fungi that include a glucoamylase promoter operably linked to a heterologous protein (for example enzymes secreted in the growth media of the mutant fungi and separated, collected or otherwise isolated), such as one or more heterologous proteins that can be used to degrade the biomass, under conditions that permit the secreted heterologous protein to degrade the biomass. For example, the biomass can be incubated with the one or more heterologous proteins in an appropriate liquid material, at an appropriate temperature and pH. In some example, the incubation occurs in a fermenter. The heterologous protein(s) obtained from the ΔmstC fungi degrade the biomass. Thus, in some examples, the method can also include culturing the ΔmstC fungi and separating or isolating the heterologous protein(s) expressed in and secreted by the ΔmstC mutant strain, and then adding the separated heterologous protein(s) to the biomass.

In some embodiments, the biomass is further incubated with ionic liquids (ILs), such as 1-ethyl-3-methylimidazolium acetate ([C$_2$mim]OAc), for example before, during, or after incubation with the ΔmstC fungi or separated heterologous protein(s). In some examples, the amount of IL is at least 1% v/v, at least 2% v/v, at least 4% v/v, at least 5% v/v, at least 10% v/v, or at least 15% v/v (such as about 1% v/v, about 2% v/v, about 3% v/v, about 4% v/v, about 5% v/v, about 6% v/v, about 7% v/v, about 8% v/v, about 9% v/v, or about 10% v/v).

In some examples, the biomass is pretreated with the IL, and subsequently incubated with the disclosed recombinant fungi or separated heterologous protein(s). Therefore, if pretreated with IL, IL-tolerance is needed for the cellulolytic enzyme to be effective in biomass degradation. The disclosed fungi have IL-tolerance.

VI. Glucoamylase Expression with ΔmstC Fungi

Provided herein are methods of increasing glucoamylase production using the disclosed ΔmstC fungi. In some examples, expression of the glucoamylase in ΔmstC fungi (such as an *Aspergillus* species, such as *A. niger*, or a *Neurospora* species, such as *N. crassa*) is increased at least two-fold (such as at least 3-fold, or at least 4-fold) compared to the expression of the glucoamylase in a WT fungus (e.g., one having a native mstC gene). In some examples, if a *Neurospora* species is used, the nearest homolog to mstC, NCU01633, is genetically inactivated.

The methods include culturing or growing ΔmstC fungi under conditions that permit the fungi to express the native glucoamylase protein. For example, the ΔmstC fungus can be grown or cultured in an appropriate culture medium containing the appropriate nutrients and ions, at an appropriate temperature and pH.

The following examples are provided to illustrate certain particular features and/or embodiments. These examples should not be construed to limit the disclosure to the particular features or embodiments described.

Example 1

Materials and Methods

This example describes methods used in the experiments described in Examples 2-4 below.

Reagents and Strains.

Unless otherwise indicated, all reagents were obtained from Sigma (St. Louis, Mo.). *Aspergillus niger* strains used are listed in Table 2. For general maintenance, *A. niger* strains were cultured on slants of Potato/Dextrose (PD) agar and incubated at 30° C. for 3 days to allow for hyphal growth and spore formation. Information on *Neurospora* strains can be found in Colot et al. (*PNAS*, 103:10352-7, 2006).

TABLE 2 strains used

| Name | Genotype | Source |
|---|---|---|
| WT | 11414 | ATCC |
| GFP | 11414 P$_{glaA}$-GFP-T$_{trpC}$/hphA | Campen et al. |
| J03 | 11414 P$_{glaA}$-J03-T$_{trpC}$/hphA | Campen et al. |
| J03 ΔmstC | 11414 P$_{glaA}$-J03-T$_{trpC}$/hphA ΔmstC/ptrA | This study |
| 11414 pyrG$^-$ | 11414 pyrG$^-$ | Chiang et al. 2011 |
| ΔglaA/P$_{glaA}$-A5 | 11414 pyrG$^-$ ΔkusA/AfpyrG ΔglaA/P$_{glaA}$-A5IL97-T$_{trpC}$/hphA | Campen et al. |

TABLE 2-continued strains used

| Name | Genotype | Source |
|---|---|---|
| ΔglaA/PgpdA-A5 | 11414 pyrG⁻ ΔkusA/AfpyrG ΔglaA/P$_{gpdA}$-A5IL97-T$_{trpC}$/hphA | Campen et al. |
| ΔglaA/Pecm33-A5 | 11414 pyrG⁻ ΔkusA/AfpyrG ΔglaA/P$_{ecm33}$-A5IL97-T$_{trpC}$/hphA | Campen et al. |
| ΔglaA/P$_{glaA}$-A5 ΔmstC | 11414 pyrG⁻ ΔkusA/AfpyrG ΔglaA/P$_{glaA}$-A5IL97-T$_{trpC}$/hphA ΔmstC/ptrA | This study |
| ΔglaA/PgpdA-A5 ΔmstC | 11414 pyrG⁻ ΔkusA/AfpyrG ΔglaA/P$_{gpdA}$-A5IL97-T$_{trpC}$/hphA ΔmstC/ptrA | This study |
| ΔglaA/Pecm33-A5 ΔmstC | 11414 pyrG⁻ ΔkusA/AfpyrG ΔglaA/P$_{ecm33}$-A5IL97-T$_{trpC}$/hphA ΔmstC/ptrA | This study |

The J03 strain was generated when 11414 (from the American Type Culture Collection; Manassas, Va.) was transformed with vector containing a codon-optimized sequence for a beta-glucosidase (BG) from Thermobaculum terrenum (J03) (Gladden et al. 2014), driven by the A. niger glucoamylase promoter (P$_{glaA}$) and followed by the A. nidulans tryptophan biosynthesis terminator (T$_{trpC}$) (the expression construct is detailed in Campen et al.). A similar plasmid expressing the green fluorescent protein (GFP) in place of the J03 sequence was used to produce the strain GFP.

The construction of strains with a BG from Thermotoga petrophila (A5) (Park et al. 2012) under the control of various promotors is detailed in Campen et al. Briefly, the Aspergillus fumigatus pyrG (AfpyrG) was used to replace the native kusA locus in a 11414 pyrG-strain (Chiang et al. 2011). This strain was subsequently transformed with a vector containing the P$_{glaA}$-A5-T$_{trpC}$ construct described above flanked by 1 kb of sequence 5' and 3' to the native glaA locus, allowing for targeted integration. In variations of this procedure, the A5 sequence was preceded by promoter sequences from either the A. niger glyceraldehyde-3-phosphate dehydrogenase or extracellular matrix loci (P$_{gpdA}$ or P$_{ecm33}$, respectively).

Generation of the mstC sugar transporter deletion strains—ΔmstC, ΔglaA/P$_{glaA}$-A5 ΔmstC, ΔglaA/Ppde-A5 ΔmstC, and ΔglaA/P$_{ecm33}$-A5 ΔmstC strains—is described below.

Mutagenesis and Primary Plate Screening.

Spores were harvested from PD agar slant tubes of J03 using a sterile solution of 0.02% (v/v) Tween-20. In a final volume of 0.5 mL, the spores were combined with 400 ng/mL 4-nitroquinoline 1-oxide (4-NQO; concentration empirically determined to result in a ~90% kill rate) and incubated on a shaker set at 200 rpm at 37° C. for 30 min. An equal volume of 5% (v/v) sodium thiosulfate was added to inactivate the 4-NQO before plating the spores on BG Screening agar (20 g peptone, 8 g ammonium sulfate, 10 g ox-bile, and 15 g agar were added to 800 mL ddH$_2$O and autoclaved; after autoclaving, 200 mL of a sterile 50% (w/v) maltose solution, 1 g esculin dissolved in methanol, and 5 mL of a sterile 10% (w/v) ferric citrate solution was added). The plates were incubated at 30° C. for 3 days before evaluating the halos around the colonies in comparison with colonies from untreated J03 spores. Mutated colonies with increased halos compared to the parent were picked and transferred to slants of PD agar.

Secondary Liquid Culture Screening.

To evaluate the BG production of the A. niger mutant strains in liquid culture, 1×10⁶ spores/mL were first inoculated into 5 mL of CSL Medium (100 g corn steep liquor (50% (w/v) solids), 50 g fructose, 10 g glucose, 1 g sodium phosphate, 0.5 g magnesium sulfate, and 0.05 ml Antifoam 204 were added to 760 mL ddH$_2$O, the pH adjusted to 5.8, and autoclaved; after autoclaving, 240 mL of a sterile 50% (w/v) maltose solution was added) in 60-mL glass culture tubes. The tubes were incubated in a shaker set at 200 rpm at 30° C. for 48 hr to generate fungal biomass. An aliquot of 0.5 mL of culture was then transferred into 5 mL of HMM Medium (120 g maltose, 70 g sodium citrate (tribasic dihydrate), 15 g ammonium sulfate, 1 g sodium phosphate, 1 g magnesium sulfate (anhydrous), and 3 g SC Complete Media (Sunrise Science; San Diego, Calif.)) were added to 1 L ddH$_2$O, the pH adjusted to 6.2, and filter-sterilized) in 60-mL glass culture tubes. The tubes were incubated in a shaker set at 200 rpm at 30° C. for 120 hr. Cell-free aliquots of the resulting culture supernatants were harvested using a 0.45 μm nylon centrifugal filter (VWR; Radnor, Pa.).

Aliquots from the culture supernatants were assayed for total secreted protein using the Bradford Protein Assay Kit (Bio-Rad; Hercules, Calif.). The BG activity in each sample was evaluated by combining 10 μL of culture supernatant with 90 μL of reaction mix (80 mM MES buffer (pH 6.5), 5 mM 4-nitrophenyl 3-D-glucopyranoside (pNPG), plus or minus 10% (v/v) of the ionic liquid 1-ethyl-3-methylimidazolium acetate ([C$_2$mim]OAc)). The reactions were incubated at 65° C. for 30 min before being quenched with 100 μL 2% (w/v) sodium carbonate. The absorbance of 100 μL aliquots of the pNPG reactions was read at 410 nm.

Characterization of Mutant Strains.

A. niger strains were first inoculated at 1×10⁶ spores/mL into 50 mL CSL medium in 250-mL glass flasks and then sub-cultured at 5 mL into 50 mL HMM medium in 250-mL glass flasks in triplicate for each strain. Cell-free samples of the resulting culture supernatants were harvested and assayed for total protein and BG activity as outlined above. In addition, the fungal biomass from each culture was harvested by decanting the culture through a single layer of Miracloth (EMD Millipore; Billerica, Mass.), pressing away the moisture, and then lyophilizing before weighing.

Sequencing and Bioinformatics Analyses of Mutants.

Genomic DNA was prepared for sequencing by grinding ~0.5 g lyophilized fungal biomass to a fine powder and combining it with 15 mL CTAB buffer (2% (w/v) hexadecyltrimethylammonium bromide, 100 mM Tris-HCl (pH 8), 20 mM EDTA (pH 8), and 1.4 M NaCl); the sample was vortexed to mix and then incubated at 57° C. for 2 hr with occasional vortexing. An equal volume 25:24:1 phenol:chloroform:isoamyl alcohol was added to the sample, vortexed to mix, and then centrifuged at 4° C. for 10 min at 10,000 rcf. The resulting supernatant was extracted a second time with 5 mL 25:24:1 phenol:chloroform:isoamyl alcohol. Nucleic acids were precipitated by adding one volume 2-propanol to the resulting supernatant and centrifuging at 4° C. for 10 min at 4,500 rcf. The resulting pellet was washed with 70% (v/v) ethanol, allowed to air-dry, and then incubated at 65° C. in 1 mL sterile ddH2O to resuspend. To remove RNA, 2 μL 200 mg/mL RNase A (Thermo Fisher Scientific; Waltham, Mass.) was added and the sample incubated at 37° C. for 2 hr. The sample was extracted a final time with 1 mL 25:24:1 phenol:chloroform:isoamyl alcohol and the DNA precipitated with the same 2-propanol and 70% (v/v) ethanol method as above before resuspending in 0.5 mL sterile ddH$_2$O.

DNA libraries were produced at the Joint Genome Institute (JGI) and sequenced by the Illumina paired-end sequencing method using MiSeq 2×150 bp (~30× coverage) or HiSeq 2×100 bp (~100× coverage). The sequence data have been deposited with the NCBI BioProject database under the following accession numbers: PRJNA249619 (J03), PRJNA249388 (J03 1.1), PRJNA249608 (J03 1.2), PRJNA249607 (J03 1.6), PRJNA249612 (J03 1.7), PRJNA249480 (J03 1.10), PRJNA249613 (J03 2.8), PRJNA249614 (J03 4.3), PRJNA259122 (J03 6.3), PRJNA259125 (J03 7.2), PRJNA259124 (J03 7.4), PRJNA259128 (J03 8.2), and PRJNA259127 (J03 8.3). The sequenced reads were mapped to the reference genome sequence of *A. niger* strain ATCC 1015 v4.0, augmented with the sequence of the transformation plasmid containing J03, using BWA-MEM (Li 2014). Mapped reads were sorted by coordinate using SAMtools (Li et al. 2009) and duplicate reads were marked using Picard Tools.

Variant calling for single nucleotide polymorphisms and insertions/deletions was performed using a combination of BCFtools (Li 2011) or GATK tools (McKenna et al. 2010). Using BCFtools, variants calling and genotyping were done for each chromosome using multiple samples and merged. Using GATK, variants were called for each sample by GATK HaplotypeCaller and joint genotyping of multiple samples was performed using GATK GenotypeGVCFs. Variants called by BCFtools were filtered using VCFtools, and variants called by GATK were filtered using GATK VariantFiltration. Filtered variants were annotated using the VariantAnnotation package in R (Obenchain et al. 2014). Structural variations such as insertion, deletion, or duplication of relatively large segments were identified using Pindel (Ye et al. 2009), BreakDancer (Chen et al. 2009), Delly (Rausch et al. 2012), or Lumpy (Layer et al. 2014).

Deletion of Sugar Transporter.

For targeted deletion of the MstC sugar transporter, a plasmid containing the *Aspergillus oryzae* pyrithiamine resistance (ptrA) sequence (Kubodera et al. 2000), in a reverse orientation and flanked by ~1 kb sequence upstream and downstream of the mstC locus, was synthesized (GenScript; Piscataway, N.J.). The deletion construct was amplified by PCR and then transformed into the J03, ΔglaA/P$_{glaA}$-A5, ΔglaA/P$_{gpdA}$-A5, and ΔglaA/P$_{ecm33}$-A5 strains similar to the protocol described by Yang et al. (2014). Briefly, 5×10$^5$ spores/mL were inoculated into 100 mL YPD medium in a 250-mL glass flask and incubated in a shaker set at 150 rpm at 30° C. for 16 hr. The culture was filtered through a single layer of sterilized Miracloth: mycelia retained on the Miracloth were thoroughly rinsed with sterile ddH$_2$O and then transferred to a 250-mL glass flask containing 40 mL Protoplasting buffer (0.6 M ammonium sulfate, 50 mM maleic acid, and 30 mg/mL VinoTaste Pro (Novozymes; Davis, Calif.) in ddH$_2$O, the pH adjusted to 5.5, and filter-sterilized). The digesting mycelia were incubated in a shaker set at 70 rpm at 30° C. for 4-6 hr. The culture was filtered through a single layer of sterilized Miracloth and the resulting flow-through centrifuged for 10 min at 800 rcf. The resulting pellet was washed twice with 25 mL ST solution (1 M sorbitol in 50 mM Tris (pH 8.0), filter-sterilized) and once with 10 mL STC solution (1 M sorbitol and 50 mM calcium chloride in 50 mM Tris (pH 8.0)), centrifuging for 10 min at 800 rcf. The protoplast pellet was resuspended in STC solution to a concentration of 1.2×10$^7$ protoplasts/mL and then combined with one-quarter volume PEG solution (40% (w/v) polyethylene glycol 4000, 1 M sorbitol, and 50 mM calcium chloride in 50 mM Tris (pH 8.0), filter-sterilized); to this, dimethyl sulfoxide was added at 7% of the final volume. The purified deletion construct PCR product was added at 1-10 μg per 100 μL protoplast suspension and incubated on ice for 15 min; 1 mL PEG solution was added and incubated at room temperature for 15 min. Next, 10 mL Thiamine-minus Sorbitol Medium (10 g/L glucose, Nitrate Salts (6 g/L sodium nitrate, 0.52 g/L potassium chloride, 0.52 g/L magnesium sulfate heptahydrate, and 1.52 g/L potassium dihydrogen phosphate (Pontecorvo 1953)), Trace Elements (2.25 mg/L zinc sulfate heptahydrate, 11 mg/L boric acid, 5 mg/L manganese chloride tetrahydrate, 5 mg/L iron sulfate heptahydrate, 1.7 mg/L cobalt chloride hexahydrate, 1.6 g/L copper sulfate pentahydrate, 0.085 mg/L ammonium molybdate dihydrate, and 50 mg/L tetrasodium ethylenediaminetetraacetic acid (Barrat et al. 1965)), Thiamine-minus Vitamin Stock solution (1 mg/L each of biotin, nicotinic acid, p-aminobenzoic acid, pyridoxine, and riboflavin (Barrat et al. 1965)), and 1 M sorbitol in ddH$_2$O, autoclaved to sterilize) was added and incubated in a shaker set at 80 rpm at 30° C. for 1 hr. The sample was then centrifuged for 15 min at 800 rcf and the resulting pellet resuspended in 12 mL Pyrithiamine Sorbitol agar (10 g/L glucose, Nitrate Salts, Trace Elements, Thiamine-minus Vitamin Stock solution, 1 M sorbitol, 18 g/L agar, and 0.1 μg/mL pyrithiamine hydrobromide in ddH2O, autoclaved to sterilize) before plating; an overlay of 12 mL Pyrithiamine Sorbitol agar was applied and the plate incubated at 30° C. for 3-5 days.

Pyrithiamine-resistant colonies were transferred to PD agar slants. Spores were inoculated into 3 mL Yeast extract/Peptone/Dextrose (YPD) medium in 15-mL culture tubes and incubated in a shaker set at 200 rpm at 30° C. for 2-3 days. Fungal biomass was harvested using a 0.45 μm nylon centrifugal filter and genomic DNA was prepared using the ZR Fungal/Bacterial DNA MiniPrep kit (Zymo Research; Irvine, Calif.). The strains were screened by PCR using primer pairs targeted within and flanking the ΔmstC construct to identify those strains where the ptrA sequence had replaced the mstC locus.

Protein Gel Electrophoresis.

Aliquots of cell-free culture supernatant prepared from CSL medium and HMM medium enzyme induction cultures of *A. niger* were combined with Laemmli sample buffer and heated to 99° C. for 10 min. Samples were then loaded on a 12% or 8-16% gradient Mini-Protean TGX Precast Gel (Bio-Rad; Hercules, Calif.) and run at a constant voltage. Coomassie staining was performed using GelCode Blue Stain Reagent (Thermo Fisher Scientific; Waltham, Mass.).

Example 2

Mutagenesis Screen Using the Strain J03

This example describes a forward mutagenesis screen using the strain J03 to identify loci that could enhance heterologous protein production. Based on these teachings, one skilled in the art will appreciate that mutagenesis screen can be performed in other strains of *Aspergillus*.

Figure 2A:
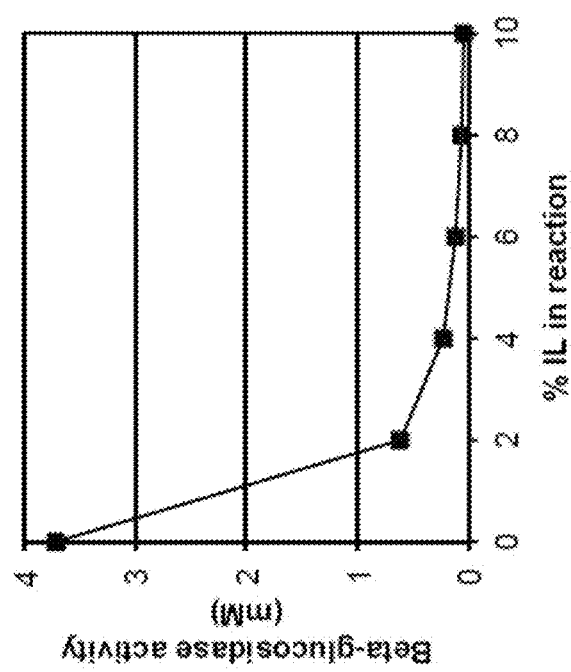
FIG. 2A is a graph showing beta-glucosidase activity (mM) of commercial *A. niger* glucosidase (Sigma 49291, 0.31 mg/mL).
Figure 2B:
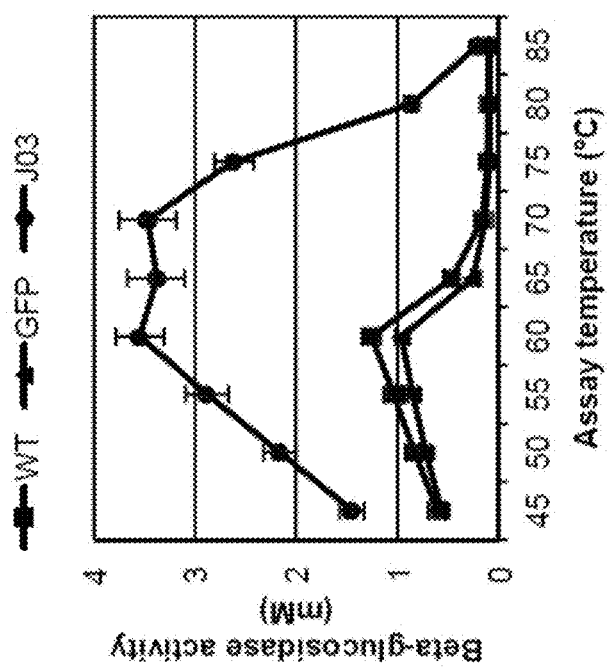
FIG. 2B is a graph showing beta-glucosidase activity (mM) of WT, GFP, and J03 strain across temperature range 45° C. to 85° C. in 5° C. increments.
Figure 2C:
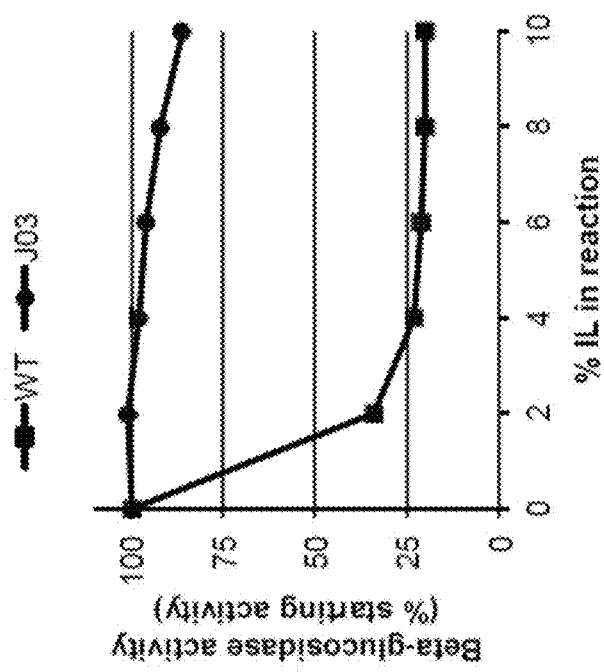
FIG. 2C is a graph showing beta-glucosidase activity (% starting activity) of WT and J03 strain at 65° C. across ionic liquid (IL) range.

The *Aspergillus niger* strain ATCC 11414 (WT) was engineered to produce a beta-glucosidase (BG) from the bacterium *Thermobaculum terrenum*, generating the strain J03. This enzyme was previously identified in a screen for thermophilic cellulose-degrading enzymes capable of functioning in the presence of the ionic liquid (IL) 1-ethyl-3 methylimidazolium acetate ([C2mim][OAc]) (Gladden et al. 2014). The fungal expression construct was designed using enzyme sequence codon-optimized to the genome of *A. niger*, driven by the *A. niger* glucoamylase promoter ($P_{glaA}$) (SEQ ID NO: 8), and followed by a terminator from one of the *Aspergillus nidulans* tryptophan biosynthetic pathway genes ($T_{trpC}$) (Campen et al.). The *A. niger* J03 strain generated BG activity at moderately elevated levels compared to the parent (FIG. 1A) without significant change in the overall amount of protein secreted (FIG. 1B). It was possible to distinguish the activities of any native *A. niger* BG present in the culture supernatant samples from the heterologous bacterial enzyme through the inclusion of IL in the enzymatic assays: while the BG activity of both WT and GFP control strain are reduced to background levels in the presence of IL, the BG activity of the J03 strain is unaffected (FIG. 2C). A forward mutagenesis screen was designed using the J03 strain to identify loci that could enhance heterologous protein production.

Before carrying out the mutagenesis, a plate-based means of detecting secreted BG production was developed. First, a panel of colorimetric and fluorescent substrates was tested, including 5-bromo-4-chloro-3-indolyl β-D-glucopyranoside (X-Glc), esculin in combination with ferric citrate, indoxyl β-D-glucoside, 4-methylumbelliferyl β-D-glucopyranoside (MUGlc), and resorufin β-D-glucopyranoside. Culture supernatant from either J03 or the GFP control strain was spotted onto minimal media plates with these substrates infused into the agar: all but the indoxyl β-D-glucoside was found to allow for halo formation. However, when conidial spores from the same two strains were spread on the plates, only those containing X-Glc or esculin produced halos around the resulting colonies. Next, a solid medium containing high levels of peptone and maltose was found that produced the desired expression of recombinant BG from J03 while repressing the native BG secretion in the WT parent and GFP control strains. Finally, three colony-restricting compounds were tested: the detergent Triton X-100, the IL [C₂mim][OAc], and ox-bile. Triton X-100 was effective in reducing colony size, but not at allowing for distinction between positive and negative (J03 and GFP, respectively) control strains while [C2mim][OAc] did not sufficiently restrict colony size, though it was effective at reducing native BG activity. Ox-bile (1% w/v) was chosen for the mutagenesis screen as it was most effective at limiting colony size while still allowing for clear BG halo formation.

Once a means of screening for BG hyper-secretors was optimized, conidia from the J03 strain were mutagenized using 4-nitroquinoline 1-oxide (4-NQO) to introduce point mutations in the genome and then spread onto plates with esculin, maltose, and ox-bile as detailed in Example 1. The spores were screened for large halo formation around colonies and stocks were made of those colonies with dark halo diameters exceeding that of the J03 parent strain. These strains were subsequently tested for BG activity by growing the strain in first small (5 mL) and then large (50 mL) liquid cultures and testing the supernatant using the substrate p-nitrophenyl-beta-glucopyranoside (pNPG) to confirm the BG hyper-secretion phenotype.

Mutagenesis of conidia from J03 generated 12 mutant strains with consistently increased BG activity relative to the parent strain. These strains were categorized according to their ability to generate native and/or heterologous BG (Table 3). J03-derivative strains that maintained increased BG activity in the presence of 10% (v/v) [C2mim][OAc] were categorized as strains over-producing the heterologous J03 BG (HET) whereas native BG hyper-production mutants showed no IL-tolerance (NAT). Of the twelve mutants, ten had increased J03 enzyme activity while two were native BG hyperproducers (strains J03 4.3 and J03 6.3). Of note were those strains that showed reductions of up to -50% BG activity in the presence of IL but did not reduce the activity to background as seen with the NAT strains. These strains—J03 1.2, J03 2.8, J03 7.4, and J03 8.3—were categorized as containing both elevated native and heterologous BG production (BOTH) relative to the parent. A representative of each phenotypic category is shown in FIGS. 1A-1B.

TABLE 3

Total protein production, beta-glucosidase activity, and helerologous vs native enzyme production of J03-derivative strains

| | Fold secreted total protein[a] | Fold secreted beta-glucosidase activity[b] | Secreted beta-glucosidase activity phenotype[c] |
|---|---|---|---|
| J03 | 1.0 | 1.0 | — |
| J03 1.1 | 2.4 | 5.2 | Heterologous |
| J03 1.2 | 3.7 | 63.3 | Both |
| J03 1.6 | 2.2 | 4.6 | Heterologous |
| J03 1.7 | 1.5 | 3.0 | Heterologous |
| J03 1.10 | 1.0 | 2.0 | Heterologous |
| J03 2.8 | 3.9 | 111.0 | Both |
| J03 4.3 | 3.4 | 98.0 | Native |
| J03 6.3 | 2.4 | 5.2 | Native |
| J03 7.2 | 2.4 | 5.0 | Heterologous |
| J03 7.4 | 4.1 | 95.8 | Both |
| J03 8.2 | 2.4 | 4.3 | Heterologous |
| J03 8.3 | 3.4 | 22.3 | Both |

[a]Secreted total protein was determined using Bradford assay and then normalized to dry weight of fungal biomass
[b]Secreted beta-glucosidase activity was determined using a pNPG assay and then normalized to dry weight of fungal biomass
[c]Secreted beta-glucosidase activity was evaluated in the absence or presence of 10% [C₂mim]OAc. Changes of <10% were considered to be primarily producing the J03 enzyme, the heterologous bacterial BG; changes of >75% were primarily producing native BG of *A. niger*; changes of 30-60% were producing both heterologous and native BG

Example 3

Sequencing of Hyper-Production Mutant Strains

This example describes a method of DNA genomic sequencing in WT, parent J03, and twelve mutant J03-derivative strains to identify genomic legions responsible for hyper-production of heterologous and/or native BG.

Figure 3:
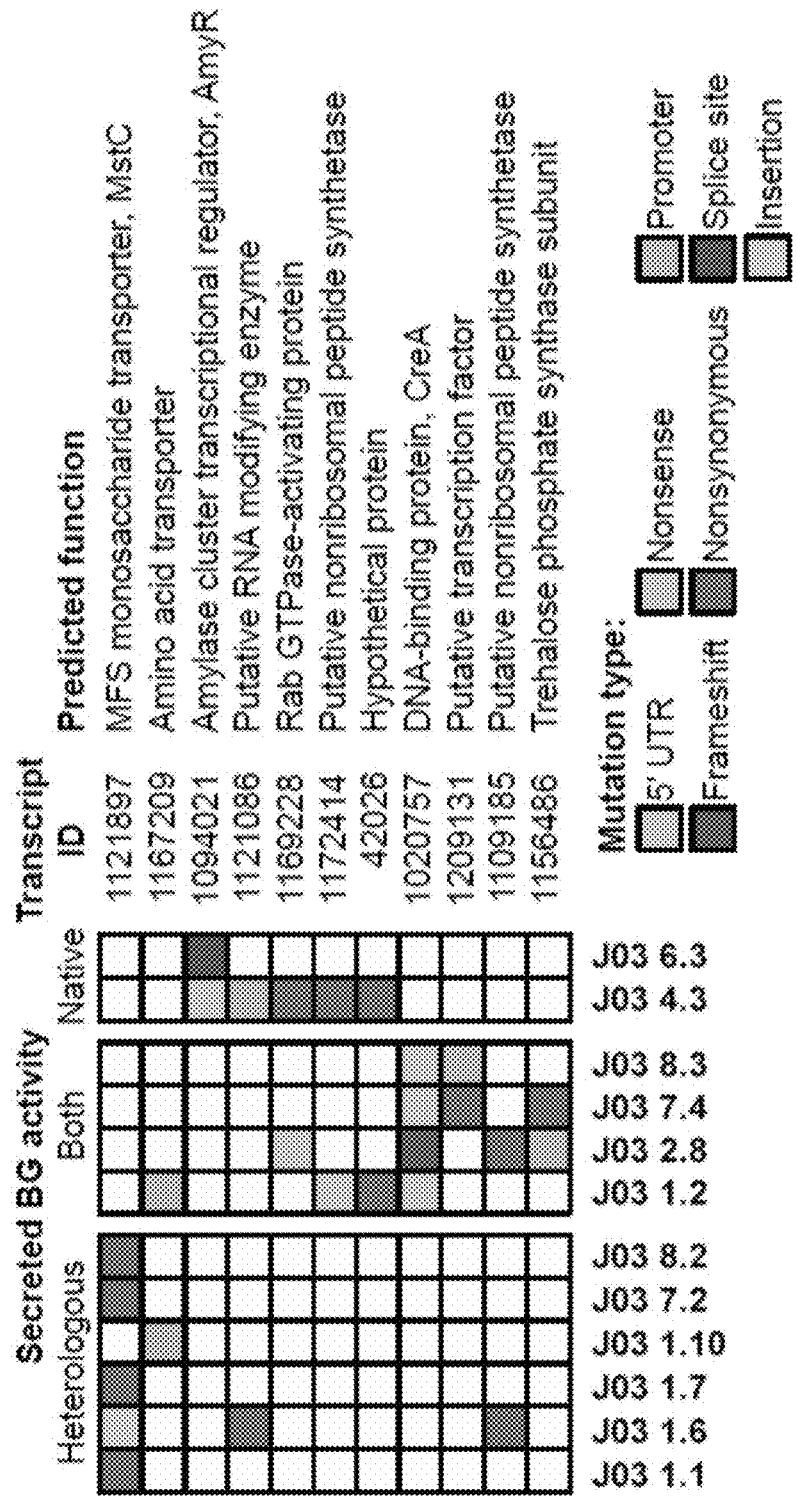
FIG. 3 shows mutations in J03-derivative strains associated with hyper-production of heterologous and/or native beta-glucosidase. Transcript ID references the filtered gene models of *A. niger* strain ATCC 1015 v4.0 (Aspni7 from the JGI). Predicted function is based on nearest homolog or presence of conserved domains after BLASTP analysis.

To identify the genomic lesions responsible for the hyper-production phenotypes observed in the mutants, DNA was prepared from the twelve mutant J03-derivative strains as well as the parent strain J03 and WT. Genomic DNA was sequenced by the Joint Genome Institute (JGI) and subsequently analyzed for mutations. Bcftools called 1,727 variants and GATK called 1,844 variants across all strains, and 1,694 and 1,326 variants passed fixed threshold filters, respectively. Among these, 962 variants called by both Bcftools and GATK were retained and subjected to annotation. Single nucleotide polymorphisms (SNPs) and small insertion/deletion (indel) calls were annotated using the filtered gene models of *A. niger* strain ATCC 1015 v4.0 (Aspni7 from the JGI). Variants in the coding regions, 5' UTR, 3' UTR, and splice sites (overlapping the first or last two nucleotides of an intron) were annotated first, followed by variants in the promoter region (500 bp upstream and 30 bp downstream of the transcription start site). Larger structural variants were visually inspected and manually annotated. Synonymous mutations in the coding region and variants present in the J03 parent strain were excluded from further analysis. The results of this analysis are presented in FIG. 3.

Figures 11A, 11B:
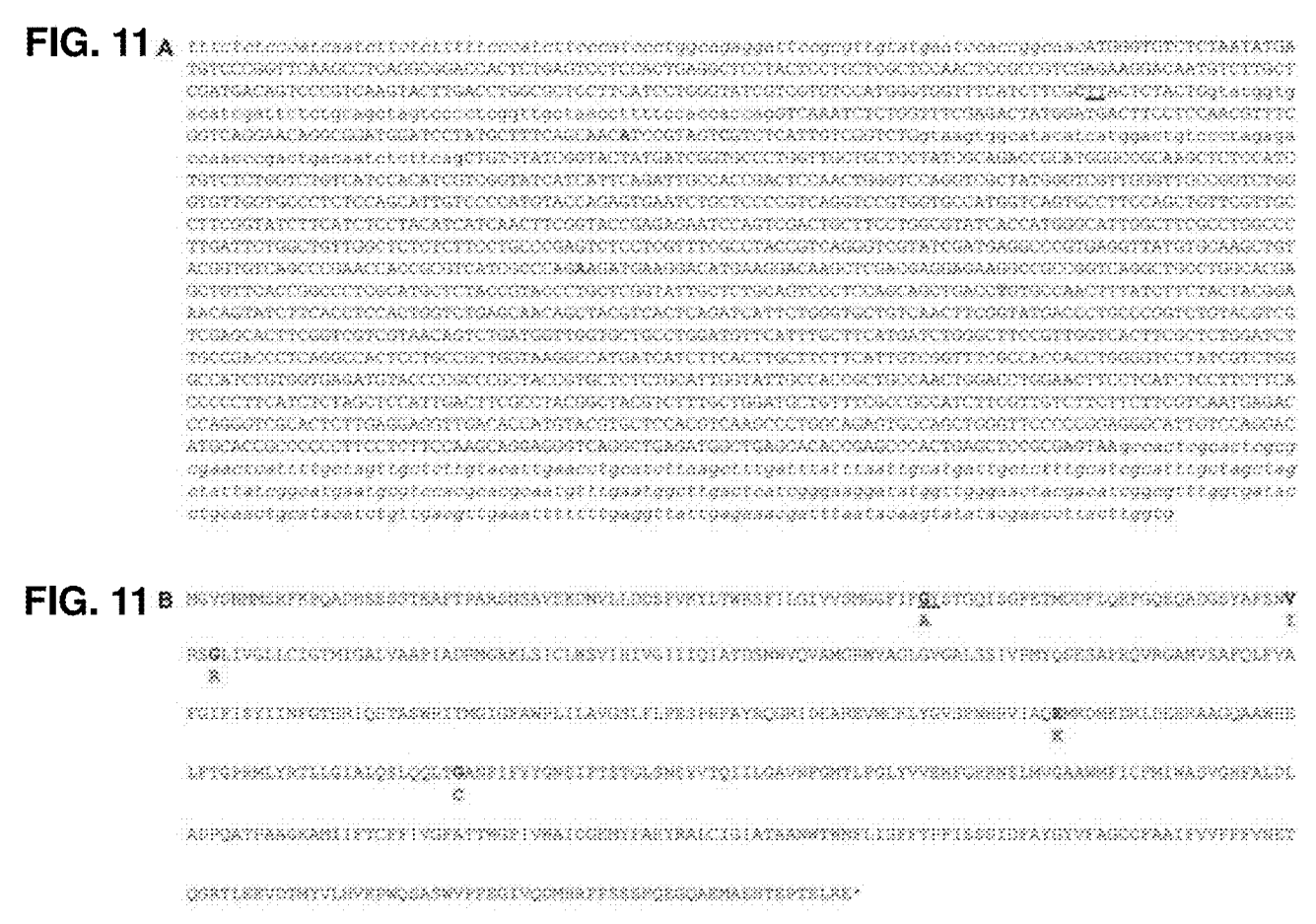

Of the six HET strains, five contained mutations (five missense and one insertion of ~9 kb sequence) within the coding region of Transcript ID 1121897, annotated as the low-affinity glucose transporter MstC (FIGS. 11A-11B and SEQ ID NO: 1 and 2). The one HET hyper-producer strains that does not have a mutation in mstC, J03 1.10, has a mutation in the promoter region of Transcript ID 1167209, a predicted amino acid transporter; this same promoter region was found to have a different mutation in one of the BOTH strains, J03 1.2.

All four of the BOTH strains have mutations (three independent nonsense and one frameshift) in Transcript ID 1020757, the DNA-binding carbon catabolite repression transcription factor CreA. Two of the BOTH strains (J03 7.4 and J03 8.3) have point mutations in either the coding or promoter region of Transcript ID 1209131, annotated as an unstudied fungal-specific transcription factor, while another pair (J03 2.8 and J03 7.4) have mutations in either the coding or promoter region of Transcript ID 1156486, a trehalose-6-phosphate synthase (TpsA), part of the trehalose synthesis pathway.

Finally, the two NAT strains have mutations in either the coding region or a splice site of Transcript ID 1094021, the amylase cluster transcriptional regulator AmyR. One of the NAT strains (J03 4.3) and one of the BOTH strains (J03 2.8) have mutations in either the 5' UTR or coding region of Transcript ID 1169228, annotated as a Ypt/Rab GTPase-activating protein involved in intracellular vesicle transport. Interestingly, J03 4.3 and J03 2.8 are the two highest BG producers among the J03-derivative strains, with J03 4.3 far outperforming the other NAT strain, J03 6.3 (Table 2).

Example 4

Targeted Deletion of mstC Locus

This example describes to the effect of deleting the mstC locus using the strain J03 to demonstrate an association between the mstC locus and hyper-production of heterologous enzyme. Based on these teachings, one skilled in the art will appreciate that mstC can be similarly deleted in other strains of *Aspergillus*.

Figure 4A:
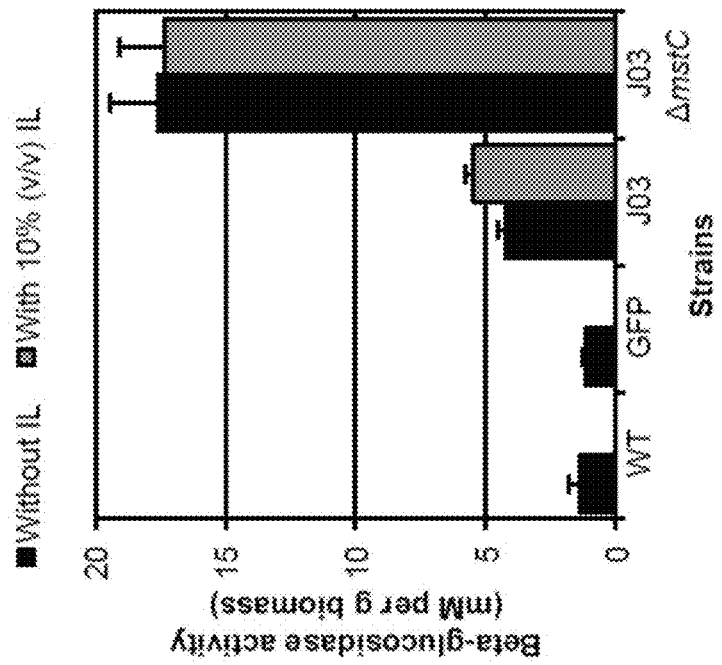
FIGS. 4A-4B are bar graphs showing loss of the mstC locus enhances heterologous enzyme production. (A) β-glucosidase activity and (B) total secreted protein of culture supernatant in CSL-HMM inducing conditions (units as described in FIG. 1). Biological replicates n=3; error bars indicate standard deviation.
Figure 4B:
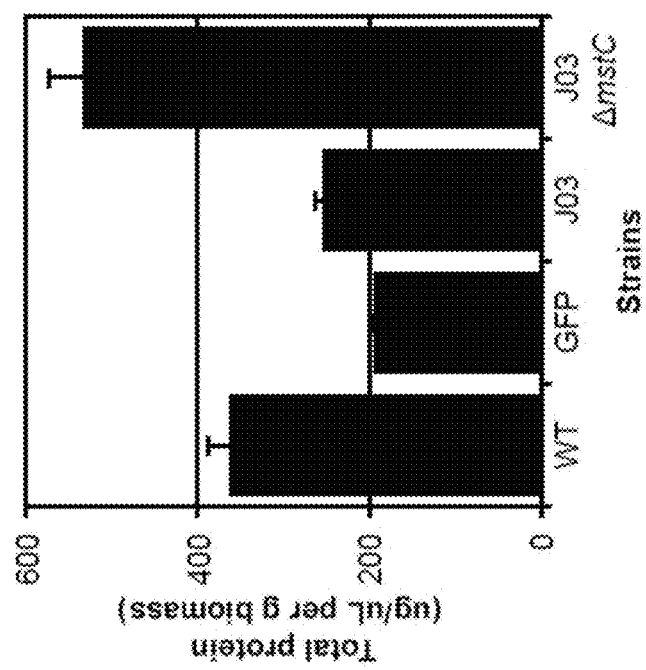

To establish an association between the identified loci and hyper-production of heterologous enzyme, deletion of the mstC locus was pursued. Initially, the mstC locus was targeted for deletion in the same J03 background that the mutagenesis screen had been performed in. As shown in FIG. 4A, analysis of the BG activity of a J03 ΔmstC strain found elevated levels of BG compared to the parental J03 strain and that this activity persisted in the presence of IL, indicating it was the heterologous J03 protein, as opposed to any native enzyme that was responsible for the increase in activity. As shown in FIG. 5, proteins found in the culture supernatants of both wild-type mstC and ΔmstC strains yielded a similar banding pattern when examined by SDS-PAGE though the bands are more intense in the J03 ΔmstC strain, reflective of the total secreted protein levels for these samples (FIG. 4B).

Figure 6A:
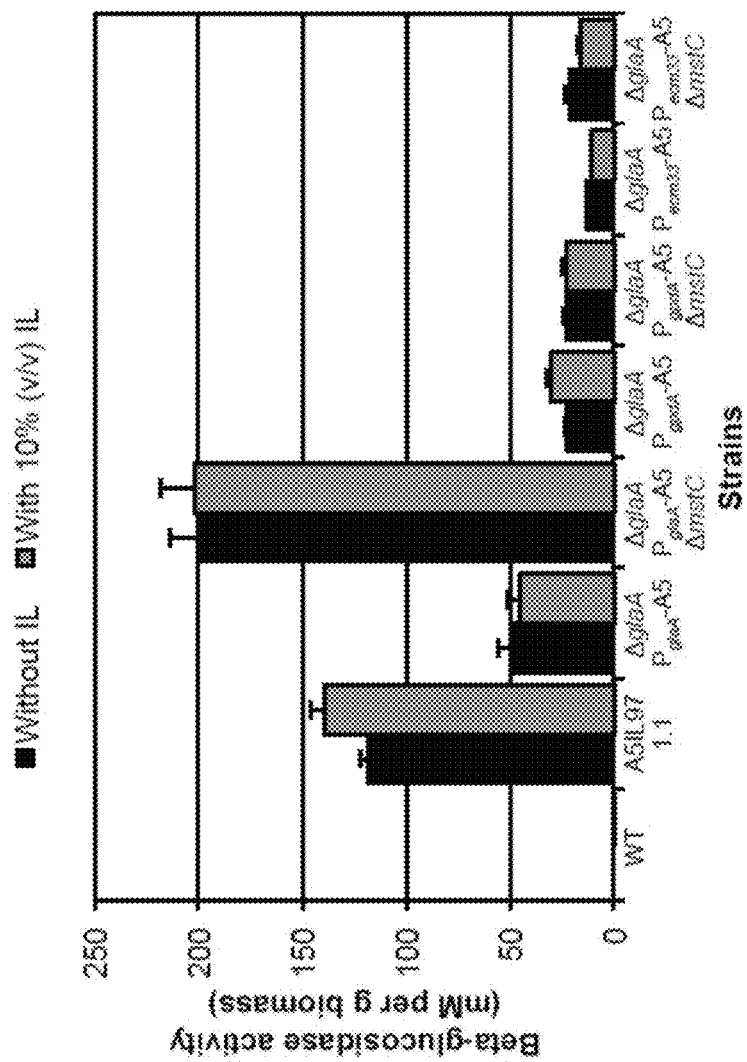
FIGS. 6A and 6B are graphs showing the impact of the mstC locus on enzyme production can be applied to other sequences in the heterologous expression construct but is limited to those behind the glaA promoter. (A) β-glucosidase activity and (B) total secreted protein of culture supernatant in CSL→HMM inducing conditions (units as described in FIG. 1). Biological replicates n=3; error bars indicate standard deviation. For clarity, relevant features of the strains—presence or absence of the native glaA and mstC loci, choice of promoter driving the heterologous β-glucosidase—are indicated at the bottom of the figure.
Figure 6B:
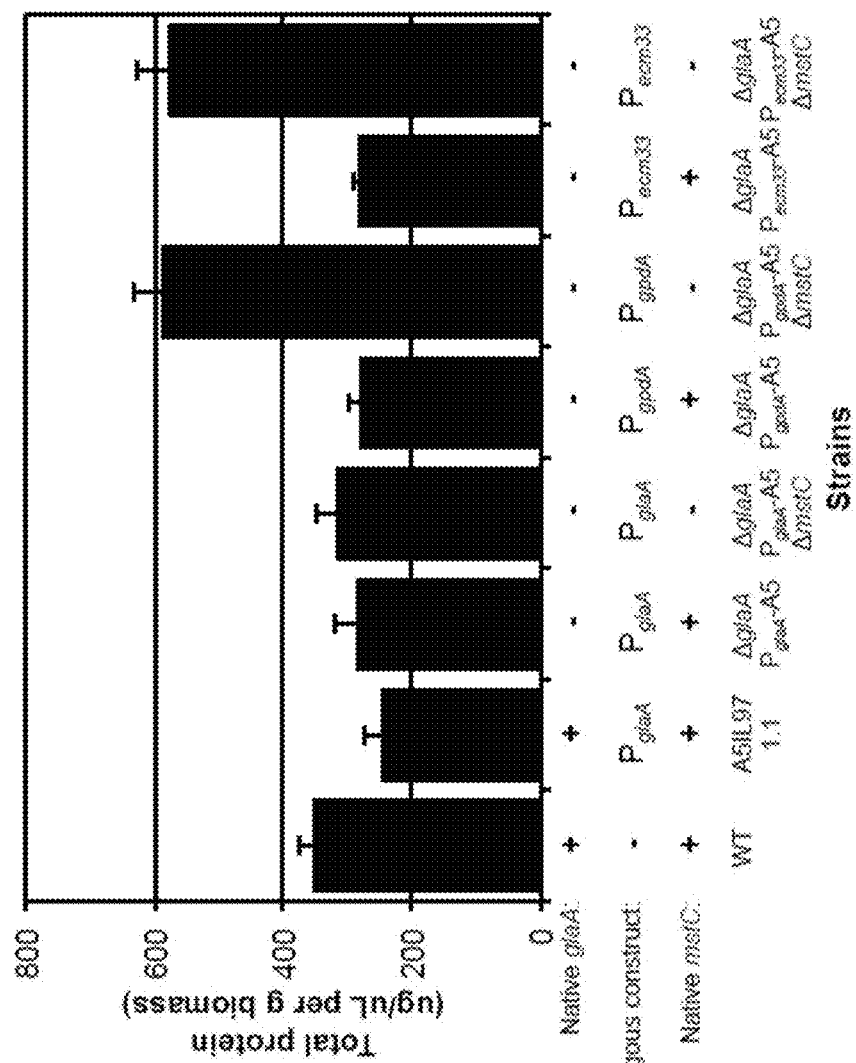
Figure 7:
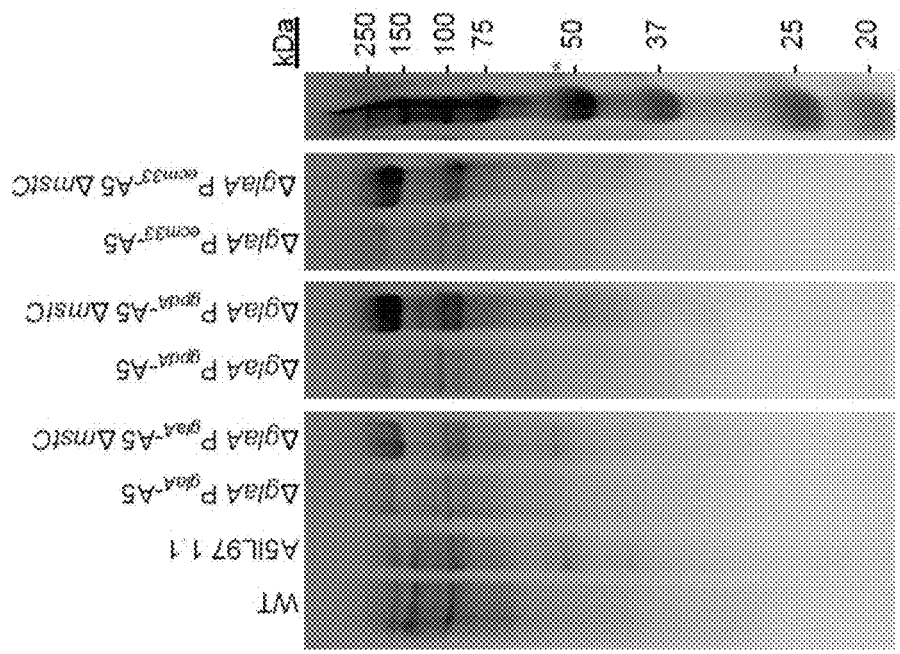
FIG. 7 a digital image of banding pattern examined by polyacrylamide gel electrophoresis (12% gradient polyacrylamide gel). Banding patterns of strains with promoters ΔglaA/P$_{glaA}$-A5, ΔglaA/P$_{gdpA}$-A5, and ΔglaA/P$_{ecm33}$-A5 are shown. Predicted molecular weight of A5IL97 (~52 kDa) is indicated with *.

Next, it was determined whether the increased enzyme production in the absence of mstC was specific to the heterologous expression construct present in the original J03 strain. For this, strains in which the native glaA locus had been replaced by a bacterial BG from *Thermotoga petrophila*, A5 (Park et al. 2012), under control of one of several different promoters were utilized: ΔglaA/$P_{glaA}$-A5, ΔglaA/$P_{gpdA}$-A5, and ΔglaA/$P_{ecm33}$-A5 (see Example 1 for description of assembly). These strains differ from the J03 ΔmstC strain in four respects: (1) expression of a distinct heterologous enzyme; (2) targeted as opposed to random integration of the expression construct; (3) deletion of the native glaA locus; and (4) use of additional constitutive promoters ($P_{gpdA}$ and $P_{ecm33}$) were tested. As shown in FIG. 6A, the three different promoters allow for a small range of A5-associated BG activity (ΔglaA/$P_{glaA}$-A5>ΔglaA/$P_{gpdA}$-A5>ΔglaA/$P_{ecm33}$-A5). Deletion of the native mstC locus in these backgrounds resulted in an at least four-fold increase in heterologous BG activity in the ΔglaA/$P_{glaA}$-A5 strain but negligible differences in the ΔglaA/$P_{gpdA}$-A5 and ΔglaA/$P_{ecm33}$-A5 backgrounds. Interestingly, both the ΔglaA/$P_{gpdA}$-A5 ΔmstC and ΔglaA/$P_{ecm33}$-A5 ΔmstC strains show significantly increased total protein section compared to ΔglaA/$P_{glaA}$-A5 ΔmstC (see FIG. 6B and FIG. 7) even though any change in A5 expression compared to the parent strain is minimal. Although the impact of ΔmstC on protein production is apparently restricted to those heterologous loci placed behind the glaA promoter, it does not seem to be limited to a particular protein sequence as both the J03 and A5 enzyme activities could be elevated.

Figure 8B:
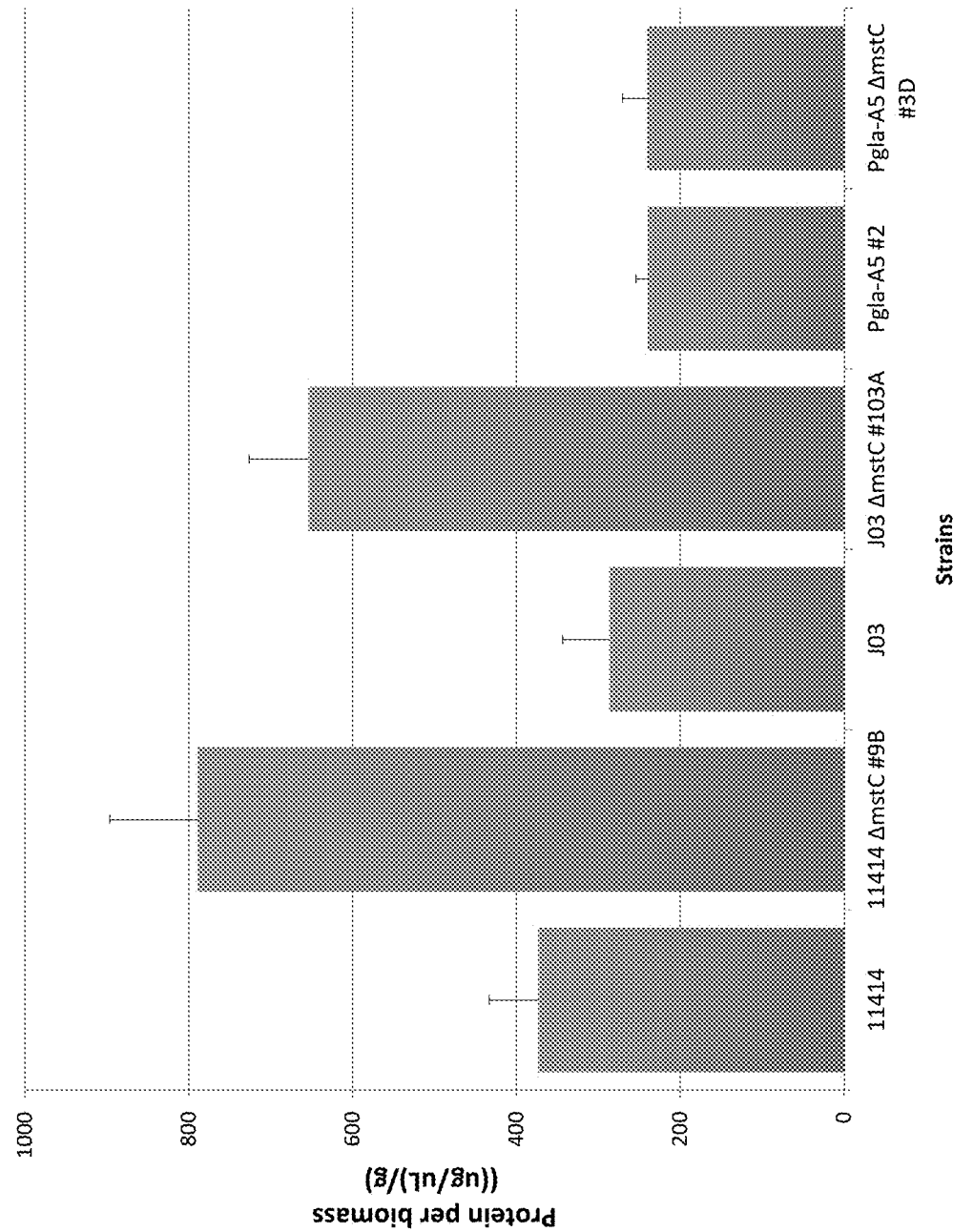
FIG. 8B is a bar graph showing the total protein levels in total protein secreted (μg/μL per g biomass) in WT, J03 and J03 ΔmstC strains.

To establish an association between the identified loci and hyper-production of heterologous enzyme in $P_{gla}$-A5 strains, the mstC locus was genetically inactivated. As shown in FIG. 8A, analysis of the BG activity of a $P_{gla}$-A5 ΔmstC strain found elevated levels of BG compared to the $P_{gla}$-A5 strain and that this activity persisted in the presence of IL, indicating it was the heterologous J03 protein as opposed to any native enzyme that was responsible for the increase in activity. As shown in FIG. 8B, the $P_{gla}$-A5 ΔmstC strain did not show a significant change in the overall amount of protein secreted compared to the $P_{gla}$-A5 strain.

Example 5

Native and Heterologous Enzyme Activity in ΔmstC Fungi

This example describes to the effect of deleting the mstC locus in strain J03 on production of a native (glucoamylase) and heterologous (beta-glucosidase) enzyme.

Figure 9:
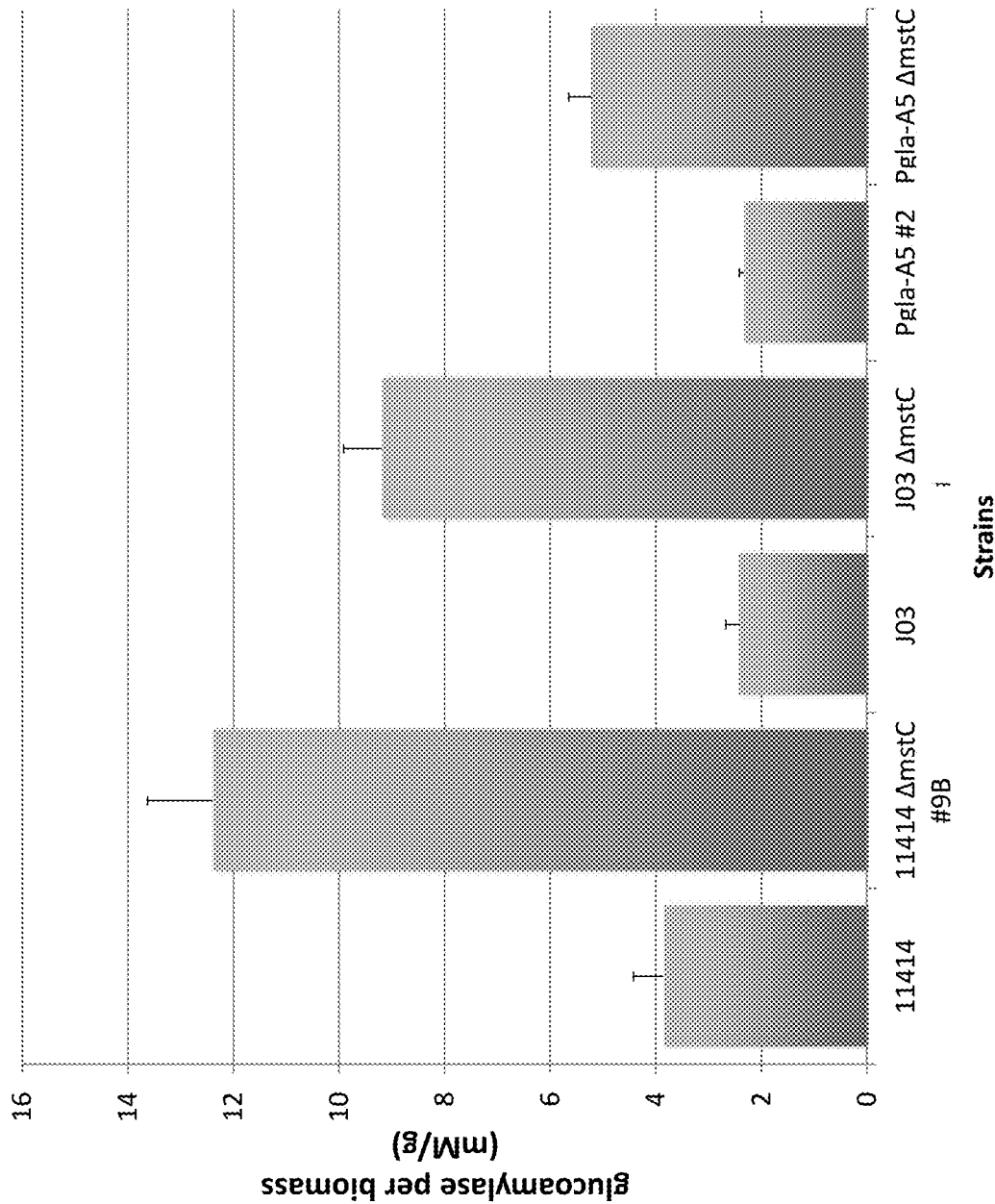
FIG. 9 is a bar graph showing glucoamylase production (mM per g biomass) in WT, J03 and J03 ΔmstC strains.

The mstC locus was deleted in the same J03 background described above. As shown in FIG. 8A, BG activity by expression from a glucoamylase promoter in the J03 ΔmstC strain resulted in elevated levels of BG compared to the parental strain. As shown in FIG. 9, expression of native glucoamylase was elevated in ΔmstC mutant strains compared to the parental strains.

Example 6

Genetic Inactivation of NCU01633 Locus in *Neurospora*

This example describes a comparison of the effect on glucoamylase expression in *A. niger* ΔmstC to *N. crassa* ΔNCU01633. Based on these teachings, one skilled in the art will appreciate that mstC and NCU01633 can be similarly deleted in other strains of *Aspergillus* and *Neurospora*, and that homologs of mstC and NCU01633 can be genetically inactivated in other fungi.

To establish an association between the identified loci and production of glucoamylase, mstC/NCU01633 was deleted. The mstC locus was deleted in the J03 background of *A. niger* as described above. The NCU01633 locus was deleted in *N. crassa* WT (FGSC 2489) to obtain the ΔNCU01633 mutant (FGSC 13161).

As shown in FIG. 10A, the ΔmstC mutant and the ΔNCU01633 mutant (FGSC 13161) showed significantly higher levels of glucoamylase production compared to the levels of the *A. niger* WT (11414) and *N. crassa* WT (FGSC 2489). FIG. 10B shows the total protein levels for *A. niger* and *N. crassa* and their mutant strains.

REFERENCES

Barratt et al., (1965) Wild-type and mutant stocks of *Aspergillus nidulans*. Genetics 52(1):233-246

Campen et al., (2017) Characterization of heterologously expressed bacterial thermophilic cellulases in *Aspergillus niger*.

Chen et al., (2009) BreakDancer: an algorithm for high-resolution mapping of genomic structural variation. Nat Methods 6(9):677-81 doi:10.1038/nmeth.1363

Chiang et al., (2011) Characterization of a polyketide synthase in *Aspergillus niger* whose product is a precursor for both dihydroxynaphthalene (DHN) melanin and naphthogammapyrone. Fungal Genet Biol 48(4):430-7 doi: 10.1016/j.fgb.2010.12.001 de Vries et al., (2017) Comparative genomics reveals high biological diversity and specific adaptations in the industrially and medically important fungal genus *Aspergillus*. Genome Biol 18(1):28 doi:10.1186/s 13059-017-1151-0

Diallinas G (2017) Transceptors as a functional link of transporters and receptors. Microb Cell 4(3):69-73 doi: 10.15698/mic2017.03.560 dos Reis et al., (2017) The low affinity glucose transporter HxtB is also involved in glucose signalling and metabolism in *Aspergillus nidulans*. Sci Rep 7:45073 doi: 10.1038/srep45073

Forment et al., (2006) Identification of the mstE gene encoding a glucose-inducible, low affinity glucose transporter in *Aspergillus nidulans*. J Biol Chem 281(13):8339-46 doi: 10.1074/jbc.M508198200

Fowler T, Berka R M, Ward M (1990) Regulation of the glaA gene of *Aspergillus niger*. Current Genetics 18(6): 537-545 doi: 10.1007/BF00327025

Ganzlin M, Rinas U (2008) In-depth analysis of the *Aspergillus niger* glucoamylase (glaA) promoter performance using high-throughput screening and controlled bioreactor cultivation techniques. J Biotechnol 135(3):266-71 doi: 10.1016/j.jbiotec.2008.04.005

Gladden et al., (2011) Glycoside hydrolase activities of thermophilic bacterial consortia adapted to switchgrass. Appl Environ Microbiol 77 doi:10.1128/AEM.00032-11

Gladden et al., (2014) Discovery and characterization of ionic liquid-tolerant thermophilic cellulases from a switchgrass-adapted microbial community. Biotechnology for Biofuels 7(1):15 doi:10.1186/1754-6834-7-15

Igor et al., (2011) Synthesis of glucose esters from cellulose in ionic liquids. Holzforschung. 66 (4): 417-425. doi: 10.1515/hf.2011.161

Jorgensen et al., J (2007) Glucose uptake and growth of glucose-limited chemostat cultures of *Aspergillus niger* and a disruptant lacking MstA, a high-affinity glucose transporter. Microbiology 153(Pt 6):1963-73 doi: 10.1099/mic.0.2006/005090-0

Kowalczyk et al., (2014) Regulation of Plant Biomass Utilization in *Aspergillus*. Advances in Applied Microbiology 88:31-56 doi:dx.doi.org/10.1016/B978-0-12-800260-5.00002-4.

Kubodera et al., (2000) Pyrithiamine Resistance Gene (ptrA) of *Aspergillus oryzae*: Cloning, characterization and application as a dominant selectable marker for transformation. Bioscience, Biotechnology, and Biochemistry 64(7):1416-1421 doi: 10.1271/bbb.64.1416

Layer et al., (2014) LUMPY: a probabilistic framework for structural variant discovery. Genome Biology 15(6):R84 doi: 10.1186/gb-2014-15-6-r84

Lee et al., (1996) Regulation of β-glucosidase biosynthesis in *Aspergillus nidulans*. FEMS Microbiol Lett 135(1):79-84 doi:10.1111/j.1574-6968.1996.tb07969

Li H (2011) A statistical framework for SNP calling, mutation discovery, association mapping and population genetical parameter estimation from sequencing data. Bioinformatics 27(21):2987-93 doi:10.1093/bioinformatics/btr509

Li H (2014) Toward better understanding of artifacts in variant calling from high-coverage samples. Bioinformatics 30(20):2843-51 doi: 10.1093/bioinformatics/btu356

Li et al., (2009) The Sequence Alignment/Map format and SAMtools. Bioinformatics 25(16):2078-9 doi:10.1093/bioinformatics/btp352

Lipatova Z, Hain A U, Nazarko V Y, Segev N (2015) Ypt/Rab GTPases: Principles learned from yeast. Critical Reviews in Biochemistry and Molecular Biology 50(3): 203-211 doi:10.3109/10409238.2015.1014023

McKenna et al., (2010) The Genome Analysis Toolkit: a MapReduce framework for analyzing next-generation DNA sequencing data. Genome Res 20(9):1297-303 doi: 10.1101/gr.107524.110

Meyer et al., (2015) The cell factory *Aspergillus* enters the big data era: opportunities and challenges for optimising product formation. In: Krull R, Bley T (eds) Filaments in Bioprocesses. Springer International Publishing, Cham, pp 91-132

Nakamura et al., (2006) Expression profile of amylolytic genes in *Aspergillus nidulans*. Biosci Biotechnol Biochem 70(10):2363-70 doi: 10.1271/bbb.50694

Obenchain et al., (2014) Variant Annotation: a Bioconductor package for exploration and annotation of genetic variants. Bioinformatics 30(14):2076-8 doi:10.1093/bioinformatics/btu168 Oliveira C, Guimaraes P M, Domingues L (2011) Recombinant microbial systems for improved beta-galactosidase production and biotechnological applications. Biotechnol Adv 29(6):600-9 doi: 10.1016/j.biotechadv.2011.03.008

Ozcan et al., (1996) Two glucose transporters in *Saccharomyces cerevisiae* are glucose sensors that generate a signal for induction of gene expression. Proceedings of the National Academy of Sciences of the United States of America 93(22): 12428-12432

Park et al., (2012) A thermophilic ionic liquid-tolerant cellulase cocktail for the production of cellulosic biofuels. PLoS One 7 doi:10.1371/journal.pone.0037010

Pontecorvo et al., (1953) The Genetics of *Aspergillus nidulans*. Advances in Genetics, pp 141-238

Rausch et al., (2012) DELLY: structural variant discovery by integrated paired-end and split-read analysis. Bioinformatics 28(18):i333-i339 doi:10.1093/bioinformatics/bts378

Ruijter G J, Visser J (1997) Carbon repression in aspergilli. FEMS Microbiol Lett 151(2):103-114 doi:10.1111/j.1574-6968.1997.tb12557

Schuster et al., (2002) On the safety of *Aspergillus niger*—a review. Appl Microbiol Biotechnol 59(4-5):426-35 doi: 10.1 007/s00253-002-1032-6

Silveira et al., (2015) Current pretreatment technologies for the development of cellulosic ethanol and biorefineries. ChemSusChem 8(20):3366-90 doi: 10.1002/cssc.201500282

Sloothaak et al., (2015) *Aspergillus niger* membrane-associated proteome analysis for the identification of glucose transporters. Biotechnol Biofuels 8:150 doi: 10.1186/s 13068-015-0317-9

Somerville et al., (2004) Toward a systems approach to understanding plant cell walls. Science 306(5705):2206 van Dijck et al., (2003) On the safety of a new generation of DSM *Aspergillus niger* enzyme production strains. Regulatory Toxicology and Pharmacology 38(1):27-35 doi: 10.1016/s0273-2300(03)00049-7 vanKuyk et al., (2012) A broader role for AmyR in *Aspergillus niger*: regulation of the utilisation of D-glucose or Dgalactose containing oligo- and polysaccharides. Appl Microbiol Biotechnol 93(1):285-93 doi: 10.1007/s00253-011-3550-6

Yang et al., (2014) Deletion of glucose oxidase changes the pattern of organic acid production in *Aspergillus carbonarius*. AMB Express 4(1):54 doi:10.1186/s 13568-014-0054-7

Ye et al., (2009) Pindel: a pattern growth approach to detect break points of large deletions and medium sized insertions from paired-end short reads. Bioinformatics 25(21): 2865-71 doi: 10.1093/bioinformatics/btp394

Yu et al., (2016) Ionic liquid-tolerant microorganisms and microbial communities for lignocellulose conversion to bioproducts. Appl Microbiol Biotechnol 100(24):10237-10249 doi: 10.1007/s00253-016-7955-0

In view of the many possible embodiments to which the principles of the disclosure may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

---

We claim:

1. A method of expressing a heterologous protein, comprising:
   culturing an isolated fungus in the genus *Aspergillus* under conditions that permit the fungus to express a heterologous protein; thereby expressing the heterologous protein,
   wherein:
   the isolated fungus comprises a polynucleotide comprising a glucoamylase promoter operably linked to a heterologous protein coding sequence, and
   the isolated fungus comprises a genetic inactivation of an mstC gene encoding a polypeptide comprising monosaccharide transporter activity and an amino acid sequence with at least 90% sequence identity to the amino acid sequence of SEQ ID NO: 2.

2. The method of claim 1, wherein the isolated fungus in the genus *Aspergillus* is *Aspergillus niger* (*A. niger*).

3. The method of claim 1, wherein the mstC gene is genetically inactivated by nonsynonymous mutation or by insertional mutation.

4. The method of claim 1, wherein:
   the mstC gene comprises a nucleic acid molecule comprising a nucleotide sequence having at least 95%, at least 98%, at least 99%, or 100% sequence identity to the nucleotide sequence of SEQ ID NO: 1, 3, or nucleotides 82 to 1764 of SEQ ID NO: 1.

5. The method of claim 1, wherein:
   the mstC gene encodes a protein comprising an amino acid sequence having at least 95%, at least 98%, at least 99%, or 100% amino acid sequence identity to the amino acid sequence of SEQ ID NO: 2.

6. The method of claim 1, wherein the heterologous protein is a heterologous enzyme, or a chimeric protein.

7. The method of claim 6, wherein expression of the heterologous enzyme is increased by at least 2-fold as compared to expression of the heterologous enzyme in a fungus comprising a native mstC gene.

8. A method of degrading a biomass comprising cellulose, comprising:
   incubating the biomass with an isolated fungus in the genus *Aspergillus* under conditions that permit the fungus to express a heterologous cellulolytic enzyme, thereby degrading the biomass, wherein:
   the isolated fungus comprises a polynucleotide comprising a glucoamylase promoter operably linked to a heterologous cellulolytic enzyme coding sequence, and
   the isolated fungus comprises a genetic inactivation of an mstC gene encoding a polypeptide comprising monosaccharide transporter activity and an amino acid sequence with at least 90% sequence identity to the amino acid sequence of SEQ ID NO: 2.

9. The method of claim 8, further comprising incubating the biomass with ionic liquids.

10. A method of expressing a heterologous protein, comprising:
    culturing an isolated fungus in the genus *Neurospora* under conditions that permit the fungus to express a heterologous protein; thereby expressing the heterologous protein,
    wherein:
    the isolated fungus comprises a polynucleotide comprising a glucoamylase promoter operably linked to a heterologous protein coding sequence, and
    the isolated fungus comprises a genetic inactivation of an NCU01633 gene encoding a polypeptide comprising monosaccharide transporter activity and an amino acid sequence with at least 90% sequence identity to the amino acid sequence of SEQ ID NO: 11.

11. The method of claim 10, wherein the isolated fungus in the genus *Neurospora* is *Neurospora crassa* (*N. crassa*).

12. The method of claim 10, wherein the NCU01633 gene is genetically inactivated by nonsynonymous mutation or by insertional mutation.

13. The method of claim 10, wherein the NCU01633 gene comprises at least 95%, at least 98%, at least 99%, or 100% sequence identity to SEQ ID NO: 9, 10, or nucleotides 652 to 2250 of SEQ ID NO: 10.

14. The method of claim 10, wherein the NCU01633 gene encodes a NCU01633 protein comprising an amino acid sequence having at least 95%, at least 98%, at least 99%, or 100% amino acid sequence identity to the amino acid sequence of SEQ ID NO: 11.

15. The method of claim 10, wherein the heterologous protein is a heterologous enzyme, or a chimeric protein.

16. The method of claim 15, wherein expression of the heterologous enzyme is increased by at least 2-fold as compared to expression of the heterologous enzyme in a fungus comprising a native NCU01633 gene.

17. A method of degrading a biomass comprising cellulose, comprising:
incubating the biomass with an isolated fungus in the genus *Neurospora* under conditions that permit the fungus to express a heterologous cellulolytic enzyme, thereby degrading the biomass, wherein:
the isolated fungus comprises a polynucleotide comprising a glucoamylase promoter operably linked to a heterologous cellulolytic enzyme coding sequence, and
the isolated fungus comprises a genetic inactivation of an NCU01633 gene encoding a polypeptide comprising monosaccharide transporter activity and an amino acid sequence with at least 90% sequence identity to the amino acid sequence of SEQ ID NO: 11.

18. The method of claim 17, further comprising incubating the biomass with ionic liquids.

* * * * *

SEQUENCE LISTING

```
<160> NUMBER OF SEQ ID NOS: 11

<210> SEQ ID NO 1
<211> LENGTH: 2069
<212> TYPE: DNA
<213> ORGANISM: Aspergillus niger

<400> SEQUENCE: 1
tttctctccc atcaatcttc tcttttccc atcttcccat ccctggcaga ggattccgcg      60
ttgtatgaat ccaccggcaa catgggtgtc tctaatatga tgtcccggtt caagcctcag     120
gcggaccact ctgagtcctc cactgaggct cctactcctc ctcgctccaa ctccgccgtc     180
gagaaggaca atgtcttgct cgatgacagt cccgtcaagt acttgacctg gcgctccttc     240
atcctgggta tcgtcgtgtc catgggtggt ttcatcttcg gttactctac tggtcaaatc     300
tctggtttcg agactatgga tgacttcctc caacgtttcg gtcaggaaca ggcggatgga     360
tcctatgctt tcagcaacgt ccgtagtggt ctcattgtcg gtctgctgtg tatcggtact     420
atgatcggtg ccctggttgc tgctcctatc gcagaccgca tgggccgcaa gctctccatc     480
tgtctctggt ctgtcatcca catcgtcggt atcatcattc agattgccac cgactccaac     540
tgggtccagg tcgctatggg tcgttgggtt gccggtctgg gtgttggtgc cctctccagc     600
attgtcccca tgtaccagag tgaatctgct ccccgtcagg tccgtggtgc catggtcagt     660
gccttccagc tgttcgttgc cttcggtatc ttcatctcct acatcatcaa cttcggtacc     720
gagagaatcc agtcgactgc ttcctggcgt atcaccatgg gcattggctt cgcctggccc     780
ttgattctgg ctgttggctc tctcttcctg cccgagtctc ctcgtttcgc ctaccgtcag     840
ggtcgtatcg atgaggcccg tgaggttatg tgcaagctgt acggtgtcag cccgaaccac     900
cgcgtcatcg cccaggagat gaaggacatg aaggacaagc tcgacgagga gaaggccgcc     960
ggtcaggctg cctggcacga gctgttcacc ggccctcgca tgctctaccg tacccctgctc    1020
```

```
ggtattgctc tgcagtccct ccagcagctg accggtgcca actttatctt ctactacgga   1080
aacagtatct tcacctccac tggtctgagc aacagctacg tcactcagat cattctgggt   1140
gctgtcaact tcggtatgac cctgcccggt ctgtacgtcg tcgagcactt cggtcgtcgt   1200
aacagtctga tggttggtgc tgcctggatg ttcatttgct tcatgatctg ggcttccgtt   1260
ggtcacttcg ctctggatct tgccgaccct caggccactc ctgccgctgg taaggccatg   1320
atcatcttca cttgcttctt cattgtcggt ttcgccacca cctggggtcc tatcgtctgg   1380
gccatctgtg gtgagatgta ccccgcccgc taccgtgctc tctgcattgg tattgccacc   1440
gctgccaact ggacctggaa cttcctcatc tccttcttca ccccccttcat ctctagctcc   1500 attgacttcg cctacggcta cgtctttgct ggatgctgtt tcgccgccat cttcgttgtc   1560
ttcttcttcg tcaatgagac ccagggtcgc actcttgagg aggttgacac catgtacgtg   1620
ctccacgtca agccctggca gagtgccagc tgggttcccc cggagggcat tgtccaggac   1680
atgcaccgcc cccttcctc ttccaagcag gagggtcagg ctgagatggc tgagcacacc   1740
gagcccactg agctccgcga gtaagccact cgcactcgcg cgaactcatt ttgctagttg   1800
ctcttgtaca ttgaacctgc atcttaagct ttgatttatt taattgcatg attgctcttt   1860
gcatcgcatt tgctagctag ctattatcgg catgaatgcg tccacgcacg caatgtttga   1920
atggcttgac tcatcgggaa ggatatggtt gggaactacg acatcggcgt ttggtgatac   1980
ctgcaactgc atacatctgt tgacgttgaa attttttga ggttattgag aaacgattta   2040
atacaagtat atacgaacct tacttggtg                                     2069
```

<210> SEQ ID NO 2
<211> LENGTH: 560
<212> TYPE: PRT
<213> ORGANISM: Aspergillus niger

<400> SEQUENCE: 2

```
Met Gly Val Ser Asn Met Met Ser Arg Phe Lys Pro Gln Ala Asp His
1               5                   10                  15

Ser Glu Ser Ser Thr Glu Ala Pro Thr Pro Ala Arg Ser Asn Ser Ala
            20                  25                  30

Val Glu Lys Asp Asn Val Leu Leu Asp Asp Ser Pro Val Lys Tyr Leu
        35                  40                  45

Thr Trp Arg Ser Phe Ile Leu Gly Ile Val Ser Met Gly Gly Phe
    50                  55                  60

Ile Phe Gly Tyr Ser Thr Gly Gln Ile Ser Gly Phe Glu Thr Met Asp
65                  70                  75                  80

Asp Phe Leu Gln Arg Phe Gly Gln Glu Gln Ala Asp Gly Ser Tyr Ala
                85                  90                  95

Phe Ser Asn Val Arg Ser Gly Leu Ile Val Gly Leu Leu Cys Ile Gly
            100                 105                 110

Thr Met Ile Gly Ala Leu Val Ala Ala Pro Ile Ala Asp Arg Met Gly
        115                 120                 125

Arg Lys Leu Ser Ile Cys Leu Trp Ser Val Ile His Ile Val Gly Ile
    130                 135                 140

Ile Ile Gln Ile Ala Thr Asp Ser Asn Trp Val Gln Val Ala Met Gly
145                 150                 155                 160

Arg Trp Val Ala Gly Leu Gly Val Gly Ala Leu Ser Ser Ile Val Pro
                165                 170                 175

Met Tyr Gln Ser Glu Ser Ala Pro Arg Gln Val Arg Gly Ala Met Val
            180                 185                 190
```

Ser Ala Phe Gln Leu Phe Val Ala Phe Gly Ile Phe Ile Ser Tyr Ile
            195                 200                 205

Ile Asn Phe Gly Thr Glu Arg Ile Gln Ser Thr Ala Ser Trp Arg Ile
210                 215                 220

Thr Met Gly Ile Gly Phe Ala Trp Pro Leu Ile Leu Ala Val Gly Ser
225                 230                 235                 240

Leu Phe Leu Pro Glu Ser Pro Arg Phe Ala Tyr Arg Gln Gly Arg Ile
            245                 250                 255

Asp Glu Ala Arg Glu Val Met Cys Lys Leu Tyr Gly Val Ser Pro Asn
            260                 265                 270

His Arg Val Ile Ala Gln Glu Met Lys Asp Met Lys Asp Lys Leu Asp
            275                 280                 285

Glu Glu Lys Ala Ala Gly Gln Ala Ala Trp His Glu Leu Phe Thr Gly
            290                 295                 300

Pro Arg Met Leu Tyr Arg Thr Leu Leu Gly Ile Ala Leu Gln Ser Leu
305                 310                 315                 320

Gln Gln Leu Thr Gly Ala Asn Phe Ile Phe Tyr Tyr Gly Asn Ser Ile
            325                 330                 335

Phe Thr Ser Thr Gly Leu Ser Asn Ser Tyr Val Thr Gln Ile Ile Leu
            340                 345                 350

Gly Ala Val Asn Phe Gly Met Thr Leu Pro Gly Leu Tyr Val Val Glu
            355                 360                 365

His Phe Gly Arg Arg Asn Ser Leu Met Val Gly Ala Ala Trp Met Phe
            370                 375                 380

Ile Cys Phe Met Ile Trp Ala Ser Val Gly His Phe Ala Leu Asp Leu
385                 390                 395                 400

Ala Asp Pro Gln Ala Thr Pro Ala Ala Gly Lys Ala Met Ile Ile Phe
            405                 410                 415

Thr Cys Phe Phe Ile Val Gly Phe Ala Thr Thr Trp Gly Pro Ile Val
            420                 425                 430

Trp Ala Ile Cys Gly Glu Met Tyr Pro Ala Arg Tyr Arg Ala Leu Cys
            435                 440                 445

Ile Gly Ile Ala Thr Ala Ala Asn Trp Thr Trp Asn Phe Leu Ile Ser
            450                 455                 460

Phe Phe Thr Pro Phe Ile Ser Ser Ser Ile Asp Phe Ala Tyr Gly Tyr
465                 470                 475                 480

Val Phe Ala Gly Cys Cys Phe Ala Ala Ile Phe Val Phe Phe Phe
            485                 490                 495

Val Asn Glu Thr Gln Gly Arg Thr Leu Glu Glu Val Asp Thr Met Tyr
            500                 505                 510

Val Leu His Val Lys Pro Trp Gln Ser Ala Ser Trp Val Pro Pro Glu
            515                 520                 525

Gly Ile Val Gln Asp Met His Arg Pro Pro Ser Ser Ser Lys Gln Glu
            530                 535                 540

Gly Gln Ala Glu Met Ala Glu His Thr Glu Pro Thr Glu Leu Arg Glu
545                 550                 555                 560

<210> SEQ ID NO 3
<211> LENGTH: 2189
<212> TYPE: DNA
<213> ORGANISM: Aspergillus niger

<400> SEQUENCE: 3
tttctctccc atcaatcttc tcttttcccc atcttcccat ccctggcaga ggattccgcg      60

```
ttgtatgaat ccaccggcaa catgggtgtc tctaatatga tgtcccggtt caagcctcag    120
gcggaccact ctgagtcctc cactgaggct cctactcctg ctcgctccaa ctccgccgtc    180
gagaaggaca atgtcttgct cgatgacagt cccgtcaagt acttgacctg gcgctccttc    240
atcctgggta tcgtcgtgtc catgggtggt ttcatcttcg gttactctac tggtatggtg    300
acatcgattc tctgcagcta gtcccctcgg ttgctaacct tttccaccac caggtcaaat    360
ctctggtttc gagactatgg atgacttcct ccaacgtttc ggtcaggaac aggcggatgg    420
atcctatgct ttcagcaacg tccgtagtgg tctcattgtc ggtctggtaa gtggcataca    480
tcatggactg tccctagaga ccaacccgac tgacaatctc ttcagctgtg tatcggtact    540
atgatcggtg ccctggttgc tgctcctatc gcagaccgca tgggccgcaa gctctccatc    600
tgtctctggt ctgtcatcca catcgtcggt atcatcattc agattgccac cgactccaac    660
tgggtccagg tcgctatggg tcgttgggtt gccggtctgg gtgttggtgc cctctccagc    720
attgtcccca tgtaccagag tgaatctgct ccccgtcagg tccgtggtgc catggtcagt    780
gccttccagc tgttcgttgc cttcggtatc ttcatctcct acatcatcaa cttcggtacc    840
gagagaatcc agtcgactgc ttcctggcgt atcaccatgg gcattggctt cgcctggccc    900
ttgattctgg ctgttggctc tctcttcctg cccgagtctc ctcgtttcgc ctaccgtcag    960
ggtcgtatcg atgaggcccg tgaggttatg tgcaagctgt acggtgtcag cccgaaccac    1020
cgcgtcatcg cccaggagat gaaggacatg aaggacaagc tcgacgagga gaaggccgcc    1080
ggtcaggctg cctggcacga gctgttcacc ggccctcgca tgctctaccg taccctgctc    1140
ggtattgctc tgcagtccct ccagcagctg accggtgcca actttatctt ctactacgga    1200
aacagtatct tcacctccac tggtctgagc aacagctacg tcactcagat cattctgggt    1260
gctgtcaact tcggtatgac cctgcccggt ctgtacgtcg tcgagcactt cggtcgtcgt    1320
aacagtctga tggttggtgc tgcctggatg ttcatttgct tcatgatctg gcttccgtt     1380
ggtcacttcg ctctggatct tgccgaccct caggccactc ctgccgctgg taaggccatg    1440
atcatcttca cttgcttctt cattgtcggt ttcgccacca cctggggtcc tatcgtctgg    1500
gccatctgtg gtgagatgta ccccgcccgc taccgtgctc tctgcattgg tattgccacc    1560
gctgccaact ggacctggaa cttcctcatc tccttcttca ccccccttcat ctctagctcc    1620
attgacttcg cctacggcta cgtctttgct ggatgctgtt tcgccgccat cttcgttgtc    1680
ttcttcttcg tcaatgagac ccagggtcgc actcttgagg aggttgacac catgtacgtg    1740
ctccacgtca agccctggca gagtgccagc tgggttcccc cggagggcat tgtccaggac    1800
atgcaccgcc ccccttcctc ttccaagcag gagggtcagg ctgagatggc tgagcacacc    1860
gagcccactg agctccgcga gtaagccact cgcactcgcg cgaactcatt ttgctagttg    1920
ctcttgtaca ttgaacctgc atcttaagct ttgatttatt taattgcatg attgctcttt    1980
gcatcgcatt tgctagctag ctattatcgg catgaatgcg tccacgcacg caatgtttga    2040
atggcttgac tcatcgggaa ggatatggtt gggaactacg acatcggcgt ttggtgatac    2100
ctgcaactgc atacatctgt tgacgttgaa attttttga ggttattgag aaacgattta     2160
atacaagtat atacgaacct tacttggtg                                       2189
```

<210> SEQ ID NO 4
<211> LENGTH: 1849
<212> TYPE: DNA
<213> ORGANISM: Aspergillus niger

<400> SEQUENCE: 4

```
atggactctc atccttcccc taccaaacaa aaggcctcca agcaagcctg cgacaactgt      60
cgtcggcgta agatcaagtg ctcgagagag cttccctgcg ataagtgtcg acgccttctt     120
ctttcttgtt cctacagtga tgtgctccgg cgcaaaggcc ccaagttccg caccttatat     180
ccacttgcgc ccattcatcc cctggtatca cgacaacaga atacatacca acagaattcg     240
tcacaaaatc cgttaaacaa gcaatggact gcagatggag tgggctatcc gttaagctca     300
ctaatgtcgc cttctttcac agtggcagac cctcaatact taccccatga cgctcccgag     360
ccgttctctc agtttcctcc gccagagcta gtctcctcac ccgactcaac caattcattg     420
tcagactcta gtatggcact agtgcgccct tatgcacgac gcctgtctgc tccggtgcta     480
cttgctcatg tgaatgttta tctaaaatat ctgttcccca tcatgcctgt ggtgcggaag     540
gaggagcttc aacaagattg ccaccagcct gaacggttat cgccccaacg atatgccttt     600
cttgtcgccc tatgcgcagc cacacacatc cagctgaaac tagatggcac agcatctgtc     660
ccagaacctt cacaccttca agccgggatt gacgggcatt cctggatgtc cggcgaagag     720
ttgctggctg aagcagtacg cgcaaggaag gattgcgacc cagtagacgg catgaacata     780
gaaagccttc ttacgtcttt cttcctgttt gcttcgtatg gtaacctgga caaacaggac     840
catgcctggt tctacctttg tcaggcaaca tccatggtct tcacgctggc actccaccga     900
gagtcaagtt atgtggatct gagtaccgaa gaagcagagg aacgacgcaa ggtgttttgg     960
ctactgtttg tcaccgaaag gtaggtgcat cctatgaaag cattgcccat ttttcgacta    1020
atgtgaatca ggggctacgc acttcaacaa tcgaaaccgg taatgctgcg taattcaatc    1080
cgcaagcctc aagtactttg ctccgaagat cctatcttgg cctacggttt catcaatctt    1140
attagcatct ttgagaaact gaccgtcaac ctttatgact gggtctctgc gggaggcatg    1200
gacggctcgt ccgagatgcc cctacatctc gctattcagt ctagtctctg caacgcaatt    1260
tcggtcgacg gagtctcgga gattcaaaag gtcgacatac tcatcaccca gcaatggcta    1320
cagacagtaa tgtggaaact ttctatgact cgtgctactc agcctggatc tcgcgatgag    1380
gcggttcttc cctttcatct ccccgttctt gtcggaaaag ccgttatgaa tgttattggt    1440
gctgcatccc agggagctgt tgatgttcac ggcattggca tggtcagtat cttagttccg    1500
gcgcagcaca tgccaatacc atttactaac aacataacag gaacaaaaat tattcgacct    1560
gggttcctca gttgcagacg tggcacgatc actcaactcc aaagctgcgc accgccttac    1620
tgaagcggcc gtcgatcctc gcgaactcct ttggggcatt cttaccacct tatcacgcat    1680
ccgcggctct cagtcctacc tctttccttc attgttggag cgatgcaaag gcgccctgga    1740
ctttacctcc cccacgtcga tgggcaactt cctcccctcca ttatccactg cttccacatg    1800
gggaagagga acggggctc gccgtggttt ctgtcccgga gaatcctga               1849
```

<210> SEQ ID NO 5
<211> LENGTH: 579
<212> TYPE: PRT
<213> ORGANISM: Aspergillus niger

<400> SEQUENCE: 5

```
Met Asp Ser His Pro Ser Pro Thr Lys Gln Lys Ala Ser Lys Gln Ala
1               5                   10                  15

Cys Asp Asn Cys Arg Arg Arg Lys Ile Lys Cys Ser Arg Glu Leu Pro
            20                  25                  30

Cys Asp Lys Cys Arg Arg Leu Leu Leu Ser Cys Ser Tyr Ser Asp Val
```

-continued

```
            35                  40                  45
Leu Arg Arg Lys Gly Pro Lys Phe Arg Thr Leu Tyr Pro Leu Ala Pro
 50                  55                  60
Ile His Pro Leu Val Ser Arg Gln Gln Asn Thr Tyr Gln Gln Asn Ser
 65                  70                  75                  80
Ser Gln Asn Pro Leu Asn Lys Gln Trp Thr Ala Asp Gly Val Gly Tyr
                 85                  90                  95
Pro Leu Ser Ser Leu Met Ser Pro Ser Phe Thr Val Ala Asp Pro Gln
            100                 105                 110
Tyr Leu Pro His Asp Ala Pro Glu Pro Phe Ser Gln Phe Pro Pro Pro
            115                 120                 125
Glu Leu Val Ser Ser Pro Asp Ser Thr Asn Ser Leu Ser Asp Ser Ser
130                 135                 140
Met Ala Leu Val Arg Pro Tyr Ala Arg Arg Leu Ser Ala Pro Val Leu
145                 150                 155                 160
Leu Ala His Val Asn Val Tyr Leu Lys Tyr Leu Phe Pro Ile Met Pro
                165                 170                 175
Val Val Arg Lys Glu Glu Leu Gln Gln Asp Cys His Gln Pro Glu Arg
            180                 185                 190
Leu Ser Pro Gln Arg Tyr Ala Phe Leu Val Ala Leu Cys Ala Ala Thr
            195                 200                 205
His Ile Gln Leu Lys Leu Asp Gly Thr Ala Ser Val Pro Glu Pro Ser
210                 215                 220
His Leu Gln Ala Gly Ile Asp Gly His Ser Trp Met Ser Gly Glu Glu
225                 230                 235                 240
Leu Leu Ala Glu Ala Val Arg Ala Arg Lys Asp Cys Asp Pro Val Asp
                245                 250                 255
Gly Met Asn Ile Glu Ser Leu Leu Thr Ser Phe Phe Leu Phe Ala Ser
            260                 265                 270
Tyr Gly Asn Leu Asp Lys Gln Asp His Ala Trp Phe Tyr Leu Cys Gln
            275                 280                 285
Ala Thr Ser Met Val Phe Thr Leu Ala Leu His Arg Glu Ser Ser Tyr
290                 295                 300
Val Asp Leu Ser Thr Glu Glu Ala Glu Glu Arg Arg Lys Val Phe Trp
305                 310                 315                 320
Leu Leu Phe Val Thr Glu Arg Gly Tyr Ala Leu Gln Gln Ser Lys Pro
                325                 330                 335
Val Met Leu Arg Asn Ser Ile Arg Lys Pro Gln Val Leu Cys Ser Glu
            340                 345                 350
Asp Pro Ile Leu Ala Tyr Gly Phe Ile Asn Leu Ile Ser Ile Phe Glu
            355                 360                 365
Lys Leu Thr Val Asn Leu Tyr Asp Trp Val Ser Ala Gly Gly Met Asp
            370                 375                 380
Gly Ser Ser Glu Met Pro Pro Thr Ser Ala Ile Gln Ser Ser Leu Cys
385                 390                 395                 400
Asn Ala Ile Ser Val Asp Gly Val Ser Glu Ile Gln Lys Val Asp Ile
                405                 410                 415
Leu Ile Thr Gln Gln Trp Leu Gln Thr Val Met Trp Lys Leu Ser Met
            420                 425                 430
Thr Arg Ala Thr Gln Pro Gly Ser Arg Asp Glu Ala Val Leu Pro Phe
            435                 440                 445
His Leu Pro Val Leu Val Gly Lys Ala Val Met Asn Val Ile Gly Ala
450                 455                 460
```

```
Ala Ser Gln Gly Ala Val Asp Val His Gly Ile Gly Met Glu Gln Lys
465                 470                 475                 480

Leu Phe Asp Leu Gly Ser Ser Val Ala Asp Val Ala Arg Ser Leu Asn
                485                 490                 495

Ser Lys Ala Ala His Arg Leu Thr Glu Ala Ala Val Asp Pro Arg Glu
                500                 505                 510

Leu Leu Trp Gly Ile Leu Thr Thr Leu Ser Arg Ile Arg Gly Ser Gln
                515                 520                 525

Ser Tyr Leu Phe Pro Ser Leu Leu Glu Arg Cys Lys Gly Ala Leu Asp
530                 535                 540

Phe Thr Ser Pro Thr Ser Met Gly Asn Phe Leu Pro Pro Leu Ser Thr
545                 550                 555                 560

Ala Ser Thr Trp Gly Arg Gly Asn Gly Ala Arg Arg Gly Phe Cys Pro
                565                 570                 575

Gly Glu Ser

<210> SEQ ID NO 6
<211> LENGTH: 3453
<212> TYPE: DNA
<213> ORGANISM: Aspergillus niger

<400> SEQUENCE: 6
cccgggcctt acagctttac cttaccgaca cccaacaata cggggcacgc acttctccag      60
accacacagc cacttctgca gttccagttt ctactccgta atccctctcg actctagtcc     120
gccccacatt ctttttttt tcttaacacg ccttaccttt tttgacaccc tctcttcccg     180
gtcagtaata gtggaatttt tttaacacac cgtgcgtggc ccgaaaacca gacggaagaa     240
gccccgagat aggcaactga tggagacacc cgtttgccat ttggcaattc aaggactttg     300
aagagatcat attcatcaga gaacacaaga tctgagagag tgtgtaagag cggtagatac     360
ccaagattgt aaaatcatct atcaagtcaa gaaaattata aaaagaataa gaagagcatg     420
aaataactac aaagcactgg gttccatctg actgggaaag ctgactgacc ggtttgaagc     480
cccaagaagc aaagcagccg atctggttca agcacgttct ttttcccttt cctgcttttt     540 ttgcccccc gatatttatc cccacacaaa gtacatagtc ttttcttttt tcgattttt     600 tttttaaatc cctttttttt tattcttatt tccctttcg taattttttt tatccatctt     660
tttttcgatt ttttcaattt tcttttttcct tttttttttc tttttttttt tttttttctt     720
cgcgttccca ttctgctctc cgattccgat aacccacccc ctctacgact cgccctcttt     780
tccctcccct ccccgaatt ccgtttcctt cttcttcccc tccattcctc atctttttcgc     840 cctttccgat ttcttctctt cttatatctt cgtctcccca gatcatcttc tccaggtttt     900
cttcctccct ccctcttttc gagaccattt gctcaacatc acccttgccc gactcgctac     960
ttattacccc ggggtccatt tccgattccg gctcacccaa cacttatcat aactaccaca    1020
ttccgtatcc cttcaataat tgaaaggaat tcgtcgttat cagcccttgg ttgaattcac    1080
aattgaatac cgcctcgcct tggttcgtca tcagggccct gtgatcctca ctacccttgc    1140
ggtcttcctc ctatcatctc tccttgccaa ggttaggtct ggggtgctag cgggaggtga    1200
tcgactggcc gatatagcta cccctggtcg cgacgtgcat cactatcgcc tcggcttctc    1260
atcccttccg aacgtgtcct tttaaaaccc ggctctgtcc tacctttta ccctcgtcgg    1320 tctttgggaca agcttcacat gccgccaccg gcctcttcag tagatttctc aaatctgctg    1380
aaccctcaaa acaattccac tgattccacc ccttccactc ctgtggacag ctccaagacc    1440
```

```
ccttctactc cgtccagtac acagtcgaac tccaacatgg cgtcgtcagt gagcctactt    1500
ccgccgctta tgaagggtgc ccggcctgcg accgaagaag ttcgtcagga tcttccccgc    1560
ccctacaagt gcccnctctg cgatcgcgca ttccaccgtc tggagcacca gacaagacac    1620
atccgcacgc acacgggtga aaagccgcat gcctgtcaat tccccggctg cactaagcgc    1680
ttcagtcgtt ctgacgagct tacgcgccac tcgcgaatcc acaacaaccc taactcgaga    1740
cgtcgaaaca aggctcagca tctggctgcg gccgctgcag ctgctgcagg caggacaac     1800 gccatggcca acaccgccag cgctatgatg cctcctccca gcaagccaat gacccggtcg    1860
gcccctgtct cgcaggtcgg ctcccccgac atctctcccc ctcactcctt ctccaactac    1920
gccagtcaca tgcgatcgaa cttgggcccg tatgctcgca aaggcgacga ggcatcgtcg    1980
ggcatggaac ataccctcct ggcgactgct cgtcgcagg tggaacgcga cgaacacttc     2040
gacttccatg cagggccacg caatcaccat ttgttcagct cgcgccacca tggaagtggc    2100
cgtctgcccc tccttgctgc ttacgcgatc acacacaaca tgagccggtc gcattcacct    2160
gaagacgacg acggttattc gcaccgtgtg aaacgttcaa gacccaactc tcccaactcg    2220
actgctcctt cctctcccac cttctcccac gactccctct caccactcc cgatcacact    2280 cccttggcga ctcccgctca ctcaccgcgg ttgagacccc tgggctccag cgatctgcat    2340
ttgccgtcta tccgtcattt gtcgctccac cacacaccag ctcttgctcc gatgaaccc    2400 caaccggaag ggcccaacta ctacagtcct tcccagggtc accatggtcc cagcatctcg    2460
gacatcatgt ctaaaccgga cggaacacag cgcaagctgc cagtccctca ggtgccaaaa    2520
gtcgccgttc aggatatgtt aaatcccggt agtggatttt cgtcggtcca ttcgtccacc    2580
gcgaattccg ttgccggtgg cgacttggca gaacgcttct agttcgaaca ttcttcagcc    2640
acacgttggt ttgtgtaaaa attgggttca aaaaatcagc agttctttta tgcgcgctac    2700
gaccgaatag acttgtgcat ttacaatggt tcatgggcat cattggtgtc gggtgattgg    2760
gtggtttttc ttcctcagct cttctgttgg atttatcttt cacatttatt ttcccttta    2820 ctcttttttt attgcaaggc ctctctactg atagatggac gggatatcct gtgaatttgt    2880 tattttgtc ccctcttctg atcctccttg ctcttctctc caaatacttt ttttttttac    2940
tctccccaca gacttcctct ggaacatctc cttctcttcc ctaaacctat accaagcgaa    3000
attgctcatc agctctcttg tttcttattt ctctctcttc tcttctgagg catcagacct    3060
ttatatcaaa ttcatgtgta gaaacaccac actggttcca tatatactct tttctttcct    3120
ccacacttaa gaagacattc cattcaaaca tgtgatcata gacctcgagc aggatgagag    3180
gaatcaccat ctataaatca aataaagcct taaattggaa cataactact accatcttgg    3240
acgaactact atgtaataaa ttccattcag aaaccaatca gattcaaatc acatggtact    3300
cctactatgg aacgagtcca ccccccgatg cactactgta gataaataaa ttaaaaatga    3360
cggagaccag accattcccc ccggggtcgg agtcggcacg cagtcggggt actttactta    3420
cgtactgagt aatgtgaatc aaaaactgga tcc                                3453
```

<210> SEQ ID NO 7
<211> LENGTH: 427
<212> TYPE: PRT
<213> ORGANISM: Aspergillus niger

<400> SEQUENCE: 7

Met Pro Pro Pro Ala Ser Ser Val Asp Phe Ser Asn Leu Leu Asn Pro
1               5                   10                  15

```
Gln Asn Asn Ser Thr Asp Ser Thr Pro Ser Thr Pro Val Asp Ser Ser
             20                  25                  30

Lys Thr Pro Ser Thr Pro Ser Thr Gln Ser Asn Ser Asn Met Ala
         35                  40                  45

Ser Ser Val Ser Leu Leu Pro Pro Leu Met Lys Gly Ala Arg Pro Ala
 50                  55                  60

Thr Glu Glu Val Arg Gln Asp Leu Pro Arg Pro Tyr Lys Cys Pro Leu
 65                  70                  75                  80

Cys Asp Arg Ala Phe His Arg Leu Glu His Gln Thr Arg His Ile Arg
                 85                  90                  95

Thr His Thr Gly Glu Lys Pro His Ala Cys Gln Phe Pro Gly Cys Thr
             100                 105                 110

Lys Arg Phe Ser Arg Ser Asp Glu Leu Thr Arg His Ser Arg Ile His
         115                 120                 125

Asn Asn Pro Asn Ser Arg Arg Asn Lys Ala Gln His Leu Ala Ala
 130                 135                 140

Ala Ala Ala Ala Ala Gly Gln Asp Asn Ala Met Ala Asn Thr Ala
145                 150                 155                 160

Ser Ala Met Met Pro Pro Pro Ser Lys Pro Met Thr Arg Ser Ala Pro
                 165                 170                 175

Val Ser Gln Val Gly Ser Pro Asp Ile Ser Pro Pro His Ser Phe Ser
             180                 185                 190

Asn Tyr Ala Ser His Met Arg Ser Asn Leu Gly Pro Tyr Ala Arg Lys
         195                 200                 205

Gly Asp Glu Ala Ser Ser Gly Met Glu Leu Tyr Leu Leu Ala Thr Ala
 210                 215                 220

Ala Ser Gln Val Glu Arg Asp Glu His Phe Asp Phe His Ala Gly Pro
225                 230                 235                 240

Arg Asn His His Leu Phe Ser Ser Arg His His Gly Ser Gly Arg Leu
                 245                 250                 255

Pro Leu Leu Ala Ala Tyr Ala Ile Thr His Asn Met Ser Arg Ser His
             260                 265                 270

Ser Pro Glu Asp Asp Gly Tyr Ser His Arg Val Lys Arg Ser Arg
         275                 280                 285

Pro Asn Ser Pro Asn Ser Thr Ala Pro Ser Pro Thr Phe Ser His
 290                 295                 300

Asp Ser Leu Ser Pro Thr Pro Asp His Thr Pro Leu Ala Thr Pro Ala
305                 310                 315                 320

His Ser Pro Arg Leu Arg Pro Leu Gly Ser Ser Asp Leu His Leu Pro
                 325                 330                 335

Ser Ile Arg His Leu Ser Leu His His Thr Pro Ala Leu Ala Pro Met
             340                 345                 350

Glu Pro Gln Pro Glu Gly Pro Asn Tyr Tyr Ser Pro Ser Gln Gly His
         355                 360                 365

His Gly Pro Ser Ile Ser Asp Ile Met Ser Lys Pro Asp Gly Thr Gln
 370                 375                 380

Arg Lys Leu Pro Val Pro Gln Val Pro Lys Val Ala Val Gln Asp Met
385                 390                 395                 400

Leu Asn Pro Gly Ser Gly Phe Ser Ser Val His Ser Ser Thr Ala Asn
                 405                 410                 415

Ser Val Ala Gly Gly Asp Leu Ala Glu Arg Phe
             420                 425
```

<210> SEQ ID NO 8
<211> LENGTH: 819
<212> TYPE: DNA
<213> ORGANISM: Aspergillus niger

<400> SEQUENCE: 8

| | | | | | | |
|---|---|---|---|---|---|---|
| ggatccgaac | tccaaccggg | gggagtacat | tgagtggccg | cagtggaagg | aatcgcggca | 60 |
| gttgatgaat | tcggagcga | acgacgccag | tctccttacg | gatgatttcc | gcaacgggac | 120 |
| atatgagttc | atcctgcaga | ataccgcggc | gttccacatc | tgatgccatt | ggcggagggg | 180 |
| tccggacggt | caggaactta | gccttatgag | atgaatgatg | gacgtgtctg | gcctcggaaa | 240 |
| aggatatatg | gggatcataa | tagtactagc | catattaatg | aagggcatat | accacgcgtt | 300 |
| ggacctgcgt | tatagcttcc | cgttagttat | agtaccatcg | ttataccagc | caatcaagtc | 360 |
| accacgcacg | accggggacg | gcgaatcccc | gggaattgaa | agaaattgca | tcctaggcca | 420 |
| gtgaggccag | cgattggcca | cctctccaag | cacacagggc | cattctgcag | cgctggtgga | 480 |
| ttcatcgcaa | tttcccccgg | cccggccga | caccgctata | ggctggttct | cccacaccat | 540 |
| cggagattcg | tcgcctaatg | tctcgtccgt | tcacaagctg | aagagcttga | agtggcgaga | 600 |
| tgtctctgca | ggaattcaag | ctagatgcta | agcgatattg | catggcaata | tgtgttgatg | 660 |
| catgtgcttc | ttccttcagc | ttcccctcgt | gcagatgagg | tttggctata | aattgaagtg | 720 |
| gttggtcggg | gttccgtgag | gggctgaagt | gcttcctccc | ttttagacgc | aactgagagc | 780 |
| ctgagcttca | tccccagcat | cattacacct | cagccatgg | | | 819 |

<210> SEQ ID NO 9
<211> LENGTH: 2668
<212> TYPE: DNA
<213> ORGANISM: Neurospora crassa

<400> SEQUENCE: 9

| | | | | | | |
|---|---|---|---|---|---|---|
| ggctggagag | atggtacctt | ctccgtaact | ctctgcattg | catcagcatc | cccagtcgag | 60 |
| cccccccgcg | cccactctcc | cgcacccaca | cgcaccccgt | cctttgggag | actttcgaga | 120 |
| tgcacacccc | ccttcttttt | ttcccccttc | caggctgctc | gcgacccgac | atatgtcgat | 180 |
| tgtggagtct | ggtcttctga | catgaaccct | ctgtaccttc | cctgcttctt | tcaacctcga | 240 |
| tcgaccttt | ctaggccatg | cactgcgtgg | gtcggcgtcg | atggatcccc | agcttttagg | 300 |
| tcatttccaa | ttcaccgact | cgcagctgct | tctttcccca | gtttaagcat | ccaacaattg | 360 |
| gagctccgat | ggcaactcga | gggacataaa | tgtaaggccc | tgtccacact | ccgaatactt | 420 |
| cttctcatca | tctcgtgttc | ttttgaacct | ccattcttca | aacaacttcc | actcctccat | 480 |
| caaagccttc | aaaggttcac | actcctacca | tccaccatcc | accatccact | gtttggtcgt | 540 |
| tggagtatct | accacttttc | gctgttatca | gccacctttc | tccacccaac | caagatctcg | 600 |
| aacaacggat | gaaagacttg | aggatataaa | tacaacgata | cgatcacaac | aatgggtctc | 660 |
| ttctcgaaaa | agtcggctgc | gccgcagacc | caatcacaag | atgagatcga | tctcgctgct | 720 |
| gagcagaagg | tcactttccg | tgccgtcttc | ctcggtgttg | tcgcctccgt | aggtggcttc | 780 |
| atgtttggct | acgtcaggta | cgttttccct | tggcacccct | gttgccccat | tgacatggta | 840 |
| catggttact | gaccatttat | ggacaacagt | ggtcaaattt | ctggtttctt | cgacatggaa | 900 |
| gacttcggtc | gtcggttcgg | taactaccaa | gacgcggatg | gctgggtctt | ctcagcatac | 960 |
| cgccagggtg | ctattgtcgc | cctactccct | gctggtgccc | ttcttggttc | gctcgttgcc | 1020 |
| ggtagaattg | cggatacccct | tggtcgccgt | atcgccatct | ctgcgtccgc | ccttttctcc | 1080 |

```
tgcatcggaa caattatcga gatcgcctcc accacgcact gggcccagtt tgcggtcggt   1140
cgtcttatca ccggtattgg tatcggtgct ctctccgtcg tcgtcccgat gtaccagtct   1200
gagtccgcgc ccgccatcct ccgtggtatc ctcgtctcgt gctaccagct cttcatcact   1260
cttggtatct ggaccgctga gatgatcaac tacggtactc acgacctcag caactccgcc   1320
tcttggcgta ttcccaacgg tatctccttc ctctgggctt tggttctcgg tggcggaata   1380
ttgttccttc ctgagtctcc ccgttatgcc taccgtgttg gtcgcgagga cgaggctcgc   1440
aacaccattg cccgccttgc cggtctcgag cccagcgccc gctctgtcaa catgcaaatc   1500
gatgagatcc gtatgaagct tgaggaggag aaggctggtg ccgacaccaa gtggtacgag   1560
atcttcggac tgctctgtt gcgccgcacc cttatcggta tcattcttca gtctggccag   1620
cagcttactg gtgccaactt cttcttctac tacggaacca cgattttcaa ggctactggt   1680
cttagcgact cttacgttac ccagatcatt cttggttccg tcaacgctgg atgcactgtt   1740
gctggtctct gggttgtcaa gaatgttggc cgccgtaagg ccctcatcgg tggtgccctc   1800
tggatgacca tgtgcttctt ggtctactct ttcgtcggaa gatttgtgct cgaccccgtc   1860
aacccggcta gcactcctca ggccggcaac gtcctcattg tcttctcctg cttcttcatc   1920
gtcgcctttg ccaccacttg gggtcctctc gtctgggccg tcgttgctga gctctaccct   1980
gctcgctacc gtgctcctgc catggccttg gccaccgctt ccaactggct gtggaacttc   2040
ctcatgtccc tcttcacgcg ccccatcacc gactccattg gctacttcta tggcttggtg   2100
ttcgccggat gctgccttgc cctcgccgct ttcgtttggc tctttgtgat cgagtccaag   2160
gaccgcaccc ttgaggagat cgagaccatg tacaaccaga aggtcagccc taggcactcc   2220
acccactggc acgctgaggt cccttcggga ccgcgggatg cggaggagaa gcccgaggtt   2280
cacagtggtt ctgcgacaac ctcaagccat ggagaggttt agaatgcgtc caagtgaaac   2340
ggttctcgtt ctgaaaggaa ttcagaggtt gcgagagtcg attagggatt gtatgatgac   2400
ttgacatgca ccaaaaaatg gaatgcagta gtcagtcatg gtaattgggt ttgaaaggat   2460
aatgaaatgc atggtttagt tgtggtaatg tgattttttc aaggataatg aaatgcatag   2520
ttatttggca attggggttt tcggaaggg tctatggaat ggacattgca ttcttgatag   2580
cacgcataca ataaatcttg atgtgtacgc ttacatccaa atccaccgca tcttggtcta   2640
actcgtgatt cctacgactc cttttaat                                     2668
```

<210> SEQ ID NO 10
<211> LENGTH: 2596
<212> TYPE: DNA
<213> ORGANISM: Neurospora crassa

<400> SEQUENCE: 10

```
ggctggagag atggtacctt ctccgtaact ctctgcattg catcagcatc cccagtcgag     60 ccccccgcg cccactctcc cgcacccaca cgcaccccgt cctttgggag actttcgaga    120
tgcacacccc ccttcttttt ttcccccttc caggctgctc gcgacccgac atatgtcgat    180
tgtggagtct ggtcttctga catgaaccct ctgtaccttc cctgcttctt tcaacctcga    240
tcgacctttt ctaggccatg cactgcgtgg gtcggcgtcg atggatcccc agcttttagg    300
tcatttccaa ttcaccgact cgcagctgct tctttcccca gtttaagcat ccaacaattg    360
gagctccgat ggcaactcga gggacataaa tgtaaggccc tgtccacact ccgaatactt    420
cttctcatca tctcgtgttc ttttgaacct ccattcttca aacaacttcc actcctccat    480
```

| | |
|---|---|
| caaagccttc aaaggttcac actcctacca tccaccatcc accatccact gtttggtcgt | 540 |
| tggagtatct accacttttc gctgttatca gccacctttc tccacccaac caagatctcg | 600 |
| aacaacggat gaaagacttg aggatataaa tacaacgata cgatcacaac aatgggtctc | 660 |
| ttctcgaaaa agtcggctgc gccgcagacc caatcacaag atgagatcga tctcgctgct | 720 |
| gagcagaagg tcactttccg tgccgtcttc ctcggtgttg tcgcctccgt aggtggcttc | 780 |
| atgtttggct acgtcagtgg tcaaatttct ggtttcttcg acatggaaga cttcggtcgt | 840 |
| cggttcggta actaccaaga cgcggatggc tgggtcttct cagcataccg ccagggtgct | 900 |
| attgtcgccc tactcctgc tggtgccctt cttggttcgc tcgttgccgg tagaattgcg | 960 |
| gataccttg gtcgccgtat cgccatctct gcgtccgccc ttttctcctg catcggaaca | 1020 |
| attatcgaga tcgcctccac cacgcactgg gcccagtttg cggtcggtcg tcttatcacc | 1080 |
| ggtattggta tcggtgctct ctccgtcgtc gtcccgatgt accagtctga gtccgcgccc | 1140 |
| gccatcctcc gtggtatcct cgtctcgtgc taccagctct tcatcactct tggtatctgg | 1200 |
| accgctgaga tgatcaacta cggtactcac gacctcagca actccgcctc ttggcgtatt | 1260 |
| cccaacggta tctccttcct ctgggctttg ttctcggtg gcggaatatt gttccttcct | 1320 |
| gagtctcccc gttatgccta ccgtgttggt cgcgaggacg aggctcgcaa caccattgcc | 1380 |
| cgccttgccg gtctcgagcc cagcgcccgc tctgtcaaca tgcaaatcga tgagatccgt | 1440 |
| atgaagcttg aggaggagaa ggctggtgcc gacaccaagt ggtacgagat cttcggacct | 1500 |
| gctctgttgc gccgcaccct tatcggtatc attcttcagt ctggccagca gcttactggt | 1560 |
| gccaacttct tcttctacta cggaaccacg attttcaagg ctactggtct tagcgactct | 1620 |
| tacgttaccc agatcattct tggttccgtc aacgctggat gcactgttgc tggtctctgg | 1680 |
| gttgtcaaga atgttggccg ccgtaaggcc ctcatcggtg gtgccctctg gatgaccatg | 1740 |
| tgcttcttgg tctactcttt cgtcggaaga tttgtgctcg accccgtcaa cccggctagc | 1800 |
| actcctcagg ccggcaacgt cctcattgtc ttctcctgct tcttcatcgt cgcctttgcc | 1860 |
| accacttggg gtcctctcgt ctgggccgtc gttgctgagc tctaccctgc tcgctaccgt | 1920 |
| gctcctgcca tggccttggc caccgcttcc aactggctgt ggaacttcct catgtccctc | 1980 |
| ttcacgcgcc ccatcaccga ctccattggc tacttctatg gcttggtgtt cgccggatgc | 2040 |
| tgccttgccc tcgccgcttt cgtttggctc tttgtgatcg agtccaagga ccgcacccctt | 2100 |
| gaggagatcg agaccatgta caaccagaag gtcagcccta ggcactccac ccactggcac | 2160 |
| gctgaggtcc cttcgggacc gcgggatgcg gaggagaagc ccgaggttca cagtggttct | 2220 |
| gcgacaacct caagccatgg agaggtttag aatgcgtcca agtgaaacgg ttctcgttct | 2280 |
| gaaaggaatt cagaggttgc gagagtcgat tagggattgt atgatgactt gacatgcacc | 2340 |
| aaaaaatgga atgcagtagt cagtcatggt aattgggttt gaaaggataa tgaaatgcat | 2400 |
| ggtttagttg tggtaatgtg attttttcaa ggataatgaa atgcatagtt atttggcaat | 2460 |
| tggggttttt cggaagggtc tatggaatgg acattgcatt cttgatagca cgcatacaat | 2520 |
| aaatcttgat gtgtacgctt acatccaaat ccaccgcatc ttggtctaac tcgtgattcc | 2580 |
| tacgactcct tttaat | 2596 |

<210> SEQ ID NO 11
<211> LENGTH: 532
<212> TYPE: PRT
<213> ORGANISM: Neurospora crassa

<400> SEQUENCE: 11

```
Met Gly Leu Phe Ser Lys Lys Ser Ala Ala Pro Gln Thr Gln Ser Gln
1               5                   10                  15

Asp Glu Ile Asp Leu Ala Ala Glu Gln Lys Val Thr Phe Arg Ala Val
            20                  25                  30

Phe Leu Gly Val Val Ala Ser Val Gly Gly Phe Met Phe Gly Tyr Val
        35                  40                  45

Ser Gly Gln Ile Ser Gly Phe Phe Asp Met Glu Asp Phe Gly Arg Arg
    50                  55                  60

Phe Gly Asn Tyr Gln Asp Ala Asp Gly Trp Val Phe Ser Ala Tyr Arg
65                  70                  75                  80

Gln Gly Ala Ile Val Ala Leu Leu Pro Ala Gly Ala Leu Leu Gly Ser
                85                  90                  95

Leu Val Ala Gly Arg Ile Ala Asp Thr Leu Gly Arg Arg Ile Ala Ile
                100                 105                 110

Ser Ala Ser Ala Leu Phe Ser Cys Ile Gly Thr Ile Ile Glu Ile Ala
            115                 120                 125

Ser Thr Thr His Trp Ala Gln Phe Ala Val Gly Arg Leu Ile Thr Gly
    130                 135                 140

Ile Gly Ile Gly Ala Leu Ser Val Val Pro Met Tyr Gln Ser Glu
145                 150                 155                 160

Ser Ala Pro Ala Ile Leu Arg Gly Ile Leu Val Ser Cys Tyr Gln Leu
                165                 170                 175

Phe Ile Thr Leu Gly Ile Trp Thr Ala Glu Met Ile Asn Tyr Gly Thr
                180                 185                 190

His Asp Leu Ser Asn Ser Ala Ser Trp Arg Ile Pro Asn Gly Ile Ser
            195                 200                 205

Phe Leu Trp Ala Leu Val Leu Gly Gly Gly Ile Leu Phe Leu Pro Glu
    210                 215                 220

Ser Pro Arg Tyr Ala Tyr Arg Val Gly Arg Glu Asp Glu Ala Arg Asn
225                 230                 235                 240

Thr Ile Ala Arg Leu Ala Gly Leu Glu Pro Ser Ala Arg Ser Val Asn
                245                 250                 255

Met Gln Ile Asp Glu Ile Arg Met Lys Leu Glu Glu Lys Ala Gly
                260                 265                 270

Ala Asp Thr Lys Trp Tyr Glu Ile Phe Gly Pro Ala Leu Leu Arg Arg
            275                 280                 285

Thr Leu Ile Gly Ile Ile Leu Gln Ser Gly Gln Gln Leu Thr Gly Ala
    290                 295                 300

Asn Phe Phe Tyr Tyr Gly Thr Thr Ile Phe Lys Ala Thr Gly Leu
305                 310                 315                 320

Ser Asp Ser Tyr Val Thr Gln Ile Ile Leu Gly Ser Val Asn Ala Gly
                325                 330                 335

Cys Thr Val Ala Gly Leu Trp Val Val Lys Asn Val Gly Arg Arg Lys
            340                 345                 350

Ala Leu Ile Gly Gly Ala Leu Trp Met Thr Met Cys Phe Leu Val Tyr
    355                 360                 365

Ser Phe Val Gly Arg Phe Val Leu Asp Pro Val Asn Pro Ala Ser Thr
370                 375                 380

Pro Gln Ala Gly Asn Val Leu Ile Val Phe Ser Cys Phe Phe Ile Val
385                 390                 395                 400

Ala Phe Ala Thr Thr Trp Gly Pro Leu Val Trp Ala Val Val Ala Glu
            405                 410                 415
```

```
Leu Tyr Pro Ala Arg Tyr Arg Ala Pro Ala Met Ala Leu Ala Thr Ala
            420             425             430

Ser Asn Trp Leu Trp Asn Phe Leu Met Ser Leu Phe Thr Arg Pro Ile
        435             440             445

Thr Asp Ser Ile Gly Tyr Phe Tyr Gly Leu Val Phe Ala Gly Cys Cys
    450             455             460

Leu Ala Leu Ala Ala Phe Val Trp Leu Phe Val Ile Glu Ser Lys Asp
465             470             475             480

Arg Thr Leu Glu Glu Ile Glu Thr Met Tyr Asn Gln Lys Val Ser Pro
                485             490             495

Arg His Ser Thr His Trp His Ala Glu Val Pro Ser Gly Pro Arg Asp
            500             505             510

Ala Glu Glu Lys Pro Glu Val His Ser Gly Ser Ala Thr Thr Ser Ser
            515             520             525

His Gly Glu Val
    530
```